(12) United States Patent
Liu et al.

(10) Patent No.: US 9,682,962 B2
(45) Date of Patent: Jun. 20, 2017

(54) PYRAZOLYL PYRIMIDINAMINE COMPOUND AND APPLICATION THEREOF

(71) Applicant: SHENYANG SINOCHEM AGROCHEMICALS R&D CO., LTD., Liaoning (CN)

(72) Inventors: Changling Liu, Liaoning (CN); Xufeng Sun, Liaoning (CN); Jie Zhao, Liaoning (CN); Lizeng Wang, Liaoning (CN); Keke Li, Liaoning (CN); Jinbo Zhang, Liaoning (CN); Xuanming Chen, Liaoning (CN); Aiying Guan, Liaoning (CN); Yuquan Song, Liaoning (CN); Jie Lan, Liaoning (CN); Sen Ma, Liaoning (CN); Lijun Ru, Liaoning (CN)

(73) Assignee: Shenyang Sinochem Agrochemicals R&D CO., LTD., Shenyang (CN)

( * ) Notice: Subject to any disclaimer, the term of this patent is extended or adjusted under 35 U.S.C. 154(b) by 0 days.

(21) Appl. No.: 15/103,499

(22) PCT Filed: Dec. 11, 2014

(86) PCT No.: PCT/CN2014/093564
§ 371 (c)(1),
(2) Date: Jun. 10, 2016

(87) PCT Pub. No.: WO2015/085935
PCT Pub. Date: Jun. 18, 2015

(65) Prior Publication Data
US 2016/0332991 A1 Nov. 17, 2016

(30) Foreign Application Priority Data
Dec. 13, 2013 (CN) .......................... 2013 1 0684677

(51) Int. Cl.
| | | |
|---|---|---|
| *C07D 403/12* | (2006.01) | |
| *C07D 403/14* | (2006.01) | |
| *A01N 43/56* | (2006.01) | |
| *C07D 401/14* | (2006.01) | |
| *C07D 417/14* | (2006.01) | |

(52) U.S. Cl.
CPC ........... *C07D 403/12* (2013.01); *A01N 43/56* (2013.01); *C07D 401/14* (2013.01); *C07D 403/14* (2013.01); *C07D 417/14* (2013.01)

(58) Field of Classification Search
CPC .. C07D 401/14; C07D 403/12; C07D 403/14; C07D 417/14; A01N 43/56
USPC .......................................... 544/328; 514/256
See application file for complete search history.

(56) References Cited

U.S. PATENT DOCUMENTS

| | | | |
|---|---|---|---|
| 4,845,097 | A | 7/1989 | Matsumoto et al. |
| 4,977,264 | A | 12/1990 | Mills et al. |
| 4,985,426 | A | 1/1991 | Yoshioka et al. |
| 5,468,751 | A | 11/1995 | Kristiansen et al. |
| 5,925,644 | A | 7/1999 | Jakobi et al. |
| 6,090,815 | A | 7/2000 | Masuda et al. |
| 2004/0092402 | A1 | 5/2004 | Kuragano et al. |
| 2010/0023164 | A1 | 1/2010 | Yoshizawa |

FOREIGN PATENT DOCUMENTS

| | | |
|---|---|---|
| DE | 19647317 A1 | 5/1998 |
| EP | 0264217 A2 | 4/1988 |
| EP | 0356158 A1 | 2/1990 |
| EP | 0370704 A2 | 5/1990 |
| EP | 0530149 A1 | 3/1993 |
| EP | 0665225 A1 | 8/1995 |
| JP | H8-269021 A | 10/1996 |
| JP | H8-291149 A | 11/1996 |
| JP | 2000-007662 A | 1/2000 |
| JP | 2001-504473 A1 | 4/2001 |
| JP | 3511729 B2 | 3/2004 |

(Continued)

OTHER PUBLICATIONS

International Search Report for PCT/CN2014/093564, dated Mar. 17, 2015 in English and Chinese Language.

(Continued)

*Primary Examiner* — Deepak Rao
(74) *Attorney, Agent, or Firm* — Smith, Gambrell & Russell, LLP

(57) ABSTRACT

Disclosed are pyrazolyl pyrimidinamine compounds with structures as shown in Formula I:

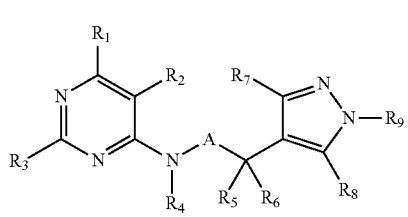

I

The definitions of each of the substituents can be seen in the description.
The compounds of present invention have a broad spectrum of bactericidal, insecticidal and acaricidal activity, and have good control effect on downy mildew of cucumber, powdery mildew of wheat, corn rust, anthracnosis of cucumber and the like, and especially have better control effect on downy mildew of cucumber, powdery mildew of wheat and anthracnosis of cucumber. The compounds of present invention also show good insecticidal activity, part of the compounds, at very low doses, have excellent control effect on diseases caused by *Plutella xylostella*, armyworm, *Myzus persicae*, *Tetranychus cinnabarinus* etc.

11 Claims, No Drawings

(56) References Cited

FOREIGN PATENT DOCUMENTS

| | | |
|---|---|---|
| JP | 3543411 B2 | 7/2004 |
| JP | 2008-269021 A | 11/2008 |
| JP | 2009-124613 A | 6/2009 |
| JP | 2010-036355 A | 2/2010 |
| WO | 92/08704 A1 | 5/1992 |
| WO | 95/07278 | 3/1995 |
| WO | 98/22446 A1 | 5/1998 |
| WO | 2007/045989 A1 | 4/2007 |
| WO | 2009/115257 A1 | 9/2009 |
| ZA | 9710187 A | 5/1997 |

OTHER PUBLICATIONS

Rao et al. Convenient Synthesis of 3H-Pyrrolo[2,3-c]Isoquinolines and 3-H-Pyrrolo[2,3-c][1,7]-, 3,4-Benzo[c][1,7]-, and Dihydropyrido [4,3-c][1,8] Naphthyridines Via Palladium-Assisted Nucleophilic Amination. Heterocycles, vol. 56, 2002, pp. 443-455.
International Preliminary Report on Patentability for PCT/CN2014/093564 dated Jun. 14, 2016. (Chinese with English Translation). 10 pages.
Written Opinion for PCT/CN2014/093564. (Chinese with English Translation) Dated Mar. 17, 2015. 8 pages.
Han, et al. Preparation of 1-subsituted and 1,4-disubstituted derivatives of 2,6-naphthyridine. Arkivoc, 2002 (x) 40-51.
Menegatti, et al. Design, Synthesis and Pharmacological Profile of Novel Dopamine D2 Receptor Ligands. Bioorganic & Medicinal Chemistry, 11 (2003), 4807-4813.
Vera-DiVaio, et al. Synthesis, antichagasic in vitro evaluation, cytotoxicity assays, molecular modeling and SAR/QSAR studies of a 2-phenyl-3-(1-phenyl-1H-pyrazol-4-yl)-acrylic acid benzylidene-carbohydrazide series. Bioorganic & Medicinal Chemistry, 17, (2009), 295-302.
Lalancette, et al. Reductions with Sulfurated Borohydrides. VI. The Reduction of Nitro, Nitrile, Amide and Nitroso Groups. Canadian Journal of Chemistry. 49. (1971), 2990-2995.
Chesterfield, et al. Pyrimidines. Part III. Halogeno- and Hydrazino-pyrimidines. Heterocycles. (1955), 3478-3481.
Freifelder, Morris. A Low Pressure Process for the Reduction of Nitriles. Use of Rhodium Catalyst. Journal of the American Chemical Society, 82 (1960), 2386-2389.
Brown, et al. Hydroboration. III. The Reduction of Organic Compounds by Diborane, an Acid-type Reducing Agent. Journal of the American Chemical Society, 82 (1960), 681-686.
Snyder, et al. A Synthesis of 6-Methylindole and dl-6-Methyltrptophan. Journal of the American Chemical Society, 70 (1948), 3787-3788.
Secrist III, et al. Amine Hydrochlorides by Reduction in the Presence of Chloroform. The Journal of Organic Chemistry, 37, (1972), 335-336.
Löfberg, et al. Efficient Solvent-Free Selective, Monoalkylation of Arylacetonitriles with Mono-, Bis-, and Tris-primary Alcohols Catalyzed by a Cp*Ir Complex. The Journal of Organic Chemistry, 71, (2006), 8023-8027.
Close, W. J. An Improved Synthesis of Cyclopropyl Phenyl Ketone and Related Substances. Journal of the American Chemical Society, 79, (1957), 1455-1458.
Biggs, et al. Decamethylenediamine. Organic Syntheses, Coll. vol. 3, p. 229 (1955); vol. 27, p. 18 (1947). 3 pgs.
Robinson, Jr. et al. β-Phenylethylamine. Organic Syntheses, Coll. vol. 3, p. 720 (1955); vol. 23. p. 71, (1943). 5 pgs.
Rasmussen, et al. Aspects of the amination of 4-t-butyl-5-halogenopyrimidines by potassium amide in liquid ammonia. Recueil des Travaux Chimiques des Pays-Bas, 97, (1978), 288-292.
Tsai, et al. Lithium Naphthalenide-Induced Reductive Alkylation and Addition of Aryl- and Heteroaryl-Substituted Dialkylacetonitriles. Synthesis, 24 (2010), 4242-4250.
Mandal, et al. An Efficient General Method for the Conversation of a-Quaternary Nitriles into Amides. Synthesis, 9, (1983), 727-729.
Luo, et al. Simple Transformation of Nitrile into Ester by the Use of Chlorotrimethylsilane. Tetrahedron Letters, 39, (1998), 9455-9456.

PYRAZOLYL PYRIMIDINAMINE COMPOUND AND APPLICATION THEREOF

FIELD OF THE INVENTION

The invention relates to fungicide, pesticide and acaricide. Specifically to a novel pyrazolyl pyrimidinamine compound and application thereof.

BACKGROUND OF THE INVENTION

Disclosed in Patent WO9507278 were the pyrazolyl pyrimidinamine compounds having general formula and the specific compounds CK1 and CK2 applied as fungicide, insecticide and acaricide in agriculture.

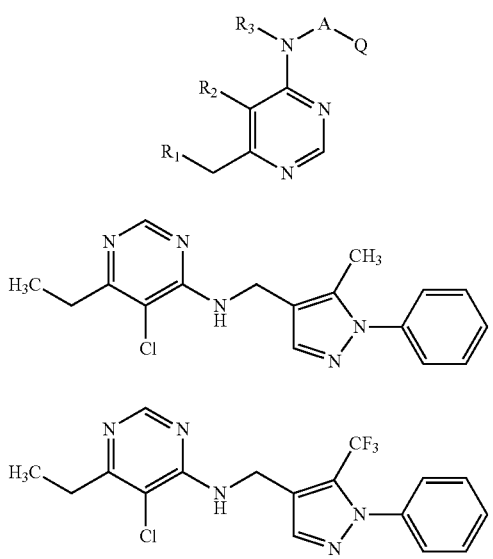

The following compounds CK3, CK4 and CK5 were retrieved via Scifinder database without specific literature disclosed.

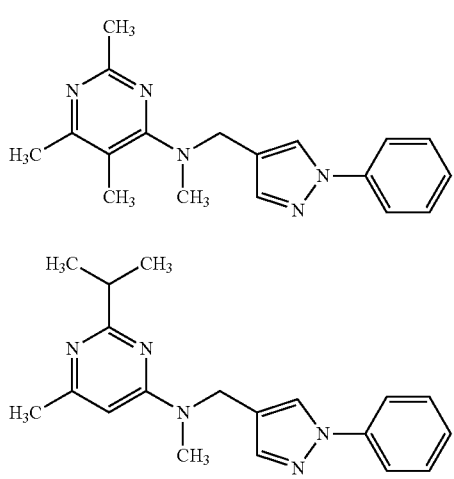

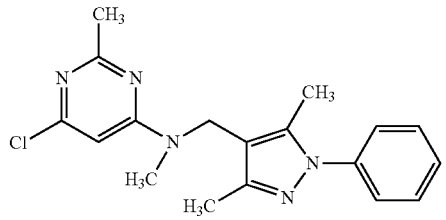

However, pyrazolyl pyrimidinamine compounds represented by general formula I of the present invention have not been reported in prior literatures.

SUMMARY OF THE INVENTION

The object of the present invention is to provide pyrazolyl pyrimidinamine compounds, which can be used to prepare fungicides, pesticides, and acaricides against harmful fungus, bacteria, insects and mites in agricultural or other fields.

Detailed descriptions of the invention are as follows:

The present invention provides a kind of pyrazolyl pyrimidinamine compounds having a structure as represented by general formula I:

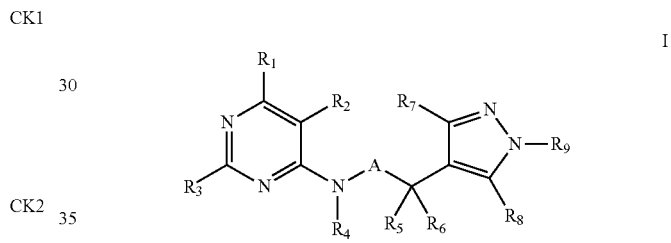

Wherein:

$R_1$ is selected from halogen, $C_1$-$C_{12}$alkyl, $C_3$-$C_{12}$cycloalkyl, halo$C_1$-$C_{12}$alkyl, $C_2$-$C_{12}$alkenyl, halo$C_2$-$C_{12}$alkenyl, $C_2$-$C_{12}$alkynyl, halo$C_2$-$C_{12}$alkynyl, $C_1$-$C_{12}$alkoxy$C_1$-$C_{12}$alkyl or halo$C_1$-$C_{12}$alkoxy$C_1$-$C_{12}$alkyl;

$R_2$ is selected from halogen, cyano, nitro, $C_1$-$C_{12}$alkyl, $C_1$-$C_{12}$alkoxy or halo$C_1$-$C_{12}$alkoxy;

$R_3$ is selected from H, halogen, $C_1$-$C_{12}$alkyl, halo$C_1$-$C_{12}$alkyl, $C_3$-$C_8$cycloalkyl, $C_1$-$C_{12}$alkoxy, $C_1$-$C_{12}$alkylthio or $C_1$-$C_{12}$alkylsulfonyl;

$R_4$ is selected from H, OH, H(C)=O, $C_1$-$C_{12}$alkyl, halo$C_1$-$C_{12}$alkyl, $C_1$-$C_{12}$alkoxy, halo$C_1$-$C_{12}$alkoxy, $C_3$-$C_{12}$cycloalkyl, $C_1$-$C_{12}$alkylthio, $C_2$-$C_{12}$alkenylthio, $C_2$-$C_{12}$alkenyl, $C_2$-$C_{12}$alkynyl, halo$C_2$-$C_{12}$alkenyl, halo$C_2$-$C_{12}$alkynyl, $C_1$-$C_{12}$alkoxy$C_1$-$C_{12}$alkyl, halo$C_1$-$C_{12}$alkoxy$C_1$-$C_{12}$alkyl, $C_1$-$C_{12}$alkylthio$C_1$-$C_{12}$alkyl, halo$C_1$-$C_{12}$alkylthio$C_1$-$C_{12}$alkyl, $C_1$-$C_{12}$alkylsulfinyl, halo$C_1$-$C_{12}$alkylsulfinyl, $C_1$-$C_{12}$alkylsulfonyl, halo$C_1$-$C_{12}$alkylsulfonyl, $C_1$-$C_{12}$alkylaminosulfonyl, di($C_1$-$C_{12}$alkyl)aminosulfonyl, $C_1$-$C_{12}$alkylsulfonylaminocarbonyl, $C_1$-$C_{12}$alkylcarbonylaminosulfonyl, $C_3$-$C_{12}$cycloalkyloxycarbonyl, $C_1$-$C_{12}$alkylcarbonyl, halo$C_1$-$C_{12}$alkylcarbonyl, $C_1$-$C_{12}$alkoxycarbonyl, halo$C_1$-$C_{12}$alkoxycarbonyl, $C_1$-$C_{12}$alkylcarbonyl$C_1$-$C_{12}$alkyl, $C_1$-$C_{12}$alkoxycarbonyl$C_1$-$C_{12}$alkyl, $C_1$-$C_{12}$alkylaminocarbonyl, di($C_1$-$C_{12}$alkyl)aminocarbonyl, $C_2$-$C_{12}$alkenoxycarbonyl, $C_2$-$C_{12}$alkynoxycarbonyl, $C_1$-$C_{12}$alkoxy$C_1$-$C_{12}$alkoxycarbonyl, $C_1$-$C_{12}$alkylaminothio, di($C_1$-$C_{12}$alkyl)aminothio, unsubstituted or further substituted (hetero)arylcarbonyl$C_1$-$C_6$alkyl, (hetero)arylcarbonyl, (hetero)aryloxycarbonyl, (hetero)aryl$C_1$-$C_6$alkyloxycarbonyl or (hetero)aryl$C_1$-$C_6$alkyl by 1 to 5 following groups: halogen, nitro, cyano, $C_1$-$C_6$alkyl, halo$C_1$-$C_6$alkyl, $C_1$-$C_6$alkoxy or halo$C_1$-$C_6$alkoxy;

$R_5$, $R_6$ may be the same or different, selected respectively from H, halogen, $C_1$-$C_{12}$alkyl or $C_1$-$C_{12}$alkoxy; or $R_5$, $R_6$ and their conjoint carbon can also form a $C_3$-$C_8$ cycle;

$R_7$ is selected from H, $C_1$-$C_{12}$alkyl or halo$C_1$-$C_{12}$alkyl;

$R_8$ is selected from H, $C_1$-$C_{12}$alkyl or halo$C_1$-$C_{12}$alkyl;

$R_9$ is selected from $C_1$-$C_{12}$alkyl, $C_3$-$C_8$cycloalkyl, halo$C_1$-$C_{12}$alkyl, $C_1$-$C_{12}$alkylcarbonyl, halo$C_1$-$C_{12}$alkylcarbonyl, $C_1$-$C_{12}$alkylsulfonyl, halo$C_1$-$C_{12}$alkylsulfonyl, $C_1$-$C_{12}$alkoxycarbonyl, $C_1$-$C_{12}$alkoxy$C_1$-$C_{12}$alkyl, $C_1$-$C_{12}$alkoxycarbonyl$C_1$-$C_{12}$alkyl, unsubstituted or further substituted (hetero)aryl, (hetero)arylmethyl, (hetero)arylcarbonyl, (hetero)arylmethylcarbonyl or (hetero)alkyloxycarbonyl by 1 to 5 $R_{10}$;

$R_{10}$ is selected from halogen, OH, amino, cyano, nitro, $C_1$-$C_{12}$alkyl, halo$C_1$-$C_{12}$alkyl, $C_1$-$C_{12}$alkoxy, halo$C_1$-$C_{12}$alkoxy, $C_3$-$C_{12}$cycloalkyl, $C_1$-$C_{12}$alkylamino, halo$C_1$-$C_{12}$alkylamino, di($C_1$-$C_{12}$alkyl)amino, halodi($C_1$-$C_{12}$alkyl)amino, C(=O)$NR_{11}R_{12}$, $C_1$-$C_{12}$alkylthio, halo$C_1$-$C_{12}$alkylthio, $C_2$-$C_{12}$alkenyl, $C_2$-$C_{12}$alkynyl, $C_2$-$C_{12}$alkenoxy, halo$C_2$-$C_{12}$alkenoxy, $C_2$-$C_{12}$alkynoxy, halo$C_2$-$C_{12}$alkynoxy, $C_1$-$C_{12}$alkylsulfonyl, halo$C_1$-$C_{12}$alkylsulfonyl, $C_1$-$C_{12}$alkylcarbonyl, halo$C_1$-$C_{12}$alkylcarbonyl, $C_1$-$C_{12}$alkoxycarbonyl, halo$C_1$-$C_{12}$alkoxycarbonyl, $C_1$-$C_{12}$alkoxy$C_1$-$C_{12}$alkyl, halo$C_1$-$C_{12}$alkoxy$C_1$-$C_{12}$alkyl, $C_1$-$C_{12}$alkylthio$C_1$-$C_{12}$alkyl, halo$C_1$-$C_{12}$alkylthio$C_1$-$C_{12}$alkyl, $C_1$-$C_{12}$alkoxycarbonyl$C_1$-$C_{12}$alkyl, halo$C_1$-$C_{12}$alkoxycarbonyl$C_1$-$C_{12}$alkyl, $C_1$-$C_{12}$alkylthiocarbonyl$C_1$-$C_{12}$alkyl, halo$C_1$-$C_{12}$alkylthiocarbonyl$C_1$-$C_{12}$alkyl, $C_1$-$C_{12}$alkylcarbonyloxy, halo$C_1$-$C_{12}$alkylcarbonyloxy, $C_1$-$C_{12}$alkoxycarbonyloxy, halo$C_1$-$C_{12}$alkoxycarbonyloxy, $C_1$-$C_{12}$alkylsulfonyloxy, halo$C_1$-$C_{12}$alkylsulfonyloxy, $C_1$-$C_{12}$alkoxy$C_1$-$C_{12}$alkoxy or halo$C_1$-$C_{12}$alkoxy$C_1$-$C_{12}$alkoxy;

$R_{11}$, $R_{12}$ may be the same or different, selected respectively from H, $C_1$-$C_{12}$alkyl or halo$C_1$-$C_{12}$alkyl;

A is selected from (CHR$_{13}$)m; m is selected from 1 or 2;

$R_{13}$ is selected from H, $C_1$-$C_{12}$alkyl or halo$C_1$-$C_{12}$alkyl;

Or the salts formed from the compounds represented by general formula I.

The preferred compounds represented by general formula I of this invention are:

$R_1$ is selected from halogen, $C_1$-$C_6$alkyl, $C_3$-$C_6$cycloalkyl, halo$C_1$-$C_6$alkyl, $C_2$-$C_6$alkenyl, halo$C_2$-$C_6$alkenyl, $C_2$-$C_6$alkynyl, halo$C_2$-$C_6$alkynyl, $C_1$-$C_6$alkoxy$C_1$-$C_6$alkyl or halo$C_1$-$C_6$alkoxy$C_1$-$C_6$alkyl;

$R_2$ is selected from halogen, cyano, nitro, $C_1$-$C_6$alkyl, $C_1$-$C_6$alkoxy or halo$C_1$-$C_6$alkoxy;

$R_3$ is selected from H, halogen, $C_1$-$C_6$alkyl, halo$C_1$-$C_6$alkyl, $C_3$-$C_6$cycloalkyl, $C_1$-$C_6$alkoxy, $C_1$-$C_6$alkylthio or $C_1$-$C_6$alkylsulfonyl;

$R_4$ is selected from H, OH, H(C)=O, $C_1$-$C_6$alkyl, $C_1$-$C_6$alkylcarbonyl or $C_1$-$C_6$alkylsulfonyl;

$R_5$, $R_6$ may be the same or different, selected respectively from H, halogen, $C_1$-$C_6$alkyl or $C_1$-$C_6$alkoxy; or $R_5$, $R_6$ and their conjoint carbon can also form a $C_3$-$C_6$ cycle;

$R_7$ is selected from H, $C_1$-$C_6$alkyl or halo$C_1$-$C_6$alkyl;

$R_8$ is selected from H, $C_1$-$C_6$alkyl or halo$C_1$-$C_6$alkyl;

$R_9$ is selected from $C_1$-$C_6$alkyl, $C_3$-$C_6$cycloalkyl, halo$C_1$-$C_6$alkyl, $C_1$-$C_6$alkylcarbonyl, halo$C_1$-$C_6$alkylcarbonyl, $C_1$-$C_6$alkylsulfonyl, halo$C_1$-$C_6$alkylsulfonyl, $C_1$-$C_6$alkoxycarbonyl, $C_1$-$C_6$alkoxy$C_1$-$C_6$alkyl, $C_1$-$C_6$alkoxycarbonyl$C_1$-$C_6$alkyl, unsubstituted or further substituted (hetero)aryl, (hetero)arylmethyl, (hetero)arylcarbonyl, (hetero)arylmethylcarbonyl or (hetero)alkyloxycarbonyl by 1 to 5 $R_{10}$;

$R_{10}$ is selected from halogen, OH, amino, cyano, nitro, $C_1$-$C_6$alkyl, halo$C_1$-$C_6$alkyl, $C_1$-$C_6$alkoxy, halo$C_1$-$C_6$alkoxy, $C_3$-$C_6$cycloalkyl, $C_1$-$C_6$alkylamino, halo$C_1$-$C_6$alkylamino, di($C_1$-$C_6$alkyl)amino, halodi($C_1$-$C_6$alkyl)amino, C(=O)$NR_{11}R_{12}$, $C_1$-$C_6$alkylthio, halo$C_1$-$C_6$alkylthio, $C_2$-$C_6$alkenyl, $C_2$-$C_6$alkynyl, $C_2$-$C_6$alkenoxy, halo$C_2$-$C_6$alkenoxy, $C_2$-$C_6$alkynoxy, halo$C_2$-$C_6$alkynoxy, $C_1$-$C_6$alkylsulfonyl, halo$C_1$-$C_6$alkylsulfonyl, $C_1$-$C_6$alkylcarbonyl, halo$C_1$-$C_6$alkylcarbonyl, $C_1$-$C_6$alkoxycarbonyl, halo$C_1$-$C_6$alkoxycarbonyl, $C_1$-$C_6$alkoxy$C_1$-$C_{12}$alkyl, halo$C_1$-$C_6$alkoxy$C_1$-$C_6$alkyl, $C_1$-$C_6$alkylthio$C_1$-$C_6$alkyl, halo$C_1$-$C_6$alkylthio$C_1$-$C_6$alkyl, $C_1$-$C_6$alkoxycarbonyl$C_1$-$C_6$alkyl, halo$C_1$-$C_6$alkoxycarbonyl$C_1$-$C_6$alkyl, $C_1$-$C_6$alkylthiocarbonyl$C_1$-$C_6$alkyl, halo$C_1$-$C_6$alkylthiocarbonyl$C_1$-$C_6$alkyl, $C_1$-$C_6$alkylcarbonyloxy, halo$C_1$-$C_6$alkylcarbonyloxy, $C_1$-$C_6$alkoxycarbonyloxy, halo$C_1$-$C_6$alkoxycarbonyloxy, $C_1$-$C_6$alkylsulfonyloxy, halo$C_1$-$C_6$alkylsulfonyloxy, $C_1$-$C_6$alkoxy$C_1$-$C_6$alkoxy or halo$C_1$-$C_6$alkoxy$C_1$-$C_6$alkoxy;

$R_{11}$, $R_{12}$ may be the same or different, selected respectively from H, $C_1$-$C_6$alkyl or halo$C_1$-$C_6$alkyl;

A is selected from (CHR$_{13}$)$_m$; m is selected from 1 or 2;

$R_{13}$ is selected from H, $C_1$-$C_6$alkyl or halo$C_1$-$C_6$alkyl;

Or the salts formed from the compounds represented by general formula I.

In the general formula I, the preferred compounds represented by general formula IA, IB, IC, ID, IE or IF of this invention are:

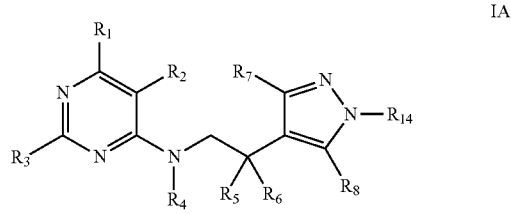

IA

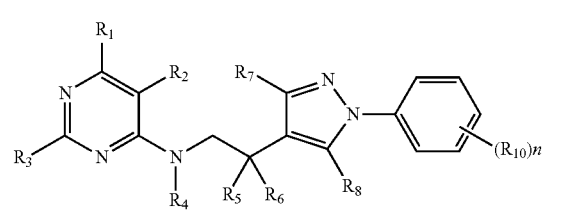

IB

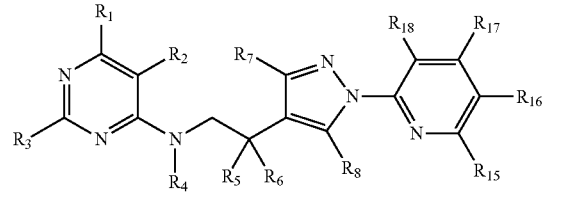

IC

-continued

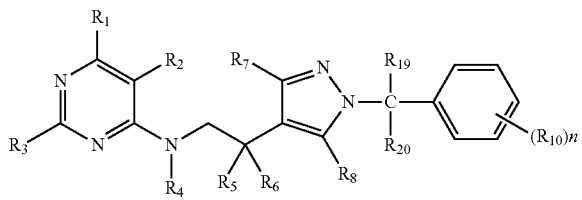
ID

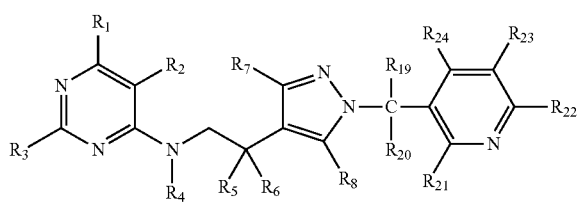
IE

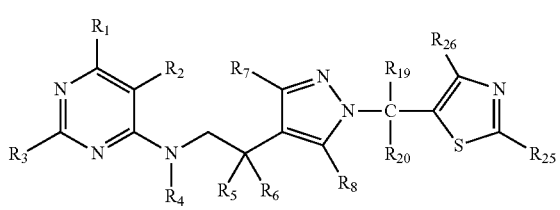
IF

Wherein:

$R_1$ is selected from halogen, $C_1$-$C_4$alkyl, $C_3$-$C_4$cycloalkyl, halo$C_1$-$C_4$alkyl, $C_2$-$C_4$alkenyl, halo$C_2$-$C_4$alkenyl, $C_2$-$C_4$alkynyl, halo$C_2$-$C_4$alkynyl, $C_1$-$C_4$alkoxy$C_1$-$C_4$alkyl or halo$C_1$-$C_4$alkoxy$C_1$-$C_4$alkyl;

$R_2$ is selected from halogen, cyano, nitro, $C_1$-$C_4$alkyl, $C_1$-$C_4$alkoxy or halo$C_1$-$C_4$alkoxy;

$R_3$ is selected from H, halogen, $C_1$-$C_4$alkyl, halo$C_1$-$C_4$alkyl, $C_3$-$C_4$cycloalkyl, $C_1$-$C_4$alkoxy, $C_1$-$C_4$alkylthio or $C_1$-$C_4$alkylsulfonyl;

$R_4$ is selected from H, OH, H(C)=O, $C_1$-$C_4$alkyl, $C_1$-$C_4$alkylcarbonyl or $C_1$-$C_4$alkylsulfonyl;

$R_5$, $R_6$ may be the same or different, selected respectively from H, halogen, $C_1$-$C_4$alkyl or $C_1$-$C_4$alkoxy; or $R_5$, $R_6$ and their conjoint carbon can also form a $C_3$-$C_4$ cycle;

$R_7$ is selected from H, $C_1$-$C_4$alkyl or halo$C_1$-$C_4$alkyl;

$R_8$ is selected from H, $C_1$-$C_4$alkyl or halo$C_1$-$C_4$alkyl;

$R_{10}$ is selected from halogen, OH, amino, cyano, nitro, $C_1$-$C_4$alkyl, halo$C_1$-$C_4$alkyl, $C_1$-$C_4$alkoxy, halo$C_1$-$C_4$alkoxy, $C_3$-$C_4$cycloalkyl, $C_1$-$C_4$alkylamino, halo$C_1$-$C_4$alkylamino, di($C_1$-$C_4$alkyl)amino, halodi($C_1$-$C_4$alkyl)amino, C(=O)N$R_{11}R_{12}$, $C_1$-$C_4$alkylthio, halo$C_1$-$C_4$alkylthio, $C_2$-$C_4$alkenyl, $C_2$-$C_4$alkynyl, $C_2$-$C_4$alkenoxy, halo$C_2$-$C_4$alkenoxy, $C_2$-$C_4$alkynoxy, halo$C_2$-$C_4$alkynoxy, $C_1$-$C_4$alkylsulfonyl, halo$C_1$-$C_4$alkylsulfonyl, $C_1$-$C_4$alkylcarbonyl, halo$C_1$-$C_4$alkylcarbonyl, $C_1$-$C_4$alkoxycarbonyl, halo$C_1$-$C_4$alkoxycarbonyl, $C_1$-$C_4$alkoxy$C_1$-$C_{12}$alkyl, halo$C_1$-$C_4$alkoxy$C_1$-$C_4$alkyl, $C_1$-$C_4$alkylthio$C_1$-$C_4$alkyl, halo$C_1$-$C_4$alkylthio$C_1$-$C_4$alkyl, $C_1$-$C_4$alkoxycarbonyl$C_1$-$C_4$alkyl, halo$C_1$-$C_4$alkoxycarbonyl$C_1$-$C_4$alkyl, $C_1$-$C_4$alkylthiocarbonyl$C_1$-$C_4$alkyl, halo$C_1$-$C_4$alkylthiocarbonyl$C_1$-$C_4$alkyl, $C_1$-$C_4$alkylcarbonyloxy, halo$C_1$-$C_4$alkylcarbonyloxy, $C_1$-$C_4$alkoxycarbonyloxy, halo$C_1$-$C_4$alkoxycarbonyloxy, $C_1$-$C_4$alkylsulfonyloxy, halo$C_1$-$C_4$alkylsulfonyloxy, $C_1$-$C_4$alkoxy$C_1$-$C_4$alkoxy or halo$C_1$-$C_4$alkoxy$C_1$-$C_4$alkoxy;

The integer n is selected from 0 to 5, when n is 0, the benzene ring is unsubstituted phenyl; when n is more than 1, $R_{10}$ may be the same or different;

$R_{11}$, $R_{12}$ may be the same or different, selected respectively from H, $C_1$-$C_4$alkyl or halo$C_1$-$C_4$alkyl;

$R_{14}$ is selected from $C_1$-$C_4$alkyl, $C_3$-$C_4$cycloalkyl, halo$C_1$-$C_4$alkyl, $C_1$-$C_4$alkylcarbonyl, halo$C_1$-$C_4$alkylcarbonyl, $C_1$-$C_4$alkylsulfonyl, halo$C_1$-$C_4$alkylsulfonyl, $C_1$-$C_4$alkoxycarbonyl, $C_1$-$C_4$alkoxy$C_1$-$C_4$alkyl or $C_1$-$C_4$alkoxycarbonyl$C_1$-$C_4$alkyl;

$R_{15}$, $R_{16}$, $R_{17}$, $R_{18}$ may be the same or different, selected respectively from H, halogen, cyano, nitro, $C_1$-$C_4$alkyl, halo$C_1$-$C_4$alkyl, $C_1$-$C_4$alkoxy or halo$C_1$-$C_4$alkoxy;

$R_{19}$, $R_{20}$ may be the same or different, selected respectively from H, halogen, OH, cyano, nitro, $C_1$-$C_4$alkyl, halo$C_1$-$C_4$alkyl, $C_1$-$C_4$alkoxy, halo$C_1$-$C_4$alkoxy, $C_1$-$C_4$alkylthio, halo$C_1$-$C_4$ alkylthio, $C_3$-$C_4$cycloalkyl, unsubstituted or further substituted (hetero)aryl, (hetero)arylmethyl, (hetero)arylcarbonyl, (hetero)arylmethylcarbonyl or (hetero) alkyloxycarbonyl by 1 to 5 $R_{10}$;

$R_{21}$, $R_{22}$, $R_{23}$, $R_{24}$ may be the same or different, selected respectively from H, halogen, $C_1$-$C_4$alkyl, halo$C_1$-$C_4$alkyl, $C_1$-$C_4$alkoxy or halo$C_1$-$C_4$alkoxy;

$R_{25}$, $R_{26}$ may be the same or different, selected respectively from H, halogen, $C_1$-$C_4$alkyl, halo$C_1$-$C_4$alkyl, $C_1$-$C_4$alkoxy, halo$C_1$-$C_4$alkoxy, $C_1$-$C_4$alkylthio, halo$C_1$-$C_4$alkylthio, $C_3$-$C_4$cycloalkyl, unsubstituted or further substituted (hetero)aryl, (hetero)arylmethyl, (hetero)arylcarbonyl, (hetero)arylmethylcarbonyl or (hetero) alkyloxycarbonyl by 1 to 5 $R_{10}$;

Or the salts formed from the compounds represented by general formula IA, IB, IC, ID, IE or IF with hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid or citric acid.

In the general formula I, the more preferred compounds represented by general formula IA, IB, IC, ID, IE or IF of this invention are:

$R_1$ is selected from F, Cl, Br, $CH_3$, $C_2H_5$, n-$C_3H_7$, i-$C_3H_7$, n-$C_4H_9$, s-$C_4H_9$, i-$C_4H_9$, t-$C_4H_9$, cyclopropyl, cyclobutyl, $CH_2F$, $CH_2Cl$, $CHF_2$, $CF_3$, $CH_2CF_3$, $CH_2OCH_3$, $CH_2OCH_2CH_3$ or $CH_2OCH_2CF_3$;

$R_2$ is selected from F, Cl, Br, cyano, nitro, $CH_3$, $C_2H_5$, $OCH_3$, $OC_2H_5$ or $OCH_2CF_3$;

$R_3$ is selected from H, Cl, Br, $CH_3$, $C_2H_5$, n-$C_3H_7$, i-$C_3H_7$, n-$C_4H_9$, s-$C_4H_9$, i-$C_4H_9$, t-$C_4H_9$, $CH_2F$, $CH_2Cl$, $CHF_2$, $CF_3$, $CH_2CF_3$, $OCH_3$, $OCH_2CH_3$, $SCH_3$, $SCH_2CH_3$, $SO_2CH_3$ or $SO_2CH_2CH_3$;

$R_4$ is selected from H, OH, H(C)=O, $COC_2H_5$, $CH_3$, $C_2H_5$, $SO_2CH_3$ or $SO_2CH_2CH_3$;

$R_5$, $R_6$ may be the same or different, selected respectively from H, F, Cl, Br, I, $CH_3$, $C_2H_5$, n-$C_3H_7$, i-$C_3H_7$, n-$C_4H_9$, s-$C_4H_9$, i-$C_4H_9$, t-$C_4H_9$, $OCH_3$, $OCH_2CH_3$, n-$C_3H_7O$, i-$C_3H_7O$, n-$C_4H_9O$, s-$C_4H_9O$, i-$C_4H_9O$ or t-$C_4H_9O$;

$R_7$ is selected from H, $CH_3$, $C_2H_5$ or $CF_3$;

$R_8$ is selected from H, $CH_3$, $C_2H_5$ or $CF_3$;

$R_{10}$ is selected from F, Cl, Br, I, CN, $NH_2$, $NO_2$, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, $OCH_3$, $OCH_2CH_3$, n-$C_3H_7O$, i-$C_3H_7O$, n-$C_4H_9O$, s-$C_4H_9O$, i-$C_4H_9O$, t-$C_4H_9O$, $OCF_3$, $OCH_2CF_3$, $COOCH_3$, $COOCH_2CH_3$, $CONH_2$, $CONHCH_3$, $CONHC_2H_5$ or $CON(CH_3)_2$;

The integer n is selected from 0 to 5, when n is 0, the benzene ring is unsubstituted phenyl; when n is more than 1, $R_{10}$ may be the same or different;

$R_{14}$ is selected from $CH_3$, $C_2H_5$, n-$C_3H_7$, i-$C_3H_7$, n-$C_4H_9$, s-$C_4H_9$, i-$C_4H_9$, t-$C_4H_9$, cyclopropyl, cyclobutyl, $CH_2F$, $CH_2Cl$, $CHF_2$, $CF_3$ or $CH_2CF_3$;

$R_{15}$, $R_{16}$, $R_{17}$, $R_{18}$ may be the same or different, selected respectively from H, Cl, CN, $NO_2$, $CH_3$, $CF_3$, $OCH_3$ or $OCF_3$;

$R_{19}$, $R_{20}$ may be the same or different, selected respectively from H, F, Cl, Br, OH, CN, $NO_2$, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, $CH_2CF_3$, $OCH_3$, $OCH_2CH_3$, n-$C_3H_7O$, i-$C_3H_7O$, n-$C_4H_9O$, s-$C_4H_9O$, i-$C_4H_9O$, t-$C_4H_9O$, $OCF_3$, $OCH_2CF_3$, unsubstituted or further substituted (hetero)aryl, (hetero)arylmethyl, (hetero)arylcarbonyl, (hetero)arylmethylcarbonyl or (hetero)alkyloxycarbonyl by 1 to 5 $R_{10}$;

$R_{21}$, $R_{22}$, $R_{23}$, $R_{24}$ may be the same or different, selected respectively from H, F, Cl, Br, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, $CH_2CF_3$, $OCH_3$, $OCH_2CH_3$, n-$C_3H_7O$, i-$C_3H_7O$, n-$C_4H_9O$, s-$C_4H_9O$, i-$C_4H_9O$, t-$C_4H_9O$, $OCF_3$ or $OCH_2CF_3$;

$R_{25}$, $R_{26}$ may be the same or different, selected respectively from H, F, Cl, Br, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, $CH_2CF_3$, $OCH_3$, $OCH_2CH_3$, n-$C_3H_7O$, i-$C_3H_7O$, n-$C_4H_9O$, s-$C_4H_9O$, i-$C_4H_9O$, t-$C_4H_9O$, $OCF_3$, $OCH_2CF_3$, unsubstituted or further substituted (hetero)aryl, (hetero)arylmethyl, (hetero)arylcarbonyl, (hetero)arylmethylcarbonyl or (hetero)alkyloxycarbonyl by 1 to 5 $R_{10}$;

Or the salts formed from the compounds represented by general formula IA, IB, IC, ID, IE or IF with hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid or maleic acid.

In the general formula I, the more preferred compounds represented by general formula IA, IB, IC, ID, IE or IF of this invention are:

$R_1$ is selected from F, Cl, Br, $CH_3$, $C_2H_5$, cyclopropyl, cyclobutyl, $CH_2F$, $CH_2Cl$, $CHF_2$, $CF_3$ or $CH_2CF_3$;

$R_2$ is selected from F, Cl, Br, cyano, nitro, $CH_3$, $C_2H_5$, $OCH_3$ or $OC_2H_5$;

$R_3$ is selected from H, Cl, Br, $CH_3$, $C_2H_5$, i-$C_3H_7$, $CF_3$, $OCH_3$, $OCH_2CH_3$, $SCH_3$, $SCH_2CH_3$, $SO_2CH_3$ or $SO_2CH_2CH_3$;

$R_4$ is selected from H, OH, H(C)=O, $COC_2H_5$, $CH_3$, $C_2H_5$, $SO_2CH_3$ or $SO_2CH_2CH_3$;

$R_5$, $R_6$ may be the same or different, selected respectively from H, F, Cl, Br, I, $CH_3$, $C_2H_5$, $OCH_3$ or $OCH_2CH_3$;

$R_7$ is selected from H, $CH_3$, $C_2H_5$ or $CF_3$;

$R_8$ is selected from H, $CH_3$, $C_2H_5$ or $CF_3$;

$R_{10}$ is selected from F, Cl, Br, I, CN, $NH_2$, $NO_2$, $CH_3$, $C_2H_5$, i-$C_3H_7$, t-$C_4H_9$, $CF_3$, $CCl_3$, $OCH_3$, $OCH_2CH_3$, $OCF_3$ or $OCH_2CF_3$;

The integer n is selected from 0 to 5, when n is 0, the benzene ring is unsubstituted phenyl; when n is more than 1, $R_{10}$ may be the same or different;

$R_{14}$ is selected from $CH_3$, $C_2H_5$, n-$C_3H_7$, i-$C_3H_7$, n-$C_4H_9$, s-$C_4H_9$, i-$C_4H_9$, t-$C_4H_9$, cyclopropyl, cyclobutyl, $CH_2F$, $CH_2Cl$, $CHF_2$, $CF_3$ or $CH_2CF_3$;

$R_{15}$, $R_{16}$, $R_{17}$, $R_{18}$ may be the same or different, selected respectively from H, Cl, CN, $NO_2$, $CH_3$, $CF_3$, $OCH_3$ or $OCF_3$;

$R_{19}$, $R_{20}$ may be the same or different, selected respectively from H, F, Cl, Br, OH, CN, $NO_2$, $CH_3$, $C_2H_5$, i-$C_3H_7$, t-$C_4H_9$, $CF_3$, $CH_2CF_3$, $OCH_3$, $OCH_2CH_3$, $OCF_3$ or $OCH_2CF_3$;

$R_{21}$, $R_{22}$, $R_{23}$, $R_{24}$ may be the same or different, selected respectively from H, F, Cl, Br, $CH_3$, $C_2H_5$, $CF_3$, $CH_2CF_3$, $OCH_3$, $OCH_2CH_3$, $OCF_3$ or $OCH_2CF_3$;

$R_{25}$, $R_{26}$ may be the same or different, selected respectively from H, F, Cl, Br, $CH_3$, $C_2H_5$, i-$C_3H_7$, t-$C_4H_9$, $CF_3$, $CH_2CF_3$, $OCH_3$, $OCH_2CH_3$, $OCF_3$, $OCH_2CF_3$, unsubstituted or further substituted (hetero)aryl, (hetero)arylmethyl, (hetero)arylcarbonyl, (hetero)arylmethylcarbonyl or (hetero)alkyloxycarbonyl by 1 to 5 $R_{10}$;

Or the salts formed from the compounds represented by general formula IA, IB, IC, ID, IE or IF with hydrochloric acid, sulfuric acid, phosphoric acid, formic acid, acetic acid, trifluoroacetic acid, oxalic acid, methylsulfonic acid, p-toluenesulfonic acid or benzoic acid.

In the general formula I, the more preferred compounds represented by general formula IB, IC or ID of this invention are:

$R_1$ is selected from $CH_3$, $C_2H_5$, $CHF_2$, $CF_3$ or $CH_2CF_3$;

$R_2$ is selected from F, Cl, Br, cyano or nitro;

$R_3$ is selected from H, Cl, $CH_3$, $CF_3$, $OCH_3$, $SCH_3$ or $SO_2CH_3$;

$R_4$ is selected from H, H(C)=O, $COC_2H_5$, $CH_3$, $C_2H_5$ or $SO_2CH_3$;

$R_5$, $R_6$ may be the same or different, selected respectively from H or $CH_3$;

$R_7$ is selected from H, $CH_3$, $C_2H_5$ or $CF_3$;

$R_8$ is selected from H, $CH_3$, $C_2H_5$ or $CF_3$;

$R_{10}$ is selected from F, Cl, Br, I, CN, $NO_2$, $CH_3$, $C_2H_5$, $CF_3$, $OCH_3$ or $OCF_3$;

The integer n is selected from 0 to 5, when n is 0, the benzene ring is unsubstituted phenyl; when n is more than 1, $R_{10}$ may be the same or different;

$R_{15}$, $R_{16}$, $R_{17}$, $R_{18}$ may be the same or different, selected respectively from H, Cl, CN, $NO_2$, $CH_3$ or $CF_3$;

$R_{19}$, $R_{20}$ is selected from H;

Or the salts formed from the compounds represented by general formula IB, IC or ID with hydrochloric acid or sulfuric acid.

In the general formula I, the more preferred compounds represented by general formula IB, IC or ID of this invention are:

$R_1$ is selected from $CH_3$, $C_2H_5$, $CHF_2$ or $CF_3$;

$R_2$ is selected from Cl;

$R_3$ is selected from H or $CH_3$;

$R_4$, $R_5$, $R_6$, $R_7$, $R_8$ is selected from H;

$R_{10}$ is selected from F, Cl, $CH_3$, $CF_3$, $OCH_3$ or $OCF_3$;

The integer n is selected from 0 to 5, when n is 0, the benzene ring is unsubstituted phenyl; when n is more than 1, $R_{10}$ may be the same or different;

$R_{15}$, $R_{16}$, $R_{17}$, $R_{18}$ may be the same or different, selected respectively from H or Cl;

$R_{19}$, $R_{20}$ is selected from H;

Or the salts formed from the compounds represented by general formula IB, IC or ID with hydrochloric acid.

In the general formula I, further more, the preferred compounds represented by general formula IB of this invention are:

$R_1$ is selected from $CH_3$, $C_2H_5$ or $CHF_2$;

$R_2$ is selected from Cl;

$R_3$ is selected from H or $CH_3$;

$R_4$, $R_5$, $R_6$, $R_7$, $R_8$ is selected from H;

$R_{10}$ is selected from F, Cl, $CH_3$, $CF_3$, $OCH_3$ or $OCF_3$;

The integer n is selected from 1 to 5, when n is more than 1, $R_{10}$ may be the same or different;

In the general formula I, even more preferred compounds represented by general formula IB of this invention are:

$R_1$ is selected from $CH_3$, $C_2H_5$ or $CHF_2$;

$R_2$ is selected from Cl;

$R_3$ is selected from H or $CH_3$;

$R_4$, $R_5$, $R_6$, $R_7$, $R_8$ is selected from H;

$(R_{10})n$ is selected from 4-F, 4-Cl, 2,4-2Cl or 4-$OCF_3$.

The terms used above to define the compounds of general formula I represent substitutes are as follows:

The "halogen" or "halo" is fluorine, chlorine, bromine or iodine.

The "alkyl" stands for straight or branched chain alkyl, such as methyl, ethyl, propyl, isopropyl, n-butyl or t-butyl.

The "cycloalkyl" is substituted or unsubstituted cyclic alkyl, such as cyclopropyl, cyclopentyl or cyclohexyl. The substitute(s) is(are) methyl, halogen, etc.

The "haloalkyl" stands for straight or branched chain alkyl, in which hydrogen atoms can be all or partly substituted with halogen, such as chloromethyl, dichloromethyl, trichloromethyl, fluoromethyl, difluoromethyl, trifluoromethyl, etc.

The "alkylsulfinyl" means a straight-chain or branched alkyl is linked to the structure by (—SO—), such as methylsulfinyl.

The "haloalkylsulfinyl" stands for a straight-chain or branched alkylsulfinyl, in which hydrogen atoms may be all or partly substituted with halogen.

The "haloalkylsulfonyl" stands for a straight-chain or branched alkylsulfonyl, in which hydrogen atoms may be all or partly substituted with halogen.

The "alkylaminothio" refers to —SNHCH$_3$, —SNHC$_2$H$_5$.

The "dialkylaminothio" refers to —SN(CH$_3$)$_2$, —SN(C$_2$H$_5$)$_2$.

The "alkylaminosulfonyl" refers to alkyl-NH—SO$_2$—.

The "dialkylaminosulfonyl" refers to (alkyl)$_2$-N—SO$_2$—.

The "alkylsulfonylaminocarbonyl" refers to alkyl-SO$_2$—NH—CO—.

The "alkylcarbonylaminosulfonyl" refers to alkyl-CO—NH—SO$_2$—.

The "alkylcarbonylalkyl" refers to alkyl-CO-alkyl-.

The "alkylsulfonyloxy" such as alkyl-S(O)$_2$—O—.

The "haloalkylsulfonyloxy" stands for a straight-chain or branched alkylsulfonyloxy, in which hydrogen atoms may be all or partly substituted with halogen, such as CF$_3$—SO$_2$—O—.

The "cycloalkyloxycarbonyl" means cyclopropyloxycarbonyl, cyclohexyloxycarbonyl, etc.

The "alkoxy" refers to straight or branched chain alkyl, which is linked to the structure by oxygen atom.

The "haloalkoxy" refers to straight or branched chain alkoxy, in which hydrogen atoms may be all or partly substituted with halogen, such as chloromethoxy, dichloromethoxy, trichloromethoxy, fluoromethoxy, difluoromethoxy, trifluoromethoxy, chlorofluoromethoxy, trifluoroethoxy, etc.

The "haloalkoxycarbonyl" refers to straight or branched chain alkoxycarbonyl, in which hydrogen atoms can be all or partly substituted with halogen, such as ClCH$_2$CH$_2$OCO—, CF$_3$CH$_2$OCO—, etc.

The "alkoxyalkyl" means alkyl-O-alkyl-, such as —CH$_2$OCH$_3$.

The "haloalkoxyalkyl" refers to alkoxyalkyl, in which hydrogen atoms may be all or partly substituted with halogen, such as —CH$_2$OCH$_2$CH$_2$Cl, —CH$_2$OCH$_2$CF$_3$, etc.

The "alkoxycarbonylalkyl" refers to alkoxycarbonylalkyl-, such as —CH$_2$COOCH$_3$.

The "haloalkoxycarbonylalkyl" refers to alkoxycarbonylalkyl, in which hydrogen atoms may be all or partly substituted with halogen, such as —CH$_2$COOCH$_2$CF$_3$.

The "alkylcarbonyloxy": such as —OCOCH$_3$, etc.

The "haloalkylcarbonyloxy" refers to alkylcarbonyloxy, in which hydrogen atoms may be all or partly substituted with halogen, such as —OCOCF$_3$, etc.

The "alkoxycarbonyloxy" refers to alkoxycarbonyl-oxy, such as —OCOOCH$_3$.

The "haloalkoxycarbonyloxy" refers to alkoxycarbonyloxy, in which hydrogen atoms may be all or partly substituted with halogen, such as —OCOOCF$_3$.

The "alkylthiocarbonylalkyl" refers to alkylthiocarbonylalkyl-, such as —CH$_2$COSCH$_3$.

The "haloalkylthiocarbonylalkyl" refers to alkylthiocarbonylalkyl, in which hydrogen atoms may be all or partly substituted with halogen, such as —CH$_2$COSCH$_2$CF$_3$.

The "alkoxyalkoxy" stands for —OCH$_2$OCH$_3$, etc.

The "haloalkoxyalkoxy" refers to alkoxyalkoxy, in which hydrogen atoms may be all or partly substituted with halogen, such as —OCH$_2$OCF$_3$.

The "alkoxyalkoxycarbonyl": such as —COOCH$_2$CH$_2$OCH$_3$, etc.

The "alkylthio" refers to straight or branched chain alkyl, which is linked to the structure by sulfur atom.

The "haloalkylthio" refers to straight or branched chain alkylthio, in which hydrogen atoms may be all or partly substituted with halogen, such as chloromethylthio, dichloromethylthio, trichloromethylthio, fluoromethylthio, difluoromethylthio, trifluoromethylthio, chlorofluoromethylthio, etc.

The "alkylthioalkyl" means alkyl-S-alkyl-, such as —CH$_2$SCH$_3$.

The "haloalkylthioalkyl" refers to alkylthioalkyl, in which hydrogen atoms may be all or partly substituted with halogen, such as —CH$_2$SCH$_2$CH$_2$Cl, —CH$_2$SCH$_2$CF$_3$.

The "alkylamino" refers to straight or branched chain alkyl, which is linked to the structure by nitrogen atom.

The "haloalkylamino" refers to straight or branched chain alkylamino, in which hydrogen atoms may be all or partly substituted with halogen.

The "dialkylamino": such as —N(CH$_3$)$_2$, —N(CH$_3$CH$_2$)$_2$.

The "dihaloalkylamino" refers to dialkylamino, in which hydrogen atoms may be all or partly substituted with halogen, such as —N(CF$_3$)$_2$, —N(CH$_2$CF$_3$)$_2$.

The "alkenyl" refers to straight or branched chain alkenyl, such as ethenyl, 1-propenyl, 2-propenyl and different isomer of butenyl, pentenyl and hexenyl. Alkenyl also includes polyene, such as propa-1,2-dienyl and hexa-2,4-dienyl.

The "haloalkenyl" stands for straight or branched chain alkenyl, in which hydrogen atoms may be all or partly substituted with halogen.

The "alkenoxyl" refers to straight or branched chain alkenyl which is linked to the structure by oxygen.

The "haloalkenoxyl" stands for a straight-chain or branched alkenoxyl, in which hydrogen atoms may be all or partly substituted with halogen.

The "alkenylthio" refers to straight or branched chain alkenyl, which is linked to the structure by sulfur atom. Such as —SCH$_2$CH=CH$_2$.

The "alkenoxylcarbonyl" means CH$_2$=CHCH$_2$OCO—, etc.

The "alkynyl" refers to straight or branched chain alkynyl, such as ethynyl, 1-propynyl, 2-propynyl and different isomer of butynyl, pentynyl and hexynyl. Alkynyl also includes groups including more than one triple bonds, such as hexa-2,5-diynyl.

The "haloalkynyl" stands for straight or branched chain alkynyl, in which hydrogen atoms may be all or partly substituted with halogen.

The "alkynoxyl" refers to straight or branched chain alkynes which is linked to the structure by oxygen.

The "haloalkynoxyl" stands for a straight-chain or branched alkynoxyl, in which hydrogen atoms may be all or partly substituted with halogen.

The "alkynoxylcarbonyl" means —COOCH$_2$C≡CH, etc.

The "alkylsulfonyl" means a straight-chain or branched alkyl which is linked to the structure by (—SO$_2$—), such as methylsulfonyl.

The "haloalkylsulfonyl" stands for a straight-chain or branched alkylsulfonyl, in which hydrogen atoms may be all or partly substituted with halogen.

The "alkylcarbonyl" means alkyl is linked to the structure by carbonyl, such as —COCH$_3$, —COCH$_2$CH$_3$.

The "haloalkylcarbonyl" stands for a straight-chain or branched alkylcarbonyl, in which hydrogen atoms may be all or partly substituted with halogen, such as —COCF$_3$.

The "alkoxycarbonyl" means alkoxy is linked to the structure by carbonyl, such as —COOCH$_3$, —COOCH$_2$CH$_3$.

The "aminocarbonyl": such as —CONH$_2$.

The "alkylaminocarbonyl" means alkyl-NH—CO—, such as —CONHCH$_3$, —CONHCH$_2$CH$_3$.

The "dialkylaminocarbonyl": such as —CON(CH$_3$)$_2$, —CON(CH$_2$CH$_3$)$_2$.

The "aryl" in (hetero)aryl, (hetero)arylalkyl, (hetero)arylcarbonyl, (Hetero) arylmethylcarbonyl, (hetero)arylcarbonylalkyl, (hetero)aryloxycarbonyl, (Hetero)arylalkyloxycarbonyl includes phenyl or naphthyl etc. The "heteroaryl" stands for five member ring or six member ring containing one or more N, O, S hetero atoms, such as furyl, pyrazolyl, thiazolyl, pyridinyl, pyrimidinyl, pyrazinyl, pyridazinyl, triazinyl, quinolinyl, etc.

"(Hetero)aryl" refers to phenyl, etc.

"(Hetero)arylalkyl" means benzyl, phenylethyl, 4-chlorobenzyl, 2-chloro-5-picolyl, 2-chloro-5-methylthiazole, etc.

"(Hetero)arylcarbonyl" refers to benzoyl, 4-Cl-benzoyl, etc.

"(Hetero) arylmethylcarbonyl" refers to PhCH$_2$CO—.

"(Hetero)arylcarbonylalkyl" refers to PhCOCH$_2$—.

"(Hetero)aryloxycarbonyl": such as phenoxycarbonyl, p-chlorophenoxycarbonyl, p-nitrophenoxycarbony, naphthyloxycarbonyl, etc. Arylalkyloxycarbonyl means benzyloxycarbonyl, p-chlorobenzyloxycarbonyl, p-trifluoromethylbenzyloxycarbonyl, etc.

"(Hetero)arylalkyloxycarbonyl" refers to —COOCH$_2$Ph, —COOCH$_2$-4-Cl-Ph, etc.

In the general formula I, part of preferred substituents of R$_1$, R$_2$, R$_3$, R$_4$, R$_5$(R$_6$), R$_7$, R$_8$ and R$_9$ are separately listed in table1, table2, table3, table4, table5, table6, table7 and table8, but without being restricted thereby.

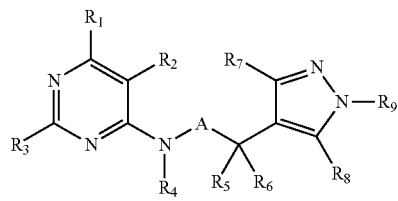

I

TABLE 1

| R$_1$ substituents | | | |
|---|---|---|---|
| R$_1$ | R$_1$ | R$_1$ | R$_1$ |
| H | CCl$_3$ | CH(CH$_3$)F | NHCOOCH$_3$ |
| F | CHF$_2$ | CH(CH$_3$)Cl | NHCOOC$_2$H$_5$ |
| Cl | CHBr$_2$ | CH(CH$_3$)Br | N(CH$_3$)NH$_2$ |
| Br | CF$_3$ | C(CH$_3$)$_2$F | NHN(CH$_3$)$_2$ |
| I | SCH$_3$ | COOCH$_3$ | CH$_2$OCH$_3$ |
| CH$_3$ | SOCH$_3$ | COOC$_2$H$_5$ | CH$_2$OCH$_2$CH$_3$ |
| C$_2$H$_5$ | SO$_2$CH$_3$ | CONH$_2$ | CH$_2$CH$_2$OCH$_3$ |
| n-C$_3$H$_7$ | COOH | CONHCH$_3$ | OCH$_2$CH=CH$_2$ |
| i-C$_3$H$_7$ | OCH$_3$ | CONHCN | OCH$_2$CH=CHCl |
| n-C$_4$H$_9$ | OC$_2$H$_5$ | CON(CH$_3$)$_2$ | OCH$_2$C≡CCH$_3$ |
| i-C$_4$H$_9$ | OCF$_3$ | NHCH$_2$CN | CONHCH$_2$CN |
| t-C$_4$H$_9$ | NH$_2$ | OSO$_2$CH$_3$ | CH$_2$CH$_2$OCH$_2$CH$_3$ |
| cyclopropyl | NHCH$_3$ | OCH$_2$C≡CH | CH(CH$_3$)SCH$_3$ |
| | NHC$_2$H$_5$ | OCH$_2$C≡C—I | CH(CH$_3$)SOCH$_3$ |
| cyclopentyl | N(CH$_3$)$_2$ | NHOCH$_3$ | CH(CH$_3$)SO$_2$CH$_3$ |
| | N(C$_2$H$_5$)$_2$ | NHOC$_2$H$_5$ | CH(CH$_3$)OH |
| cyclohexyl | CHCl$_2$ | NHCOCH$_3$ | CH(CH$_3$)OCOCH$_3$ |
| | CH$_2$Cl | NHCOC$_2$H$_5$ | CH$_2$OCH$_2$CF$_3$ |

TABLE 2

| R$_2$ substituents | | | |
|---|---|---|---|
| R$_2$ | R$_2$ | R$_2$ | R$_2$ |
| H | NO$_2$ | t-C$_4$H$_9$ | OC$_4$H$_9$-i |
| F | CH$_3$ | OCH$_3$ | OC$_4$H$_9$-t |
| Cl | C$_2$H$_5$ | OC$_2$H$_5$ | OCH$_2$F |
| Br | n-C$_3$H$_7$ | OC$_3$H$_7$-n | OCHF$_2$ |
| I | i-C$_3$H$_7$ | OC$_3$H$_7$-i | OCF$_3$ |
| CN | n-C$_4$H$_9$ | OC$_4$H$_9$-n | OCH$_2$CF$_3$ |

TABLE 3

| R$_3$ substituents | | | | |
|---|---|---|---|---|
| R$_3$ | R$_3$ | R$_3$ | R$_3$ | R$_3$ |
| H | i-C$_3$H$_7$ | CHF$_2$ | OCH$_3$ | SCH$_3$ |
| F | n-C$_4$H$_9$ | CHBr$_2$ | OC$_2$H$_5$ | SC$_2$H$_5$ |
| Cl | i-C$_4$H$_9$ | CF$_3$ | OC$_3$H$_7$-n | SC$_3$H$_7$-n |
| Br | CH$_3$ | CH(CH3)F | OC$_3$H$_7$-i | SC$_3$H$_7$-i |
| I | C$_2$H$_5$ | CH(CH$_3$)Cl | OC$_4$H$_9$-n | SCH$_4$H$_9$-i |

TABLE 3-continued

R₃ substituents

| R₃ | R₃ | R₃ | R₃ | R₃ |
|---|---|---|---|---|
| (cyclopropyl) | CHCl₂ | CH(CH₃)Br | OC₄H₉-i | SC₄H₉-i |
|  | CCl₃ | CH(n-C₄H₉)F | OC₄H₉-t | SC₄H₉-t |
| (cyclopentyl) | (cyclohexyl) | C(CH₃)₂F | OCF₃ | SO₂CH₃ |
|  |  | n-C₃H₇ | OCH₂CF₃ | t-C₄H₉ |

TABLE 4

R₄ substituents

| R₄ | R₄ | R₄ | R₄ |
|---|---|---|---|
| H | OH | CH₃ | C₂H₅ |
| n-C₃H₇ | i-C₃H₇ | n-C₄H₉ | s-C₄H₉ |
| i-C₄H₉ | t-C₄H₉ | HCO | CH₃CO |
| CH₃CH₂CO | n-C₃H₇CO | i-C₃H₇CO | CH₃SO₂ |
| CH₃CH₂SO₂ | n-C₃H₇SO₂ | n-C₄H₉SO₂ |  |

TABLE 5

R₅(R₆) substituents

| R₅(R₆) | R₅(R₆) | R₅(R₆) | R₅(R₆) |
|---|---|---|---|
| H | CH₃ | C₂H₅ | n-C₃H₇ |
| i-C₃H₇ | n-C₄H₉ | s-C₄H₉ | i-C₄H₉ |
| t-C₄H₉ | (cyclopropyl) | (cyclopentyl) | (cyclohexyl) |

CR₅R₆

| (cyclopropyl) | (cyclopentyl) | (cyclohexyl) |
|---|---|---|

TABLE 6

R₇ substituents

| R₇ | R₇ | R₇ | R₇ |
|---|---|---|---|
| H | CH₃ | C₂H₅ | n-C₃H₇ |
| i-C₃H₇ | CH₂F | CHF₂ | CF₃ |
| CH₂CF₃ | CF₂CF₃ | Ph | Ph-4-Cl |

TABLE 7

R₈ substituents

| R₈ | R₈ | R₈ | R₈ |
|---|---|---|---|
| H | CH₃ | C₂H₅ | n-C₃H₇ |
| i-C₃H₇ | CH₂F | CHF₂ | CF₃ |
| CH₂CF₃ | CF₂CF₃ | Ph | Ph-4-Cl |

TABLE 8

R9 substituents

| R9 | R9 | R9 | R9 | R9 |
|---|---|---|---|---|
| CH$_3$ | Et | n-Pr | i-Pr | n-Bu |
| i-Bu | s-Bu | t-Bu | CH$_2$F | CHF$_2$ |
| CF$_3$ | CH$_2$CF$_3$ | COCH$_3$ | COEt | CO-n-Pr |
| CO-n-Bu | CO-t-Bu | COCF$_3$ | CO$_2$CH$_3$ | CO$_2$Et |
| CO$_2$-n-Pr | CO$_2$-i-Pr | CH$_2$-t-Bu | CO$_2$CH$_2$CF$_3$ | CH$_2$OCH$_3$ |

TABLE 8-continued

R9 substituents (structures shown)

In the general formula I, part of the present invention compounds are also explained by the following compounds listed in Table 9 to Table 111, but without being restricted thereby. In the general formula IA, IB, IC, ID, IE or IF, $R_7=R_8=R_{19}=R_{20}=H$.

In general formula IA,

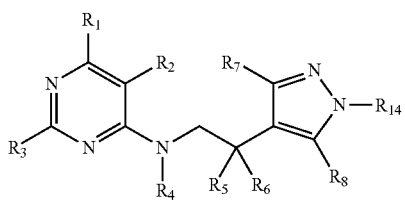

IA $R_1=CH_3$, $R_2=Cl$, $R_3=R_4=R_5=R_6=H$, the substituents $R_{14}$ refer to Table 9, the representative compounds are coded as 1-15.

TABLE 9

| No. | $R_{14}$ |
|---|---|
| 1 | $CH_3$ |
| 2 | $C_2H_5$ |
| 3 | $n\text{-}C_3H_7$ |
| 4 | $i\text{-}C_3H_7$ |
| 5 | $n\text{-}C_4H_9$ |

TABLE 9-continued

| No. | $R_{14}$ |
|---|---|
| 6 | $s\text{-}C_4H_9$ |
| 7 | $i\text{-}C_4H_9$ |
| 8 | $t\text{-}C_4H_9$ |
| 9 | $CF_3$ |
| 10 | $CH_2CF_3$ |
| 11 | $CF_2CF_3$ |
| 12 | (cyclopropyl) |
| 13 | (cyclobutyl) |
| 14 | (cyclopentyl) |
| 15 | (cyclohexyl) |

Table 10: in general formula IA, $R_1=C_2H_5$, $R_2=Cl$, $R_3=R_4=R_5=R_6=H$, the substituents $R_{14}$ are consistent with those in Table 9 and corresponding to 1-15 in table 9 in turn, the representative compounds are coded as 16-30.

Table 11: in general formula IA, $R_1$=CHF$_2$, $R_2$=Cl, $R_3$=$R_4$=$R_5$=$R_6$=H, the substituents $R_{14}$ are consistent with those in Table 9 and corresponding to 1-15 in table 9 in turn, the representative compounds are coded as 31-45.

Table 12: in general formula IA, $R_1$=CF$_3$, $R_2$=Cl, $R_3$=$R_4$=$R_5$=$R_6$=H, the substituents $R_{14}$ are consistent with those in Table 9 and corresponding to 1-15 in table 9 in turn, the representative compounds are coded as 46-60.

Table 13: in general formula IA, $R_1$=CH$_3$, $R_2$=Cl, $R_3$=CH$_3$, $R_4$=$R_5$=$R_6$=H, the substituents $R_{14}$ are consistent with those in Table 9 and corresponding to 1-15 in table 9 in turn, the representative compounds are coded as 61-75.

Table 14: in general formula IA, $R_1$=C$_2$H$_5$, $R_2$=Cl, $R_3$=CH$_3$, $R_4$=$R_5$=$R_6$=H, the substituents $R_{14}$ are consistent with those in Table 9 and corresponding to 1-15 in table 9 in turn, the representative compounds are coded as 76-90.

Table 15: in general formula IA, $R_1$=CHF$_2$, $R_2$=Cl, $R_3$=CH$_3$, $R_4$=$R_5$=$R_6$=H, the substituents $R_{14}$ are consistent with those in Table 9 and corresponding to 1-15 in table 9 in turn, the representative compounds are coded as 91-105.

Table 16: in general formula IA, $R_1$=CF$_3$, $R_2$=Cl, $R_3$=CH$_3$, $R_4$=$R_5$=$R_6$=H, the substituents $R_{14}$ are consistent with those in Table 9 and corresponding to 1-15 in table 9 in turn, the representative compounds are coded as 106-120.

Table 17: in general formula IA, $R_1$=CH$_3$, $R_2$=Cl, $R_3$=$R_4$=$R_5$=H, $R_6$=CH$_3$, the substituents $R_{14}$ are consistent with those in Table 9 and corresponding to 1-15 in table 9 in turn, the representative compounds are coded as 121-135.

Table 18: in general formula IA, $R_1$=C$_2$H$_5$, $R_2$=Cl, $R_3$=$R_4$=$R_5$=H, $R_6$=CH$_3$, the substituents $R_{14}$ are consistent with those in Table 9 and corresponding to 1-15 in table 9 in turn, the representative compounds are coded as 136-150.

Table 19: in general formula IA, $R_1$=CHF$_2$, $R_2$=Cl, $R_3$=$R_4$=$R_5$=H, $R_6$=CH$_3$, the substituents $R_{14}$ are consistent with those in Table 9 and corresponding to 1-15 in table 9 in turn, the representative compounds are coded as 151-165.

Table 20: in general formula IA, $R_1$=CF$_3$, $R_2$=Cl, $R_3$=$R_4$=$R_5$=H, $R_6$=CH$_3$, the substituents $R_{14}$ are consistent with those in Table 9 and corresponding to 1-15 in table 9 in turn, the representative compounds are coded as 166-180.

Table 21: in general formula IA, $R_1$=CH$_3$, $R_2$=Cl, $R_3$=CH$_3$, $R_4$=$R_5$=H, $R_6$=CH$_3$, the substituents $R_{14}$ are consistent with those in Table 9 and corresponding to 1-15 in table 9 in turn, the representative compounds are coded as 181-195.

Table 22: in general formula IA, $R_1$=C$_2$H$_5$, $R_2$=Cl, $R_3$=CH$_3$, $R_4$=$R_5$=H, $R_6$=CH$_3$, the substituents $R_{14}$ are consistent with those in Table 9 and corresponding to 1-15 in table 9 in turn, the representative compounds are coded as 196-210.

Table 23: in general formula IA, $R_1$=CHF$_2$, $R_2$=Cl, $R_3$=CH$_3$, $R_4$=$R_5$=H, $R_6$=CH$_3$, the substituents $R_{14}$ are consistent with those in Table 9 and corresponding to 1-15 in table 9 in turn, the representative compounds are coded as 211-225.

Table 24: in general formula IA, $R_1$=CF$_3$, $R_2$=Cl, $R_3$=CH$_3$, $R_4$=$R_5$=H, $R_6$=CH$_3$, the substituents $R_{14}$ are consistent with those in Table 9 and corresponding to 1-15 in table 9 in turn, the representative compounds are coded as 226-240.

In general formula IB,

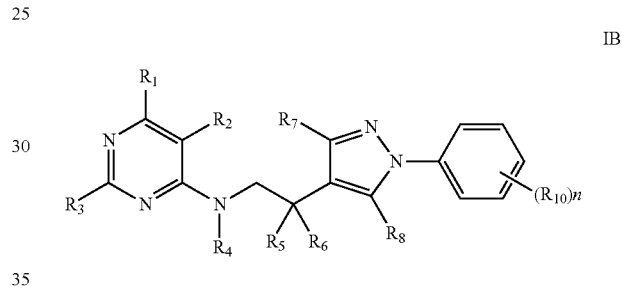

IB $R_1$=CH$_3$, $R_2$=Cl, $R_3$=$R_4$=$R_5$=$R_6$=H, the substituents $(R_{10})n$ refer to Table 25, the representative compounds are coded as 241-518.

TABLE 25

| No. | $(R_{10})n$ | No. | $(R_{10})n$ | No. | $(R_{10})n$ |
|---|---|---|---|---|---|
| 241 | H | 242 | 2-F | 243 | 3-F |
| 244 | 4-F | 245 | 2,3-2F | 246 | 2,4-2F |
| 247 | 2,5-2F | 248 | 2,6-2F | 249 | 3,4-2F |
| 250 | 3,5-2F | 251 | 2,3,4-3F | 252 | 2,3,5-3F |
| 253 | 2,4,5-3F | 254 | 2,3,6-3F | 255 | 2,4,6-3F |
| 256 | 3,4,5-3F | 257 | 2-Cl | 258 | 3-Cl |
| 259 | 4-Cl | 260 | 2,3-2Cl | 261 | 2,4-2Cl |
| 262 | 2,5-2Cl | 263 | 2,6-2Cl | 264 | 3,4-2Cl |
| 265 | 3,5-2Cl | 266 | 2,3,4-3Cl | 267 | 2,3,5-3Cl |
| 268 | 2,4,5-3Cl | 269 | 2,3,6-3Cl | 270 | 2,4,6-3Cl |
| 271 | 3,4,5-3Cl | 272 | 2-Br | 273 | 3-Br |
| 274 | 4-Br | 275 | 2,3-Br | 276 | 2,4-2Br |
| 277 | 2,5-2Br | 278 | 2,6-2Br | 279 | 3,4-2Br |
| 280 | 3,5-2Br | 281 | 2,3,4-3Br | 282 | 2,3,5-3Br |
| 283 | 2,4,5-3Br | 284 | 2,3,6-3Br | 285 | 2,4,6-3Br |
| 286 | 3,4,5-3Br | 287 | 2-CN | 288 | 3-CN |
| 289 | 4-CN | 290 | 2-NO$_2$ | 291 | 3-NO$_2$ |
| 292 | 4-NO$_2$ | 293 | 2,4-2NO$_2$ | 294 | 2,4,6-3NO$_2$ |
| 295 | 2-CH$_3$ | 296 | 3-CH$_3$ | 297 | 4-CH$_3$ |
| 298 | 2,3-2CH$_3$ | 299 | 2,4-2CH$_3$ | 300 | 2,5-2CH$_3$ |
| 301 | 2,6-2CH$_3$ | 302 | 3,4-2CH$_3$ | 303 | 3,5-2CH$_3$ |
| 304 | 2-C$_2$H$_5$ | 305 | 3-C$_2$H$_5$ | 306 | 4-C$_2$H$_5$ |
| 307 | 2-CF$_3$ | 308 | 3-CF$_3$ | 309 | 4-CF$_3$ |
| 310 | 2-OCH$_3$ | 311 | 3-OCH$_3$ | 312 | 4-OCH$_3$ |
| 313 | 2-SCH$_3$ | 314 | 3-SCH$_3$ | 315 | 4-SCH$_3$ |
| 316 | 2-OCF$_3$ | 317 | 3-OCF$_3$ | 318 | 4-OCF$_3$ |
| 319 | 2-SCF$_3$ | 320 | 3-SCF$_3$ | 321 | 4-SCF$_3$ |
| 322 | 2-OC$_2$H$_5$ | 323 | 3-OC$_2$H$_5$ | 324 | 4-OC$_2$H$_5$ |
| 325 | 2-NHCH$_3$ | 326 | 3-NHCH$_3$ | 327 | 4-NHCH$_3$ |

TABLE 25-continued

| No. | (R₁₀)n | No. | (R₁₀)n | No. | (R₁₀)n |
|---|---|---|---|---|---|
| 328 | 2-N(CH₃)₂ | 329 | 3-N(CH₃)₂ | 330 | 4-N(CH₃)₂ |
| 331 | 2-COCH₃ | 332 | 3-COCH₃ | 333 | 4-COCH₃ |
| 334 | 2-COC₂H₅ | 335 | 3-COC₂H₅ | 336 | 4-COC₂H₅ |
| 337 | 2-SO₂CH₃ | 338 | 3-SO₂CH₃ | 339 | 4-SO₂CH₃ |
| 340 | 2-OCHF₂ | 341 | 3-OCHF₂ | 342 | 4-OCHF₂ |
| 343 | 2-SO₂C₂H₅ | 344 | 3-SO₂C₂H₅ | 345 | 4-SO₂C₂H₅ |
| 346 | 2-CO₂CH₃ | 347 | 3-CO₂CH₃ | 348 | 4-CO₂CH₃ |
| 349 | 2-CO₂C₂H₅ | 350 | 3-CO₂C₂H₅ | 351 | 4-CO₂C₂H₅ |
| 352 | 2-CH₂OCH₃ | 353 | 3-CH₂OCH₃ | 354 | 4-CH₂OCH₃ |
| 355 | 2-OCOCH₃ | 356 | 3-OCOCH₃ | 357 | 4-OCOCH₃ |
| 358 | 2-OCOCH₂CH₃ | 359 | 3-OCOCH₂CH₃ | 360 | 4-OCOCH₂CH₃ |
| 361 | 2-OCO₂CH₃ | 362 | 3-OCO₂CH₃ | 363 | 4-OCO₂CH₃ |
| 364 | 2-OCH₂OCH₃ | 365 | 3-OCH₂OCH₃ | 366 | 4-OCH₂OCH₃ |
| 367 | 2-OCF₂OCF₃ | 368 | 3-OCF₂OCF₃ | 369 | 4-OCF₂OCF₃ |
| 370 | 2-COPh | 371 | 3-COPh | 372 | 4-COPh |
| 373 | 2-COCH₂Ph | 374 | 3-COCH₂Ph | 375 | 4-COCH₂Ph |
| 376 | 2-NHPh | 377 | 3-NHPh | 378 | 4-NHPh |
| 379 | 2-OPh | 380 | 3-OPh | 381 | 4-OPh |
| 382 | 2-CONHPh | 383 | 3-CONHPh | 384 | 4-CONHPh |
| 385 | 2-CO₂Ph | 386 | 3-CO₂Ph | 387 | 4-CO₂Ph |
| 388 | 2-CONH₂ | 389 | 3-CONH₂ | 390 | 4-CONH₂ |
| 391 | 2-Cl-4-F | 392 | 2-Cl-4-Br | 393 | 2-Cl-4-CH₃ |
| 394 | 2-Cl-4-CF₃ | 395 | 2-Cl-4-NO₂ | 396 | 2-Cl-4-CN |
| 397 | 2-Cl-4-OCF₃ | 398 | 2-F-4-Cl | 399 | 2-Br-4-Cl |
| 400 | 2-CH₃-4-Cl | 401 | 2-CF₃-4-Cl | 402 | 2-NO₂-4-Cl |
| 403 | 2-CN-4-Cl | 404 | 2-OCF₃-4-Cl | 405 | 2,6-2Cl-4-NO₂ |
| 406 | 2,6-2Cl-4-CF₃ | 407 | 2,6-2Cl-4-CN | 408 | 2,6-2Cl-4-COCH₃ |
| 409 | 2,6-2Cl-4-CONH₂ | 410 | 2,4-2Cl-6-NO₂ | 411 | 2,4-2Cl-6-CN |
| 412 | 2,4-2Cl-6-CF₃ | 413 | 2,4-2F-6-NO₂ | 414 | 2,6-2F-4-NO₂ |
| 415 | 2-NO₂-4-F | 416 | 2-NO₂-4-Br | 417 | 2-NO₂-4-CF₃ |
| 418 | 2-NO₂-4-CN | 419 | 2-NO₂-4-COCH₃ | 420 | 2-NO₂-4-CONH₂ |
| 421 | 2-NO₂-4-CH₃ | 422 | 2-NO₂-4-OCH₃ | 423 | 2-NO₂-4-SCH₃ |
| 424 | 2-NO₂-4-NCH₃ | 425 | 2-F-4-NO₂ | 426 | 2-Br-4-NO₂ |
| 427 | 2-CF₃-4-NO₂ | 428 | 2-CN-4-NO₂ | 429 | 2-COCH₃-4-NO₂ |
| 430 | 2-CONH₂-4-NO₂ | 431 | 2-CH₃-4-NO₂ | 432 | 2-Cl-4-F-6-NO₂ |
| 433 | 2-Cl-4-Br-6-NO₂ | 434 | 2-Cl-4-CH₃-6-NO₂ | 435 | 2-Cl-4-CF₃-6-NO₂ |
| 436 | 2-Cl-4,6-2NO₂ | 437 | 2-Cl-4-CN-6-NO₂ | 438 | 2-Cl-4-OCF₃-6-NO₂ |
| 439 | 2-F-4-Cl-6-NO₂ | 440 | 2-Br-4-Cl-6-NO₂ | 441 | 2-CH₃-4-Cl-6-NO₂ |
| 442 | 2-CF₃-4-Cl-6-NO₂ | 443 | 4-Cl-2,6-2NO₂ | 444 | 2-CF₃-4-CN |
| 445 | 2-CN-4-CF₃ | 446 | 4-CF₃-2,6-2NO₂ | 447 | 4-CN-2,6-2NO₂ |
| 448 | 4-CH₃-2,6-2NO₂ | 449 | 4-OCF₃-2,6-2NO₂ | 450 | 4-OCH₃-2,6-2NO₂ |
| 451 | 4-SCH₃-2,6-2NO₂ | 452 | 4-NHCH₃-2,6-2NO₂ | 453 | 4-F-2,6-2NO₂ |
| 454 | 2-CF₃-4,6-2NO₂ | 455 | 2-CN-4,6-2NO₂ | 456 | 2-CH₃-4,6-2NO₂ |
| 457 | 2-F-4,6-2NO₂ | 458 | 2-OCF₃-4,6-2NO₂ | 459 | 2-CF₃-4-Br |
| 460 | 3-CF₃-4-NO₂ | 461 | 2-CN-4-Cl-6-NO₂ | 462 | 2-OCF₃-4-Cl-6-NO₂ |
| 463 | 3-CF₃-4-CN | 464 | 3-CN-4-CF₃ | 465 | 2-CF₃-4-Br-6-NO₂ |
| 466 | 3-NO₂-4-CF₃ | 467 | 2-NO₂-4-CN-5-CF₃ | 468 | 2-NO₂-4-CF₃-5-CN |
| 469 | 4-OCF₃-2,6-2Br | 470 | 2-CH₃-4-Cl-5-CH₂CO₂C₂H₅ | 471 | 2,4-2Cl-3-CH₃ |
| 472 | 2,4-2Cl-3-CH₃-6-NO₂ | 473 | 2-Cl-3-CH₃ | 474 | 2-CH₃-3-Cl |
| 475 | 2-CH₃-3-Cl-4,6-2NO₂ | 476 | 2-CH₃-3-Cl-4-NO₂ | 477 | 2-CH₃-3-Cl-6-NO₂ |
| 478 | 2-Cl-3-CH₃-4,6-2NO₂ | 479 | 2-Cl-3-CH₃-4-NO₂ | 480 | 2-Cl-3-CH₃-6-NO₂ |
| 481 | 2-Br-4-NO₂-6-CN | 482 | 3-Cl-4-CF₃-2,6-2NO₂ | 483 | 2NO₂-4,5-2Cl |
| 484 | 2-NO₂-3,5-2Cl | 485 | 2,5-2Cl-4-NO₂ | 486 | 2,5-2Cl-6-NO₂ |
| 487 | 2,3-2Cl-4-NO₂ | 488 | 2,3-2Cl-6-NO₂ | 489 | 3,4-2Cl-2,6-2NO₂ |
| 490 | 2,5-2Cl-4,6-2NO₂ | 491 | 2,4,5-3Cl-6-NO₂ | 492 | 2,3,4-3Cl-5-NO₂ |
| 493 | 2,3,4-3Cl-6-NO₂ | 494 | 2,3,5-3Cl-4,6-2CN | 495 | 2,5-2Cl-4-OCF₂OCF₃ |
| 496 | 2,6-2Br-4-NO₂ | 497 | 2-F-4-NO₂-6-Cl | 498 | 2-Cl-4-NO₂-6-SCN |
| 499 | 2-Br-4-NO₂-6-Cl | 500 | 2-Cl-4-NO₂-6-OCH₃ | 501 | 2-Cl-4-NO₂-6-SCH₃ |
| 502 | 2-Cl-4-NO₂-6-NHCH₃ | 503 | 2-Cl-4-NO₂-6-SO₂CH₃ | 504 | 2-Cl-4-SO₂CH₃ |
| 505 | 2,6-2Cl-4-SO₂CH₃ | 506 | 2,6-2Cl-4-CH₃ | 507 | 2,6-2Cl-4-CO₂CH₃ |
| 508 | 2,6-2Cl-4-CONHCH₃ | 509 | 2,6-2Cl-4-CON(CH₃)₂ | 510 | 2,6-2Cl-4-CF(CF₃)₂ |
| 511 | 2-Cl-4-CF(CF₃)₂-6-Br | 512 | 2-F-4-CF(CF₃)₂-6-Br | 513 | 2-F-4-CF(CF₃)₂-6-Cl |
| 514 | 2,4,5-3Cl-3,6-2CN | 515 | 2,3,5-3F-4,6-2CN | 516 | 2-SO₂NH₂ |
| 517 | 3-SO₂NH₂ | 518 | 4-SO₂NH₂ | | |

Table 26: in general formula IB, R₁=C₂H₅, R₂=Cl, R₃=R₄=R=R₅=R₆=H, the substituents (R₁₀)n are consistent with those in Table 25 and corresponding to 241-518 in table 25 in turn, the representative compounds are coded as 519-796.

Table 27: in general formula IB, R₁=CHF₂, R₂=Cl, R₃=R=R₅=R₆=H, the substituents (R₁₀)n are consistent with those in Table 25 and corresponding to 241-518 in table 25 in turn, the representative compounds are coded as 797-1074.

Table 28: in general formula IB, R₁=CF₃, R₂=Cl, R₃=R₄=R₅=R₆=H, the substituents (R₁₀)n are consistent with those in Table 25 and corresponding to 241-518 in table 25 in turn, the representative compounds are coded as 1075-1352.

Table 29: in general formula IB, R₁=CH₃, R₂=Cl, R₃=CH₃, R₄=R₅=R₆=H, the substituents (R₁₀)n are consistent with those in Table 25 and corresponding to 241-518 in table 25 in turn, the representative compounds are coded as 1353-1630.

Table 30: in general formula IB, $R_1=C_2H_5$, $R_2=Cl$, $R_3=CH_3$, $R_4=R_5=R_6=H$, the substituents $(R_{10})n$ are consistent with those in Table 25 and corresponding to 241-518 in table 25 in turn, the representative compounds are coded as 1631-1908.

Table 31: in general formula IB, $R_1=CHF_2$, $R_2=Cl$, $R_3=CH_3$, $R_4=R_5=R_6=H$, the substituents $(R_{10})n$ are consistent with those in Table 25 and corresponding to 241-518 in table 25 in turn, the representative compounds are coded as 1909-2186.

Table 32: in general formula IB, $R_1=CF_3$, $R_2=Cl$, $R_3=CH_3$, $R_4=R_5=R_6=H$, the substituents $(R_{10})n$ are consistent with those in Table 25 and corresponding to 241-518 in table 25 in turn, the representative compounds are coded as 2187-2464.

Table 33: in general formula IB, $R_1=CH_3$, $R_2=Cl$, $R_3=R_4=R_5=H$, $R_6=CH_3$, the substituents $(R_{10})n$ are consistent with those in Table 25 and corresponding to 241-518 in table 25 in turn, the representative compounds are coded as 2465-2742.

Table 34: in general formula IB, $R_1=C_2H_5$, $R_2=Cl$, $R_3=R_4=R_5=H$, $R_6=CH_3$, the substituents $(R_{10})n$ are consistent with those in Table 25 and corresponding to 241-518 in table 25 in turn, the representative compounds are coded as 2743-3020.

Table 35: in general formula IB, $R_1=CHF_2$, $R_2=Cl$, $R_3=R_4=R_5=H$, $R_6=CH_3$, the substituents $(R_{10})n$ are consistent with those in Table 25 and corresponding to 241-518 in table 25 in turn, the representative compounds are coded as 3021-3298.

Table 36: in general formula IB, $R_1=CF_3$, $R_2=Cl$, $R_3=R_4=R_5=H$, $R_6=CH_3$, the substituents $(R_{10})n$ are consistent with those in Table 25 and corresponding to 241-518 in table 25 in turn, the representative compounds are coded as 3299-3576.

Table 37: in general formula IB, $R_1=CH_3$, $R_2=Cl$, $R_3=CH_3$, $R_4=R_5=H$, $R_6=CH_3$, the substituents $(R_{10})n$ are consistent with those in Table 25 and corresponding to 241-518 in table 25 in turn, the representative compounds are coded as 3577-3854.

Table 38: in general formula IB, $R_1=C_2H_5$, $R_2=Cl$, $R_3=CH_3$, $R_4=R_5=H$, $R_6=CH_3$, the substituents $(R_{10})n$ are consistent with those in Table 25 and corresponding to 241-518 in table 25 in turn, the representative compounds are coded as 3855-4132.

Table 39: in general formula IB, $R_1=CHF_2$, $R_2=Cl$, $R_3=CH_3$, $R_4=R_5=H$, $R_6=CH_3$, the substituents $(R_{10})n$ are consistent with those in Table 25 and corresponding to 241-518 in table 25 in turn, the representative compounds are coded as 4133-4410.

Table 40: in general formula IB, $R_1=CF_3$, $R_2=Cl$, $R_3=CH_3$, $R_4=R_5=H$, $R_6=CH_3$, the substituents $(R_{10})n$ are consistent with those in Table 25 and corresponding to 241-518 in table 25 in turn, the representative compounds are coded as 4411-4688.

In general formula IC, $R_1=CH_3$, $R_2=Cl$, $R_3=R_4=R_5=R_6=H$, the substituents $R_{15}$, $R_{16}$, $R_{17}$ and $R_{18}$ refer to Table 41, the representative compounds are coded as 4689-4730.

TABLE 41

| No. | $R_{15}$ | $R_{16}$ | $R_{17}$ | $R_{18}$ |
|---|---|---|---|---|
| 4689 | H | H | H | H |
| 4690 | H | H | H | F |
| 4691 | H | H | H | Cl |
| 4692 | H | H | H | Br |
| 4693 | H | H | Cl | H |
| 4694 | H | Cl | H | H |
| 4695 | H | Br | H | H |
| 4696 | Cl | H | H | H |
| 4697 | H | H | H | $NO_2$ |
| 4698 | H | H | $NO_2$ | H |
| 4699 | H | $NO_2$ | H | H |
| 4700 | H | CN | H | H |
| 4701 | H | $OCF_3$ | H | H |
| 4702 | H | H | H | $CH_3$ |
| 4703 | H | H | $CH_3$ | H |
| 4704 | H | $CH_3$ | H | H |
| 4705 | $CH_3$ | H | H | H |
| 4706 | H | H | H | $CF_3$ |
| 4707 | H | H | $CF_3$ | H |
| 4708 | H | $CF_3$ | H | H |
| 4709 | H | H | H | $OCH_3$ |
| 4710 | H | H | $OCH_3$ | H |
| 4711 | H | $OCH_3$ | H | H |
| 4712 | $OCH_3$ | H | H | H |
| 4713 | H | Cl | H | Cl |
| 4714 | Cl | H | Cl | H |
| 4715 | H | $NO_2$ | H | Cl |
| 4716 | H | CN | H | Cl |
| 4717 | H | $CF_3$ | H | Cl |
| 4718 | H | $NO_2$ | H | Br |
| 4719 | H | H | Cl | $NO_2$ |
| 4720 | H | Cl | H | $NO_2$ |
| 4721 | H | CN | H | $CH_3$ |
| 4722 | H | Br | $CH_3$ | H |
| 4723 | H | $NO_2$ | $CH_3$ | H |
| 4724 | $CH_3$ | H | $CH_3$ | H |
| 4725 | H | Cl | H | $CF_3$ |
| 4726 | Cl | H | H | $CF_3$ |
| 4727 | $CH_3$ | Cl | $CH_3$ | Cl |
| 4728 | Cl | Cl | H | Cl |
| 4729 | Cl | $CF_3$ | H | Br |
| 4730 | H | Br | $CH_3$ | Br |

Table 42: in general formula IC, $R_1=C_2H_5$, $R_2=Cl$, $R_3=R_4=R_5=R_6=H$, the substituents $R_{15}$, $R_{16}$, $R_{17}$ and $R_{18}$ are consistent with those in Table 41 and corresponding to 4689-4730 in table 41 in turn, the representative compounds are coded as 4731-4772.

Table 43: in general formula IC, $R_1=CHF_2$, $R_2=Cl$, $R_3=R_4=R_5=R_6=H$, the substituents $R_{15}$, $R_{16}$, $R_{17}$ and $R_{18}$ are consistent with those in Table 41 and corresponding to 4689-4730 in table 41 in turn, the representative compounds are coded as 4773-4814.

Table 44: in general formula IC, $R_1=CF_3$, $R_2=Cl$, $R_3=R_4=R_5=R_6=H$, the substituents $R_{15}$, $R_{16}$, $R_{17}$ and $R_{18}$ are consistent with those in Table 41 and corresponding to 4689-4730 in table 41 in turn, the representative compounds are coded as 4815-4856.

Table 45: in general formula IC, $R_1=CH_3$, $R_2=Cl$, $R_3=CH_3$, $R_4=R_5=R_6=H$, the substituents $R_{15}$, $R_{16}$, $R_{17}$ and $R_{18}$ are consistent with those in Table 41 and corresponding to 4689-4730 in table 41 in turn, the representative compounds are coded as 4857-4898.

Table 46: in general formula IC, $R_1=C_2H_5$, $R_2=Cl$, $R_3=CH_3$, $R_4=R_5=R_6=H$, the substituents $R_{15}$, $R_{16}$, $R_{17}$ and $R_{18}$ are consistent with those in Table 41 and corresponding to 4689-4730 in table 41 in turn, the representative compounds are coded as 4899-4940.

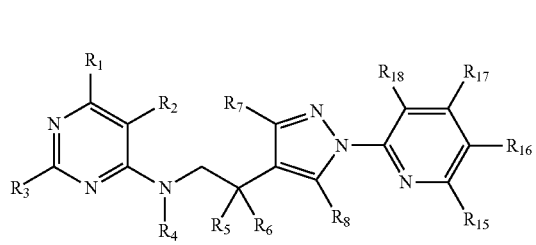

IC

Table 47: in general formula IC, $R_1$=CHF$_2$, $R_2$=C, $R_3$=CH$_3$, $R_4$=R$_5$=R$_6$=H, the substituents $R_{15}$, $R_{16}$, $R_{17}$ and $R_{18}$ are consistent with those in Table 41 and corresponding to 4689-4730 in table 41 in turn, the representative compounds are coded as 4941-4982.

Table 48: in general formula IC, $R_1$=CF$_3$, $R_2$=Cl, $R_3$=CH$_3$, $R_4$=R$_5$=R$_6$=H, the substituents $R_{15}$, $R_{16}$, $R_{17}$ and $R_{18}$ are consistent with those in Table 41 and corresponding to 4689-4730 in table 41 in turn, the representative compounds are coded as 4983-5024.

Table 49: in general formula IC, $R_1$=CH$_3$, $R_2$=Cl, $R_3$=R$_4$=R$_5$=H, $R_6$=CH$_3$, the substituents $R_{15}$, $R_{16}$, $R_{17}$ and $R_{18}$ are consistent with those in Table 41 and corresponding to 4689-4730 in table 41 in turn, the representative compounds are coded as 5025-5066.

Table 50: in general formula IC, $R_1$=C$_2$H$_5$, $R_2$=Cl, $R_3$=R$_4$=R$_5$=H, $R_6$=CH$_3$, the substituents $R_{15}$, $R_{16}$, $R_{17}$ and $R_{18}$ are consistent with those in Table 41 and corresponding to 4689-4730 in table 41 in turn, the representative compounds are coded as 5067-5108.

Table 51: in general formula IC, $R_1$=CHF$_2$, $R_2$=Cl, $R_3$=R$_4$=R$_5$=H, $R_6$=CH$_3$, the substituents $R_{15}$, $R_{16}$, $R_{17}$ and $R_{18}$ are consistent with those in Table 41 and corresponding to 4689-4730 in table 41 in turn, the representative compounds are coded as 5109-5150.

Table 52: in general formula IC, $R_1$=CF$_3$, $R_2$=Cl, $R_3$=R$_4$=R=H, $R_6$=CH$_3$, the substituents $R_{15}$, $R_{16}$, $R_{17}$ and $R_{18}$ are consistent with those in Table 41 and corresponding to 4689-4730 in table 41 in turn, the representative compounds are coded as 5151-5192.

Table 53: in general formula IC, $R_1$=CH$_3$, $R_2$=Cl, $R_3$=CH$_3$, $R_4$=R=H—, $R_6$=CH$_3$, the substituents $R_{15}$, $R_{16}$, $R_{17}$ and $R_{18}$ are consistent with those in Table 41 and corresponding to 4689-4730 in table 41 in turn, the representative compounds are coded as 5193-5234.

Table 54: in general formula IC, $R_1$=C$_2$H$_5$, $R_2$=Cl, $R_3$=CH$_3$, $R_4$=R$_5$=H, $R_6$=CH$_3$, the substituents $R_{15}$, $R_{16}$, $R_{17}$ and $R_{15}$ are consistent with those in Table 41 and corresponding to 4689-4730 in table 41 in turn, the representative compounds are coded as 5235-5276.

Table 55: in general formula IC, $R_1$=CHF$_2$, $R_2$=Cl, $R_3$=CH$_3$, $R_4$=R$_5$=H, $R_6$=CH$_3$, the substituents $R_{15}$, $R_{16}$, $R_{17}$ and $R_{18}$ are consistent with those in Table 41 and corresponding to 4689-4730 in table 41 in turn, the representative compounds are coded as 5277-5318.

Table 56: in general formula IC, $R_1$=CF$_3$, $R_2$=Cl, $R_3$=CH$_3$, $R_4$=R$_5$=H, $R_6$=CH$_3$, the substituents $R_{15}$, $R_{16}$, $R_{17}$ and $R_{18}$ are consistent with those in Table 41 and corresponding to 4689-4730 in table 41 in turn, the representative compounds are coded as 5319-5360.

In general formula ID,

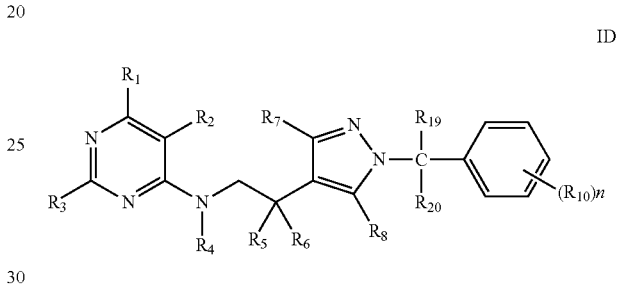

$R_1$=CH$_3$, $R_2$=Cl, $R_3$=R$_4$=R$_5$=R$_6$=H, the substituents $(R_{10})n$ refer to Table 57, the representative compounds are coded as 5361-5638.

TABLE 57

| No. | $(R_{10})n$ | No. | $(R_{10})n$ | No. | $(R_{10})n$ |
|---|---|---|---|---|---|
| 5361 | H | 5362 | 2-F | 5363 | 3-F |
| 5364 | 4-F | 5365 | 2,3-2F | 5366 | 2,4-2F |
| 5367 | 2,5-2F | 5368 | 2,6-2F | 5369 | 3,4-2F |
| 5370 | 3,5-2F | 5371 | 2,3,4-3F | 5372 | 2,3,5-3F |
| 5373 | 2,4,5-3F | 5374 | 2,3,6-3F | 5375 | 2,4,6-3F |
| 5376 | 3,4,5-3F | 5377 | 2-Cl | 5378 | 3-Cl |
| 5379 | 4-Cl | 5380 | 2,3-2Cl | 5381 | 2,4-2Cl |
| 5382 | 2,5-2Cl | 5383 | 2,6-2Cl | 5384 | 3,4-2Cl |
| 5385 | 3,5-2Cl | 5386 | 2,3,4-3Cl | 5387 | 2,3,5-3Cl |
| 5388 | 2,4,5-3Cl | 5389 | 2,3,6-3Cl | 5390 | 2,4,6-3Cl |
| 5391 | 3,4,5-3Cl | 5392 | 2-Br | 5393 | 3-Br |
| 5394 | 4-Br | 5395 | 2,3-Br | 5396 | 2,4-2Br |
| 5397 | 2,5-2Br | 5398 | 2,6-2Br | 5399 | 3,4-2Br |
| 5400 | 3,5-2Br | 5401 | 2,3,4-3Br | 5402 | 2,3,5-3Br |
| 5403 | 2,4,5-3Br | 5404 | 2,3,6-3Br | 5405 | 2,4,6-3Br |
| 5406 | 3,4,5-3Br | 5407 | 2-CN | 5408 | 3-CN |
| 5409 | 4-CN | 5410 | 2-NO$_2$ | 5411 | 3-NO$_2$ |
| 5412 | 4-NO$_2$ | 5413 | 2,4-2NO$_2$ | 5414 | 2,4,6-3NO$_2$ |
| 5415 | 2-CH$_3$ | 5416 | 3-CH$_3$ | 5417 | 4-CH$_3$ |
| 5418 | 2,3-2CH$_3$ | 5419 | 2,4-2CH$_3$ | 5420 | 2,5-2CH$_3$ |
| 5421 | 2,6-2CH$_3$ | 5422 | 3,4-2CH$_3$ | 5423 | 3,5-2CH$_3$ |
| 5424 | 2-C$_2$H$_5$ | 5425 | 3-C$_2$H$_5$ | 5426 | 4-C$_2$H$_5$ |
| 5427 | 2-CF$_3$ | 5428 | 3-CF$_3$ | 5429 | 4-CF$_3$ |
| 5430 | 2-OCH$_3$ | 5431 | 3-OCH$_3$ | 5432 | 4-OCH$_3$ |
| 5433 | 2-SCH$_3$ | 5434 | 3-SCH$_3$ | 5435 | 4-SCH$_3$ |
| 5436 | 2-OCF$_3$ | 5437 | 3-OCF$_3$ | 5438 | 4-OCF$_3$ |
| 5439 | 2-SCF$_3$ | 5440 | 3-SCF$_3$ | 5441 | 4-SCF$_3$ |
| 5442 | 2-OC$_2$H$_5$ | 5443 | 3-OC$_2$H$_5$ | 5444 | 4-OC$_2$H$_5$ |
| 5445 | 2-NHCH$_3$ | 5446 | 3-NHCH$_3$ | 5447 | 4-NHCH$_3$ |
| 5448 | 2-N(CH$_3$)$_2$ | 5449 | 3-N(CH$_3$)$_2$ | 5450 | 4-N(CH$_3$)$_2$ |
| 5451 | 2-COCH$_3$ | 5452 | 3-COCH$_3$ | 5453 | 4-COCH$_3$ |
| 5454 | 2-COC$_2$H$_5$ | 5455 | 3-COC$_2$H$_5$ | 5456 | 4-COC$_2$H$_5$ |
| 5457 | 2-SO$_2$CH$_3$ | 5458 | 3-SO$_2$CH$_3$ | 5459 | 4-SO$_2$CH$_3$ |
| 5460 | 2-OCHF$_2$ | 5461 | 3-OCHF$_2$ | 5462 | 4-OCHF$_2$ |
| 5463 | 2-SO$_2$C$_2$H$_5$ | 5464 | 3-SO$_2$C$_2$H$_5$ | 5465 | 4-SO$_2$C$_2$H$_5$ |

TABLE 57-continued

| No. | (R$_{10}$)n | No. | (R$_{10}$)n | No. | (R$_{10}$)n |
|---|---|---|---|---|---|
| 5466 | 2-CO$_2$CH$_3$ | 5467 | 3-CO$_2$CH$_3$ | 5468 | 4-CO$_2$CH$_3$ |
| 5469 | 2-CO$_2$C$_2$H$_5$ | 5470 | 3-CO$_2$C$_2$H$_5$ | 5471 | 4-CO$_2$C$_2$H$_5$ |
| 5472 | 2-CH$_2$OCH$_3$ | 5473 | 3-CH$_2$OCH$_3$ | 5474 | 4-CH$_2$OCH$_3$ |
| 5475 | 2-OCOCH$_3$ | 5476 | 3-OCOCH$_3$ | 5477 | 4-OCOCH$_3$ |
| 5478 | 2-OCOCH$_2$CH$_3$ | 5479 | 3-OCOCH$_2$CH$_3$ | 5480 | 4-OCOCH$_2$CH$_3$ |
| 5481 | 2-OCO$_2$CH$_3$ | 5482 | 3-OCO$_2$CH$_3$ | 5483 | 4-OCO$_2$CH$_3$ |
| 5484 | 2-OCH$_2$OCH$_3$ | 5485 | 3-OCH$_2$OCH$_3$ | 5486 | 4-OCH$_2$OCH$_3$ |
| 5487 | 2-OCF$_2$OCF$_3$ | 5488 | 3-OCF$_2$OCF$_3$ | 5489 | 4-OCF$_2$OCF$_3$ |
| 5490 | 2-COPh | 5491 | 3-COPh | 5492 | 4-COPh |
| 5493 | 2-COCH$_2$Ph | 5494 | 3-COCH$_2$Ph | 5495 | 4-COCH$_2$Ph |
| 5496 | 2-NHPh | 5497 | 3-NHPh | 5498 | 4-NHPh |
| 5499 | 2-OPh | 5500 | 3-OPh | 5501 | 4-OPh |
| 5502 | 2-CONHPh | 5503 | 3-CONHPh | 5504 | 4-CONHPh |
| 5505 | 2-CO$_2$Ph | 5506 | 3-CO$_2$Ph | 5507 | 4-CO$_2$Ph |
| 5508 | 2-CONH$_2$ | 5509 | 3-CONH$_2$ | 5510 | 4-CONH$_2$ |
| 5511 | 2-Cl-4-F | 5512 | 2-Cl-4-Br | 5513 | 2-Cl-4-CH$_3$ |
| 5514 | 2-Cl-4-CF$_3$ | 5515 | 2-Cl-4-NO$_2$ | 5516 | 2-Cl-4-CN |
| 5517 | 2-Cl-4-OCF$_3$ | 5518 | 2-F-4-Cl | 5519 | 2-Br-4-Cl |
| 5520 | 2-CH$_3$-4-Cl | 5521 | 2-CF$_3$-4-Cl | 5522 | 2-NO$_2$-4-Cl |
| 5523 | 2-CN-4-Cl | 5524 | 2-OCF$_3$-4-Cl | 5525 | 2,6-2Cl-4-NO$_2$ |
| 5526 | 2,6-2Cl-4-CF$_3$ | 5527 | 2,6-2Cl-4-CN | 5528 | 2,6-2Cl-4-COCH$_3$ |
| 5529 | 2,6-2Cl-4-CONH$_2$ | 5530 | 2,4-2Cl-6-NO$_2$ | 5531 | 2,4-2Cl-6-CN |
| 5532 | 2,4-2Cl-6-CF$_3$ | 5533 | 2,4-2F-6-NO$_2$ | 5534 | 2,6-2F-4-NO$_2$ |
| 5535 | 2-NO$_2$-4-F | 5536 | 2-NO$_2$-4-Br | 5537 | 2-NO$_2$-4-CF$_3$ |
| 5538 | 2-NO$_2$-4-CN | 5539 | 2-NO$_2$-4-COCH$_3$ | 5540 | 2-NO$_2$-4-CONH$_2$ |
| 5541 | 2-NO$_2$-4-CH$_3$ | 5542 | 2-NO$_2$-4-OCH$_3$ | 5543 | 2-NO$_2$-4-SCH$_3$ |
| 5544 | 2-NO$_2$-4-NCH$_3$ | 5545 | 2-F-4-NO$_2$ | 5546 | 2-Br-4-NO$_2$ |
| 5547 | 2-CF$_3$-4-NO$_2$ | 5548 | 2-CN-4-NO$_2$ | 5549 | 2-COCH$_3$-4-NO$_2$ |
| 5550 | 2-CONH$_2$-4-NO$_2$ | 5551 | 2-CH$_3$-4-NO$_2$ | 5552 | 2-Cl-4-F-6-NO$_2$ |
| 5553 | 2-Cl-4-Br-6-NO$_2$ | 5554 | 2-Cl-4-CH$_3$-6-NO$_2$ | 5555 | 2-Cl-4-CF$_3$-6-NO$_2$ |
| 5556 | 2-Cl-4,6-2NO$_2$ | 5557 | 2-Cl-4-CN-6-NO$_2$ | 5558 | 2-Cl-4-OCF$_3$-6-NO$_2$ |
| 5559 | 2-F-4-Cl-6-NO$_2$ | 5560 | 2-Br-4-Cl-6-NO$_2$ | 5561 | 2-CH$_3$-4-Cl-6-NO$_2$ |
| 5562 | 2-CF$_3$-4-Cl-6-NO$_2$ | 5563 | 4-Cl-2,6-2NO$_2$ | 5564 | 2-CF$_3$-4-CN |
| 5565 | 2-CN-4-CF$_3$ | 5566 | 4-CF$_3$-2,6-2NO$_2$ | 5567 | 4-CN-2,6-2NO$_2$ |
| 5568 | 4-CH$_3$-2,6-2NO$_2$ | 5569 | 4-OCF$_3$-2,6-2NO$_2$ | 5570 | 4-OCH$_3$-2,6-2NO$_2$ |
| 5571 | 4-SCH$_3$-2,6-2NO$_2$ | 5572 | 4-NHCH$_3$-2,6-2NO$_2$ | 5573 | 4-F-2,6-2NO$_2$ |
| 5574 | 2-CF$_3$-4,6-2NO$_2$ | 5575 | 2-CN-4,6-2NO$_2$ | 5576 | 2-CH$_3$-4,6-2NO$_2$ |
| 5577 | 2-F-4,6-2NO$_2$ | 5578 | 2-OCF$_3$-4,6-2NO$_2$ | 5579 | 2-CF$_3$-4-Br |
| 5580 | 3-CF$_3$-4-NO$_2$ | 5581 | 2-CN-4-Cl-6-NO$_2$ | 5582 | 2-OCF$_3$-4-Cl-6-NO$_2$ |
| 5583 | 3-CF$_3$-4-CN | 5584 | 3-CN-4-CF$_3$ | 5585 | 2-CF$_3$-4-Br-6-NO$_2$ |
| 5586 | 3-NO$_2$-4-CF$_3$ | 5587 | 2-NO$_2$-4-CN-5-CF$_3$ | 5588 | 2-NO$_2$-4-CF$_3$-5-CN |
| 5589 | 4-OCF$_3$-2,6-2Br | 5590 | 2-CH$_3$-4-Cl-5-CH$_2$CO$_2$C$_2$H$_5$ | 5591 | 2,4-2Cl-3-CH$_3$ |
| 5592 | 2,4-2Cl-3-CH$_3$-6-NO$_2$ | 5593 | 2-Cl-3-CH$_3$ | 5594 | 2-CH$_3$-3-Cl |
| 5595 | 2-CH$_3$-3-Cl-4,6-2NO$_2$ | 5596 | 2-CH$_3$-3-Cl-4-NO$_2$ | 5597 | 2-CH$_3$-3-Cl-6-NO$_2$ |
| 5598 | 2-Cl-3-CH$_3$-4,6-2NO$_2$ | 5599 | 2-Cl-3-CH$_3$-4-NO$_2$ | 5600 | 2-Cl-3-CH$_3$-6-NO$_2$ |
| 5601 | 2-Br-4-NO$_2$-6-CN | 5602 | 3-Cl-4-CF$_3$-2,6-2NO$_2$ | 5603 | 2NO$_2$-4,5-2Cl |
| 5604 | 2-NO$_2$-3,5-2Cl | 5605 | 2,5-2Cl-4-NO$_2$ | 5606 | 2,5-2Cl-6-NO$_2$ |
| 5607 | 2,3-2Cl-4-NO$_2$ | 5608 | 2,3-2Cl-6-NO$_2$ | 5609 | 3,4-2Cl-2,6-2NO$_2$ |
| 5610 | 2,5-2Cl-4,6-2NO$_2$ | 5611 | 2,4,5-3Cl-6-NO$_2$ | 5612 | 2,3,4-3Cl-5-NO$_2$ |
| 5613 | 2,3,4-3Cl-6-NO$_2$ | 5614 | 2,3,5-3Cl-4,6-2CN | 5615 | 2,5-2Cl-4-OCF$_2$OCF$_3$ |
| 5616 | 2,6-2Br-4-NO$_2$ | 5617 | 2-F-4-NO$_2$-6-Cl | 5618 | 2-Cl-4-NO$_2$-6-SCN |
| 5619 | 2-Br-4-NO$_2$-6-Cl | 5620 | 2-Cl-4-NO$_2$-6-OCH$_3$ | 5621 | 2-Cl-4-NO$_2$-6-SCH$_3$ |
| 5622 | 2-Cl-4-NO$_2$-6-NHCH$_3$ | 5623 | 2-Cl-4-NO$_2$-6-SO$_2$CH$_3$ | 5624 | 2-Cl-4-SO$_2$CH$_3$ |
| 5625 | 2,6-2Cl-4-SO$_2$CH$_3$ | 5626 | 2,6-2Cl-4-CH$_3$ | 5627 | 2,6-2Cl-4-CO$_2$CH$_3$ |
| 5628 | 2,6-2Cl-4-CONHCH$_3$ | 5629 | 2,6-2Cl-4-CON(CH$_3$)$_2$ | 5630 | 2,6-2Cl-4-CF(CF$_3$)$_2$ |
| 5631 | 2-Cl-4-CF(CF$_3$)$_2$-6-Br | 5632 | 2-F-4-CF(CF$_3$)$_2$-6-Br | 5633 | 2-F-4-CF(CF$_3$)$_2$-6-Cl |
| 5634 | 2,4,5-3Cl-3,6-2CN | 5635 | 2,3,5-3F-4,6-2CN | 5636 | 2-SO$_2$NH$_2$ |
| 5637 | 3-SO$_2$NH$_2$ | 5638 | 4-SO$_2$NH$_2$ | | |

Table 58: in general formula ID, R$_1$=C$_2$H$_5$, R$_2$=Cl, R$_3$=R$_4$=R$_5$=R$_6$=H, the substituents (R$_{10}$)n are consistent with those in Table 57 and corresponding to 5361-5638 in table 57 in turn, the representative compounds are coded as 5639-5916.

Table 59: in general formula ID, R$_1$=CHF$_2$, R$_2$=Cl, R$_3$=R$_4$=R$_5$=R$_6$=H, the substituents (R$_{10}$)n are consistent with those in Table 57 and corresponding to 5361-5638 in table 57 in turn, the representative compounds are coded as 5917-6194.

Table 60: in general formula ID, R$_1$=CF$_3$, R$_2$=Cl, R$_3$=R$_4$=R$_5$=R$_6$=H, the substituents (R$_{10}$)n are consistent with those in Table 57 and corresponding to 5361-5638 in table 57 in turn, the representative compounds are coded as 6195-6472.

Table 61: in general formula ID, R$_1$=CH$_3$, R$_2$=Cl, R$_3$=CH$_3$, R$_4$=R$_5$=R$_6$=H, the substituents (R$_{10}$)n are consistent with those in Table 57 and corresponding to 5361-5638 in table 57 in turn, the representative compounds are coded as 6473-6750.

Table 62: in general formula ID, R$_1$=C$_2$H$_5$, R$_2$=Cl, R$_3$=CH$_3$, R$_4$=R$_5$=R$_6$=H, the substituents (R$_{10}$)n are consistent with those in Table 57 and corresponding to 5361-5638 in table 57 in turn, the representative compounds are coded as 6751-7028.

Table 63: in general formula ID, R$_1$=CHF$_2$, R$_2$=Cl, R$_3$=CH$_3$, R$_4$=R$_5$=R$_6$=H, the substituents (R$_{10}$)n are consistent with those in Table 57 and corresponding to 5361-5638 in table 57 in turn, the representative compounds are coded as 7029-7306.

Table 64: in general formula ID, $R_1=CF_3$, $R_2=Cl$, $R_3=CH_3$, $R_4=R_5=R_6=H$, the substituents $(R_{10})n$ are consistent with those in Table 57 and corresponding to 5361-5638 in table 57 in turn, the representative compounds are coded as 7307-7584.

Table 65: in general formula ID, $R_1=CH_3$, $R_2=Cl$, $R_3=R_4=R_5=H$, $R_6=CH_3$, the substituents $(R_{10})n$ are consistent with those in Table 57 and corresponding to 5361-5638 in table 57 in turn, the representative compounds are coded as 7585-7862.

Table 66: in general formula ID, $R_1=C_2H_5$, $R_2=Cl$, $R_3=R_4=R_5=H$, $R_6=CH_3$, the substituents $(R_{10})n$ are consistent with those in Table 57 and corresponding to 5361-5638 in table 57 in turn, the representative compounds are coded as 7863-8140.

Table 67: in general formula ID, $R_1=CHF_2$, $R_2=Cl$, $R_3=R_4=R_5=H$, $R_6=CH_3$, the substituents $(R_{10})n$ are consistent with those in Table 57 and corresponding to 5361-5638 in table 57 in turn, the representative compounds are coded as 8141-8418.

Table 68: in general formula ID, $R_1=CF_3$, $R_2=Cl$, $R_3=R_4=R_5=H$, $R_6=CH_3$, the substituents $(R_{10})n$ are consistent with those in Table 57 and corresponding to 5361-5638 in table 57 in turn, the representative compounds are coded as 8419-8696.

Table 69: in general formula ID, $R_1=CH_3$, $R_2=Cl$, $R_3=CH_3$, $R_4=R_5=H$, $R_6=CH_3$, the substituents $(R_{10})n$ are consistent with those in Table 57 and corresponding to 5361-5638 in table 57 in turn, the representative compounds are coded as 8697-8974.

Table 70: in general formula ID, $R_1=C_2H_5$, $R_2=Cl$, $R_3=CH_3$, $R_4=R_5=H$, $R_6=CH_3$, the substituents $(R_{10})n$ are consistent with those in Table 57 and corresponding to 5361-5638 in table 57 in turn, the representative compounds are coded as 8975-9252.

Table 71: in general formula ID, $R_1=CHF_2$, $R_2=Cl$, $R_3=CH_3$, $R_4=R_5=H$, $R_6=CH_3$, the substituents $(R_{10})n$ are consistent with those in Table 57 and corresponding to 5361-5638 in table 57 in turn, the representative compounds are coded as 9253-9530.

Table 72: in general formula ID, $R_1=CF_3$, $R_2=Cl$, $R_3=CH_3$, $R_4=R_5=H$, $R_6=CH_3$, the substituents $(R_{10})n$ are consistent with those in Table 57 and corresponding to 5361-5638 in table 57 in turn, the representative compounds are coded as 9531-9808.

In general formula IE,

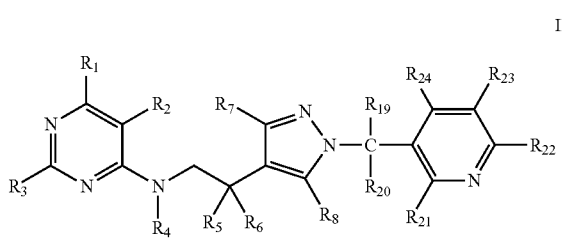

IE $R_1=CH_3$, $R_2=Cl$, $R_3=R_4=R_5=R_6=H$, the substituents $R_{21}$, $R_{22}$, $R_{23}$ and $R_{24}$ refer to Table 73, the representative compounds are coded as 9809-9825.

TABLE 73

| No. | $R_{21}$ | $R_{22}$ | $R_{23}$ | $R_{24}$ |
|---|---|---|---|---|
| 9809 | H | H | H | H |
| 9810 | H | F | H | H |

TABLE 73-continued

| No. | $R_{21}$ | $R_{22}$ | $R_{23}$ | $R_{24}$ |
|---|---|---|---|---|
| 9811 | H | Cl | H | H |
| 9812 | H | Br | H | H |
| 9813 | H | $CH_3$ | H | H |
| 9814 | H | $OCH_3$ | H | H |
| 9815 | H | $CF_3$ | H | H |
| 9816 | H | CN | H | H |
| 9817 | H | H | H | H |
| 9818 | Cl | H | H | H |
| 9819 | $CH_3$ | H | H | H |
| 9820 | $CF_3$ | H | H | H |
| 9821 | CN | H | H | H |
| 9822 | Br | H | H | H |
| 9823 | H | H | $CH_3$ | H |
| 9824 | H | H | H | Cl |
| 9825 | H | H | $NHCH_3$ | H |

Table 74: in general formula IE, $R_1=C_2H_5$, $R_2=Cl$, $R_3=R_4=R_5=R_6=H$, the substituents $R_{21}$, $R_{22}$, $R_{23}$ and $R_{24}$ are consistent with those in Table 73 and corresponding to 9809-9825 in table 73 in turn, the representative compounds are coded as 9826-9842.

Table 75: in general formula IE, $R_1=CHF_2$, $R_2=Cl$, $R_3=R_4=R_5=R_6=H$, the substituents $R_{21}$, $R_{22}$, $R_{23}$ and $R_{24}$ are consistent with those in Table 73 and corresponding to 9809-9825 in table 73 in turn, the representative compounds are coded as 9843-9859.

Table 76: in general formula IE, $R_1=CF_3$, $R_2=Cl$, $R_3=R_4=R_5=R_6=H$, the substituents $R_{21}$, $R_{22}$, $R_{23}$ and $R_{24}$ are consistent with those in Table 73 and corresponding to 9809-9825 in table 73 in turn, the representative compounds are coded as 9860-9876.

Table 77: in general formula IE, $R_1=CH_3$, $R_2=Cl$, $R_3=CH_3$, $R_4=R_5=R_6=H$, the substituents $R_{21}$, $R_{22}$, $R_{23}$ and $R_{24}$ are consistent with those in Table 73 and corresponding to 9809-9825 in table 73 in turn, the representative compounds are coded as 9877-9893.

Table 78: in general formula IE, $R_1=C_2H_5$, $R_2=Cl$, $R_3=CH_3$, $R_4=R_5=R_6=H$, the substituents $R_{21}$, $R_{22}$, $R_{23}$ and $R_{24}$ are consistent with those in Table 73 and corresponding to 9809-9825 in table 73 in turn, the representative compounds are coded as 9894-9910.

Table 79: in general formula IE, $R_1=CHF_2$, $R_2=Cl$, $R_3=CH_3$, $R_4=R_5=R_6=H$, the substituents $R_{21}$, $R_{22}$, $R_{23}$ and $R_{24}$ are consistent with those in Table 73 and corresponding to 9809-9825 in table 73 in turn, the representative compounds are coded as 9911-9927.

Table 80: in general formula IE, $R_1=CF_3$, $R_2=Cl$, $R_3=CH_3$, $R_4=R_5=R_6=H$, the substituents $R_{21}$, $R_{22}$, $R_{23}$ and $R_{24}$ are consistent with those in Table 73 and corresponding to 9809-9825 in table 73 in turn, the representative compounds are coded as 9928-9944.

Table 81: in general formula IE, $R_1=CH_3$, $R_2=Cl$, $R_3=R_4=R_5=H$, $R_6=CH_3$, the substituents $R_{21}$, $R_{22}$, $R_{23}$ and $R_{24}$ are consistent with those in Table 73 and corresponding to 9809-9825 in table 73 in turn, the representative compounds are coded as 9945-9961.

Table 82: in general formula IE, $R_1=C_2H_5$, $R_2=Cl$, $R_3=R_4=R_5=H$, $R_6=CH_3$, the substituents $R_{21}$, $R_{22}$, $R_{23}$ and $R_{24}$ are consistent with those in Table 73 and corresponding to 9809-9825 in table 73 in turn, the representative compounds are coded as 9962-9978.

Table 83: in general formula IE, $R_1=CHF_2$, $R_2=Cl$, $R_3=R_4=R_5=H$, $R_6=CH_3$, the substituents $R_{21}$, $R_{22}$, $R_{23}$ and $R_{24}$ are consistent with those in Table 73 and corresponding to 9809-9825 in table 73 in turn, the representative compounds are coded as 9979-9995.

Table 84: in general formula IE, $R_1=CF_3$, $R_2=Cl$, $R_3=R_4=R_5=H$, $R_6=CH_3$, the substituents $R_{21}$, $R_{22}$, $R_{23}$ and $R_{24}$ are consistent with those in Table 73 and corresponding to 9809-9825 in table 73 in turn, the representative compounds are coded as 9996-10012.

Table 85: in general formula IE, $R_1=CH_3$, $R_2=C$, $R_3=CH_3$, $R_4=R_5=H$, $R_6=CH_3$, the substituents $R_{21}$, $R_{22}$, $R_{23}$ and $R_{24}$ are consistent with those in Table 73 and corresponding to 9809-9825 in table 73 in turn, the representative compounds are coded as 10013-10029.

Table 86: in general formula IE, $R_1=C_2H_5$, $R_2=Cl$, $R_3=CH_3$, $R_4=R_5=H$, $R_6=CH_3$, the substituents $R_{21}$, $R_{22}$, $R_{23}$ and $R_{24}$ are consistent with those in Table 73 and corresponding to 9809-9825 in table 73 in turn, the representative compounds are coded as 10030-10046.

Table 87: in general formula IE, $R_1=CHF_2$, $R_2=Cl$, $R_3=CH_3$, $R_4=R_5=H$, $R_6=CH_3$, the substituents $R_{21}$, $R_{22}$, $R_{23}$ and $R_{24}$ are consistent with those in Table 73 and corresponding to 9809-9825 in table 73 in turn, the representative compounds are coded as 10047-10063.

Table 88: in general formula IE, $R_1=CF_3$, $R_2=Cl$, $R_3=CH_3$, $R_4=R_5=H$, $R_6=CH_3$, the substituents $R_{21}$, $R_{22}$, $R_{23}$ and $R_{24}$ are consistent with those in Table 73 and corresponding to 9809-9825 in table 73 in turn, the representative compounds are coded as 10064-10080.

In general formula IF,

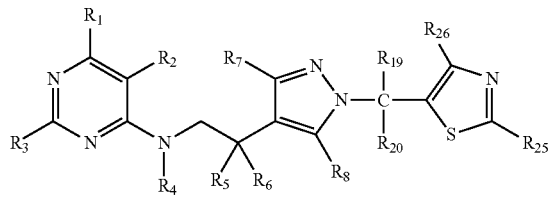

IF $R_1=CH_3$, $R_2=Cl$, $R_3=R_4=R_5=R_6=H$, the substituents $R_{25}$ and $R_{26}$ refer to Table 89, the representative compounds are coded as 10081-10091.

TABLE 89

| No. | $R_{25}$ | $R_{26}$ |
|---|---|---|
| 10081 | H | H |
| 10082 | H | Br |
| 10083 | H | $CH_3$ |
| 10084 | H | Et |
| 10085 | H | CN |
| 10086 | Cl | H |
| 10087 | Br | Br |
| 10088 | Et | $CH_3$ |
| 10089 | i-Pr | H |
| 10090 | Br | $CF_3$ |
| 10091 | $CH_3SO$ | H |

Table 90: in general formula IF, $R_1=C_2H_5$, $R_2=Cl$, $R_3=R_4=R_5=R_6=H$, the substituents $R_{25}$ and $R_{26}$ are consistent with those in Table 89 and corresponding to 10081-10091 in table 89 in turn, the representative compounds are coded as 10092-10102.

Table 91: in general formula IF, $R_1=CHF_2$, $R_2=Cl$, $R_3=R_4=R_5=R_6=H$, the substituents $R_{25}$ and $R_{26}$ are consistent with those in Table 89 and corresponding to 10081-10091 in table 89 in turn, the representative compounds are coded as 10103-10113.

Table 92: in general formula IF, $R_1=CF_3$, $R_2=Cl$, $R_3=R_4=R_5=R_6=H$, the substituents $R_{25}$ and $R_{26}$ are consistent with those in Table 89 and corresponding to 10081-10091 in table 89 in turn, the representative compounds are coded as 10114-10124.

Table 93: in general formula IF, $R_1=CH_3$, $R_2=Cl$, $R_3=CH_3$, $R_4=R_5=R_6=H$, the substituents $R_{25}$ and $R_{26}$ are consistent with those in Table 89 and corresponding to 10081-10091 in table 89 in turn, the representative compounds are coded as 10125-10135.

Table 94: in general formula IF, $R_1=C_2H_5$, $R_2=Cl$, $R_3=CH_3$, $R_4=R_5=R_6=H$, the substituents $R_{25}$ and $R_{26}$ are consistent with those in Table 89 and corresponding to 10081-10091 in table 89 in turn, the representative compounds are coded as 10136-10146.

Table 95: in general formula IF, $R_1=CHF_2$, $R_2=Cl$, $R_3=CH_3$, $R_4=R_5=R_6=H$, the substituents $R_{25}$ and $R_{26}$ are consistent with those in Table 89 and corresponding to 10081-10091 in table 89 in turn, the representative compounds are coded as 10147-10157.

Table 96: in general formula IF, $R_1=CF_3$, $R_2=Cl$, $R_3=CH_3$, $R_4=R_5=R_6=H$, the substituents $R_{25}$ and $R_{26}$ are consistent with those in Table 89 and corresponding to 10081-10091 in table 89 in turn, the representative compounds are coded as 10158-10168.

Table 97: in general formula IF, $R_1=CH_3$, $R_2=Cl$, $R_3=R_4=R_5=H$, $R_6=CH_3$, the substituents $R_{25}$ and $R_{26}$ are consistent with those in Table 89 and corresponding to 10081-10091 in table 89 in turn, the representative compounds are coded as 10169-10179.

Table 98: in general formula IF, $R_1=C_2H_5$, $R_2=Cl$, $R_3=R_4=R_5=H$, $R_6=CH_3$, the substituents $R_{25}$ and $R_{26}$ are consistent with those in Table 89 and corresponding to 10081-10091 in table 89 in turn, the representative compounds are coded as 10180-10190.

Table 99: in general formula IF, $R_1=CHF_2$, $R_2=Cl$, $R_3=R_4=R_5=H$, $R_6=CH_3$, the substituents $R_{25}$ and $R_{26}$ are consistent with those in Table 89 and corresponding to 10081-10091 in table 89 in turn, the representative compounds are coded as 10191-10201.

Table 100: in general formula IF, $R_1=CF_3$, $R_2=Cl$, $R_3=R_4=R_5=H$, $R_6=CH_3$, the substituents $R_{25}$ and $R_{26}$ are consistent with those in Table 89 and corresponding to 10081-10091 in table 89 in turn, the representative compounds are coded as 10202-10212.

Table 101: in general formula IF, $R_1=CH_3$, $R_2=Cl$, $R_3=CH_3$, $R_4=R_5=H$, $R_6=CH_3$, the substituents $R_{25}$ and $R_{26}$ are consistent with those in Table 89 and corresponding to 10081-10091 in table 89 in turn, the representative compounds are coded as 10213-10223.

Table 102: in general formula IF, $R_1=C_2H_5$, $R_2=Cl$, $R_3=CH_3$, $R_4=R_5=H$, $R_6=CH_3$, the substituents $R_{25}$ and $R_{26}$ are consistent with those in Table 89 and corresponding to 10081-10091 in table 89 in turn, the representative compounds are coded as 10224-10234.

Table 103: in general formula IF, $R_1=CHF_2$, $R_2=Cl$, $R_3=CH_3$, $R_4=R_5=H$, $R_6=CH_3$, the substituents $R_{25}$ and $R_{26}$ are consistent with those in Table 89 and corresponding to 10081-10091 in table 89 in turn, the representative compounds are coded as 10235-10245.

Table 104: in general formula IF, $R_1=CF_3$, $R_2=Cl$, $R_3=CH_3$, $R_4=R_5=H$, $R_6=CH_3$, the substituents $R_{25}$ and $R_{26}$ are consistent with those in Table 89 and corresponding to 10081-10091 in table 89 in turn, the representative compounds are coded as 10246-10256.

In general formula IA, $R_1=C_2H_5$, $R_2=Cl$, $R_3=R_5=R_6=H$, $R_{14}=t-C_4H_9$, the substituents $R_4$ refer to Table 105, the representative compounds are coded as 10092-10231.

TABLE 105

| No. | $R_4$ |
|---|---|
| 10092 | $S-i-C_3H_7$ |
| 10093 | OH |
| 10094 | —C(=O)H |
| 10095 | $CBr_3$ |
| 10096 | $CH_3$ |
| 10097 | $C_2H_5$ |
| 10098 | $n-C_3H_7$ |
| 10099 | $i-C_3H_7$ |
| 10100 | $n-C_4H_9$ |
| 10101 | $i-C_4H_9$ |
| 10102 | $t-C_4H_9$ |
| 10103 | $Cl_3$ |
| 10104 | $CH_2Br$ |
| 10105 | $CHF_2$ |
| 10106 | $CHBr_2$ |
| 10107 | $CF_3$ |
| 10108 | $CH_2Cl$ |
| 10109 | $CHCl_2$ |
| 10110 | $CCl_3$ |
| 10111 | $CH_2F$ |
| 10112 | $OCH_3$ |
| 10113 | $OC_2H_5$ |
| 10114 | $OCH(CH_3)_2$ |
| 10115 | $OC(CH_3)_3$ |
| 10116 | $OCF_3$ |
| 10117 | $OCH_2CF_3$ |
| 10118 | $OCH_2F$ |
| 10119 | $OCHF_2$ |
| 10120 | $SCH_3$ |
| 10121 | $SC_2H_5$ |
| 10122 | $SCH_2CH=CH_2$ |
| 10123 | $CH=CH_2$ |
| 10124 | $CH_2CH=CH_2$ |
| 10125 | $CH_2CH=CCl_2$ |
| 10126 | $C\equiv CH$ |
| 10127 | $CH_2C\equiv CH$ |
| 10128 | $CH_2C\equiv C-I$ |
| 10129 | $CH_2OCH_3$ |
| 10130 | $CH_2OCH_2CH_3$ |
| 10131 | $CH_2CH_2OCH_3$ |
| 10132 | $CH_2CH_2OCH_2CH_3$ |
| 10133 | $CH_2OCH_2Cl$ |
| 10134 | $CH_2OCH_2CH_2Cl$ |
| 10135 | $CH_2CH_2OCH_2Cl$ |
| 10136 | $CH_2SCH_3$ |
| 10137 | $CH_2SCH_2CH_3$ |
| 10138 | $CH_2CH_2SCH_3$ |
| 10139 | $CH_2CH_2SCH_2CH_3$ |
| 10140 | $CH_2SCH_2Cl$ |
| 10141 | $CH_2SCH_2CH_2Cl$ |
| 10142 | $CH_2CH_2SCH_2Cl$ |
| 10143 | $SOCH_3$ |
| 10144 | $SOC_2H_5$ |
| 10145 | $SOCF_3$ |
| 10146 | $SOCH_2CF_3$ |
| 10147 | $SO_2CH_3$ |
| 10148 | $SO_2C_2H_5$ |
| 10149 | $SO_2CF_3$ |
| 10150 | $SO_2CH_2CF_3$ |
| 10151 | $SO_2NHCOCH_3$ |
| 10152 | $SO_2NHCH_3$ |
| 10153 | $SO_2N(CH_3)_3$ |
| 10154 | $CONHSO_2CH_3$ |
| 10155 | $COCH_3$ |
| 10156 | $COC_2H_5$ |
| 10157 | $CO-n-C_3H_7$ |
| 10158 | $CO-i-C_3H_7$ |
| 10159 | $CO-n-C_4H_9$ |
| 10160 | $CO-i-C_4H_9$ |
| 10161 | $CO-t-C_4H_9$ |
| 10162 | $COCF_3$ |
| 10163 | $COCH_2Cl$ |
| 10164 | $COOCH_3$ |

TABLE 105-continued

| No. | $R_4$ |
|---|---|
| 10165 | $COOC_2H_5$ |
| 10166 | $COO-n-C_3H_7$ |
| 10167 | $COO-t-C_4H_9$ |
| 10168 | $COOCF_3$ |
| 10169 | $COOCH_2CH_2Cl$ |
| 10170 | $COOCH_2CF_3$ |
| 10171 | $CH_2COOCH_3$ |
| 10172 | $CH_2COOC_2H_5$ |
| 10173 | $CH_2COCH_3$ |
| 10174 | $CH_2COC_2H_5$ |
| 10175 | $CONHCH_3$ |
| 10176 | $CONHC_2H_5$ |
| 10177 | $CONH-t-C_4H_9$ |
| 10178 | $CON(CH_3)_2$ |
| 10179 | $CON(C_2H_5)_2$ |
| 10180 | $COOCH_2CH=CH_2$ |
| 10181 | $COOCH_2C\equiv CH$ |
| 10182 | $COOCH_2OCH_3$ |
| 10183 | $COOCH_2CH_2OCH_3$ |
| 10184 | $SNHCH_3$ |
| 10185 | $SNHC_2H_5$ |
| 10186 | $SN(CH_3)_2$ |
| 10187 | $SN(CH_2H_5)_2$ |
| 10188 | 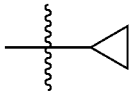 [SMILES: *C1CC1] |
| 10189 | 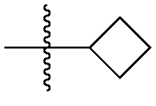 [SMILES: *C1CCC1] |
| 10190 | 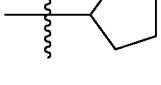 |
| 10191 | 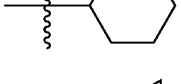 |
| 10192 | 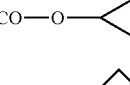 |
| 10193 | 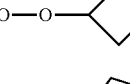 |
| 10194 | 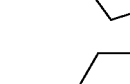 |
| 10195 | 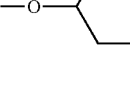 |
| 10196 | 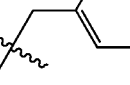 |
| 10197 | 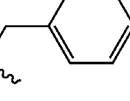 |

TABLE 105-continued
| No. | R4 |
|---|---|
| 10198 | 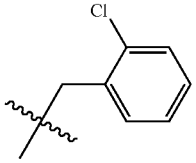 [SMILES: *Cc1ccccc1Cl] |
| 10199 | 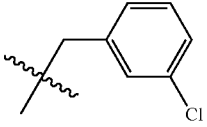 [SMILES: *Cc1cccc(Cl)c1] |
| 10200 | 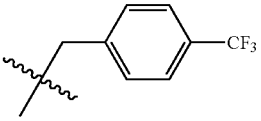 [SMILES: *Cc1ccc(C(F)(F)F)cc1] |
| 10201 | 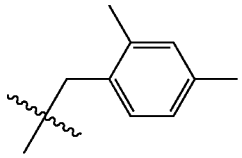 [SMILES: *Cc1ccc(C)cc1C] |
| 10202 | 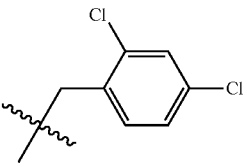 [SMILES: *Cc1ccc(Cl)cc1Cl] |
| 10203 | 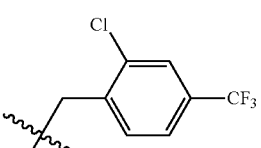 |
| 10204 | 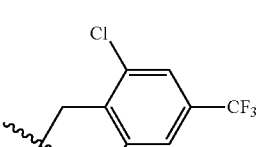 |
| 10205 | 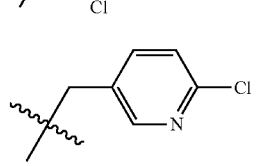 |
| 10206 | 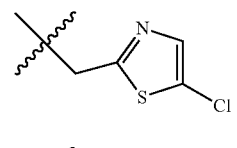 |
| 10207 | 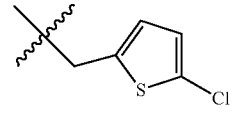 [SMILES: *Cc1ccc(Cl)s1] |
| 10208 | 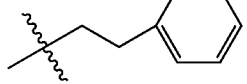 |
| 10209 | 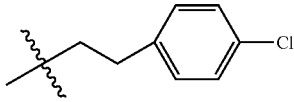 [SMILES: *CCc1ccc(Cl)cc1] |
| 10210 | 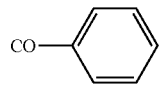 |
| 10211 | 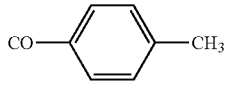 |
| 10212 | 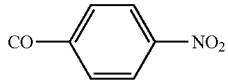 |
| 10213 |  |
| 10214 | 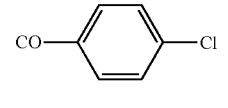 |
| 10215 | 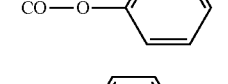 |
| 10216 | 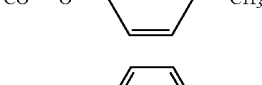 |
| 10217 | 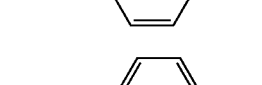 |
| 10218 | 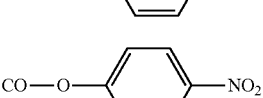 |
| 10219 |  |
| 10220 | 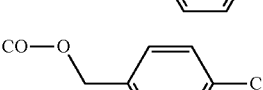 |
| 10221 | 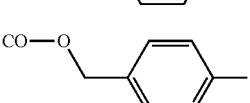 |
| 10222 |  |

TABLE 105-continued

| No. | R₄ |
|---|---|
| 10223 | CO—O—CH₂—C₆H₄—CF₃ (4-CF₃ benzyl ester) |
| 10224 | CO—O—CH₂—C₆H₄—NO₂ (4-NO₂ benzyl ester) |
| 10225 | CO—O—CH₂—C₆H₄—OCH₃ (4-OCH₃ benzyl ester) |
| 10226 | —CH₂—C(=O)—C₆H₅ (with gem-dimethyl) |
| 10227 | —CH₂—C(=O)—C₆H₄—CH₃ (4-methyl) |
| 10228 | —CH₂—C(=O)—C₆H₄—Cl (4-Cl) |
| 10229 | —CH₂—C(=O)—C₆H₄—Br (4-Br) |
| 10230 | —CH₂CH₂—C(=O)—C₆H₅ |
| 10231 | —CH₂CH₂—C(=O)—C₆H₄—Cl (4-Cl) |

Table 106: In general formula IB, $R_1=C_2H_5$, $R_2=Cl$, $R_3=R_5=R_6=H$, $(R_{10})n=4$-Cl, the substituents $R_4$ refer to Table 105, the representative compounds are coded as 10232-10371.

Table 107: In general formula IB, $R_1=CH_3$, $R_2=Cl$, $R_3=CH_3$, $R_5=R_6=H$, $(R_{10})n=4$-Cl, the substituents $R_4$ refer to Table 105, the representative compounds are coded as 10372-10511.

Table 108: In general formula IB, $R_1=CH_3$, $R_2=Cl$, $R_3=R_5=R_6=H$, $(R_{10})n=4$-OCF$_3$, the substituents $R_4$ refer to Table 105, the representative compounds are coded as 10512-10651.

Table 109: In general formula IC, $R_1=C_2H_5$, $R_2=Cl$, $R_3=R_5=R_6=R_{15}=R_{16}=R_{17}=R_{18}=H$, the substituents $R_4$ refer to Table 105, the representative compounds are coded as 10652-10791.

Table 110: In general formula ID, $R_1=C_2H_5$, $R_2=Cl$, $R_3=R_5=R_6=H$, $(R_{10})n=4$-Cl, the substituents $R_4$ refer to Table 105, the representative compounds are coded as 10792-10931.

The salts of some compounds having a structure as represented by formula II of the present invention are listed in Table 111, but without being restricted thereby.

TABLE 111 the salts of some compounds

| No. | structure |
|---|---|
| 10932 | 6-ethyl-5-chloro-pyrimidin-4-yl-NH-CH₂CH₂-[1-(4-chlorophenyl)pyrazol-4-yl] · HCl |
| 10933 | 6-ethyl-5-chloro-pyrimidin-4-yl-NH-CH₂CH₂-[1-(4-chlorophenyl)pyrazol-4-yl] · HNO₃ |
| 10934 | (6-ethyl-5-chloro-pyrimidin-4-yl-NH-CH₂CH₂-[1-(4-chlorophenyl)pyrazol-4-yl])₂ · H₂SO₄ |

TABLE 111-continued
the salts of some compounds
| No. | structure |
|---|---|
| 10935 | 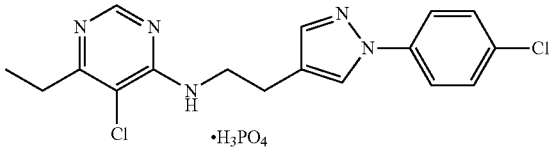 ·H$_3$PO$_4$ |
| 10936 | 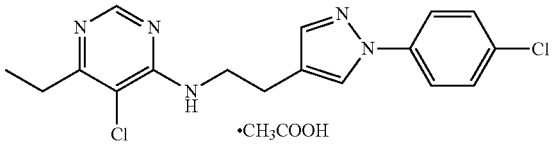 ·CH$_3$COOH |
| 10937 | 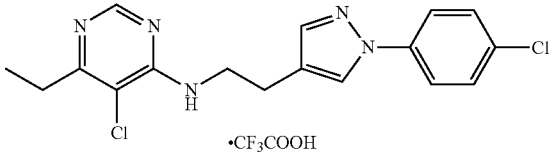 ·CF$_3$COOH |
| 10938 | 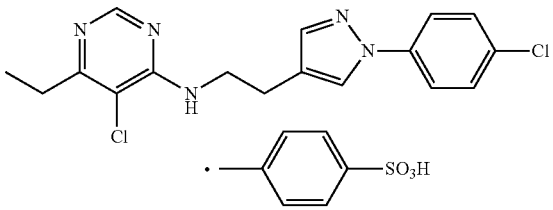 |
| 10939 | 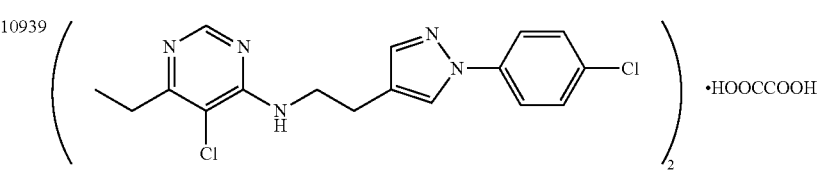 ·HOOCCOOH |
| 10940 | 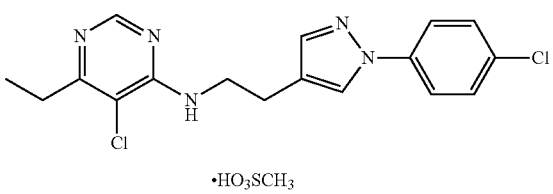 ·HO$_3$SCH$_3$ |
| 10941 | 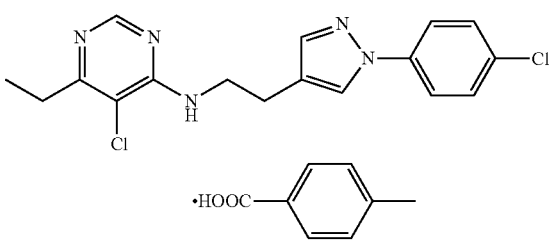 |
| 10942 | 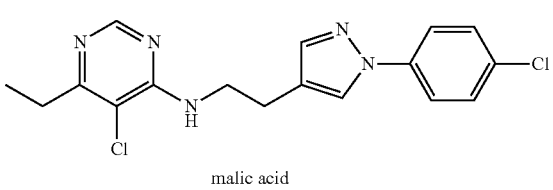 [SMILES: CCc1ncnc(NCCc2cnn(-c3ccc(Cl)cc3)c2)c1Cl ; "malic acid"] malic acid |

TABLE 111-continued
the salts of some compounds
| No. | structure |
|---|---|
| 10943 | 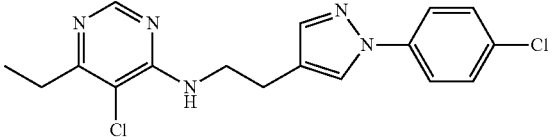<br>•maleic acid |
| 10944 | 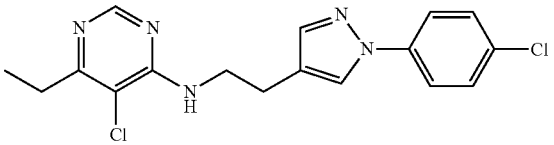<br>•citric acid |
| 10945 | 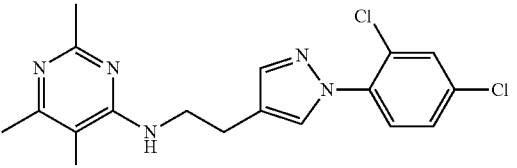<br>•HCl |
| 10946 | 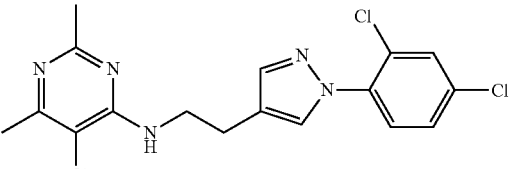<br>•HNO$_3$ |
| 10947 | 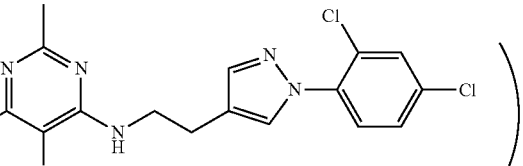<br>•H$_2$SO$_4$ |
| 10948 | 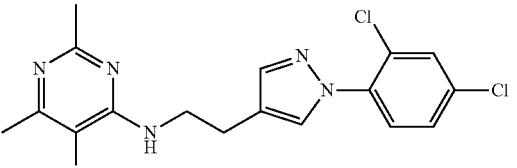<br>•H$_3$PO$_4$ |
| 10949 | 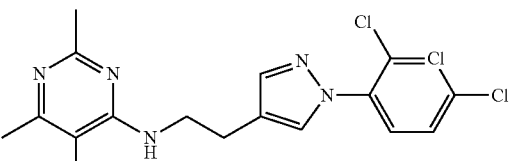<br>•CH$_3$COOH |

TABLE 111-continued
the salts of some compounds
| No. | structure |
|---|---|
| 10950 | 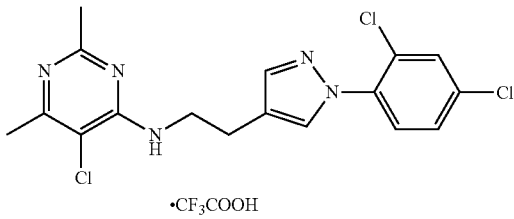 [SMILES: Cc1nc(C)c(Cl)c(NCCc2cnn(-c3ccc(Cl)cc3Cl)c2)n1 ; "·CF3COOH"]•CF$_3$COOH |
| 10951 | 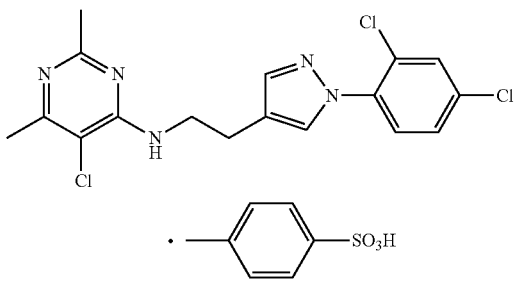 [SMILES: Cc1nc(C)c(Cl)c(NCCc2cnn(-c3ccc(Cl)cc3Cl)c2)n1 ; Cc1ccc(S(=O)(=O)O)cc1]•⟨tolyl⟩—SO$_3$H |
| 10952 | (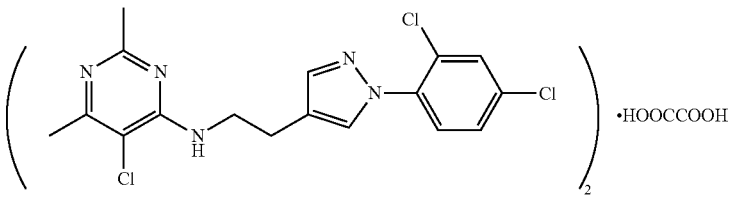)$_2$ •HOOCCOOH |
| 10953 | 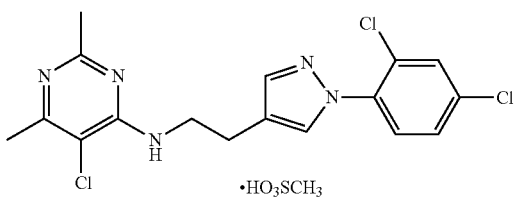•HO$_3$SCH$_3$ |
| 10954 | 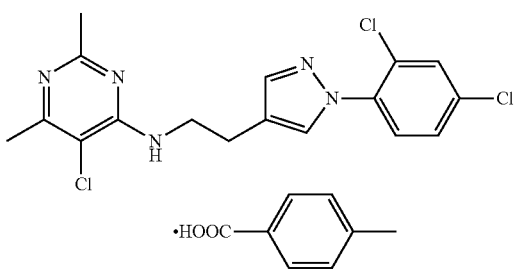•HOOC—⟨tolyl⟩ |
| 10955 | 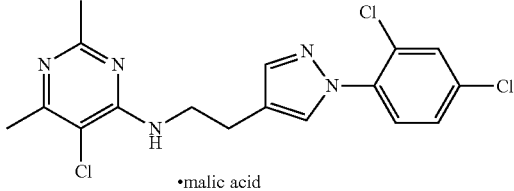•malic acid |

US 9,682,962 B2
TABLE 111-continued
the salts of some compounds
| No. | structure |
|---|---|
| 10956 | 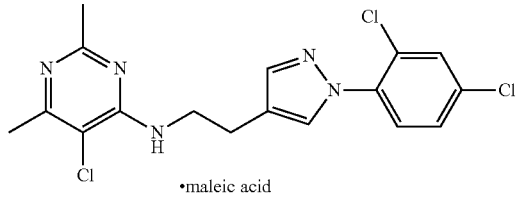 •maleic acid |
| 10957 | 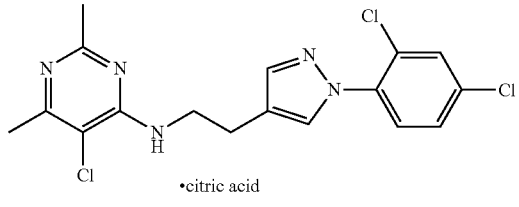 •citric acid |
| 10958 | 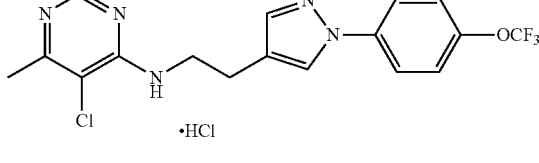 •HCl |
| 10959 | 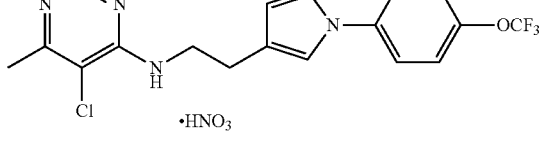 •HNO$_3$ |
| 10960 | (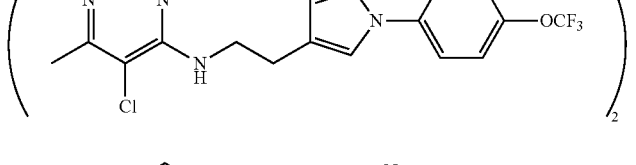)$_2$ •H$_2$SO$_4$ |
| 10961 | 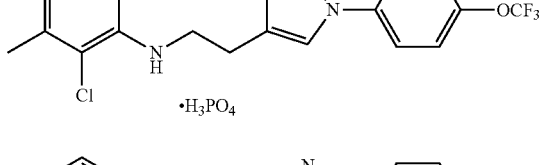 •H$_3$PO$_4$ |
| 10962 | 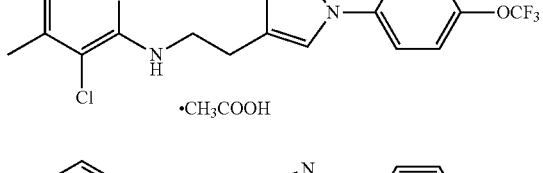 •CH$_3$COOH |
| 10963 | 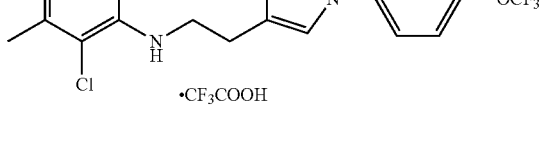 •CF$_3$COOH |

TABLE 111-continued
the salts of some compounds
| No. | structure |
|---|---|
| 10964 | 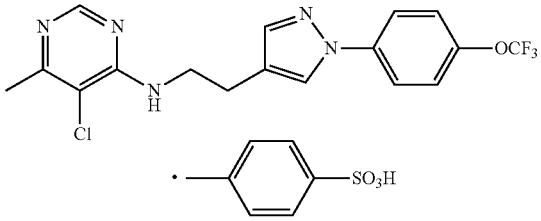 |
| 10965 | 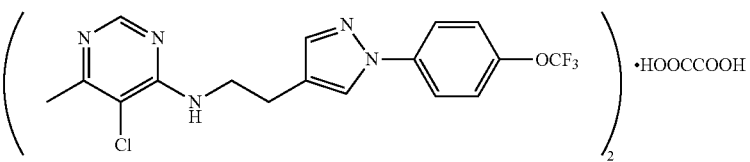 |
| 10966 | 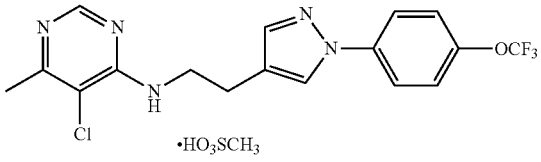 |
| 10967 | 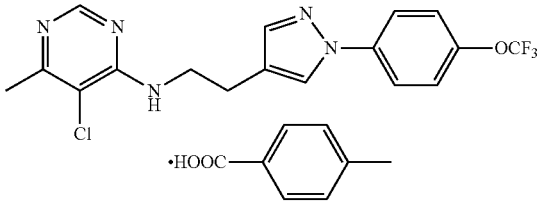 |
| 10968 | 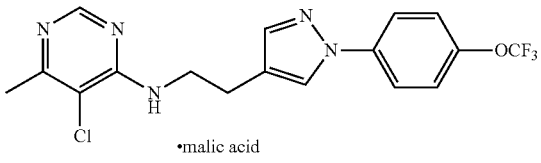 |
| 10969 | 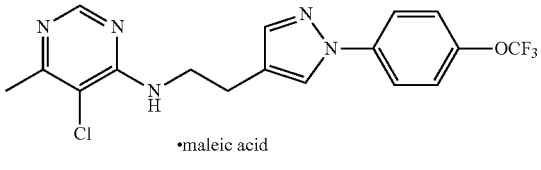 |
| 10970 | 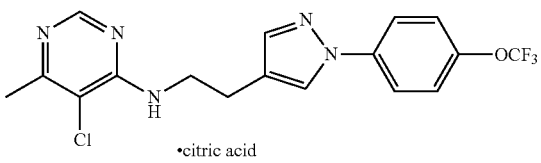 |

The compounds of the present invention can be prepared according to the following methods, the definition of each substituent is as defined above unless otherwise stated. The compounds represented by general formula I-1 ($R_4$=H) and general formula I-2 ($R_4 \neq$H) can be divided according to the difference of the substituent $R_4$:

The first method to prepare the compounds represented by general formula I-1 is as follows when $R_4$ is H:

The compounds represented by general formula I-1 can be prepared by reaction of intermediates II and III in the presence of proper base, the preparation methods are shown as follows. The detailed operation procedures refer to the methods described in EP0370704, EP0356158, EP0264217, EP0665225, JP10036355, U.S. Pat. No. 4,985,426 and so on.

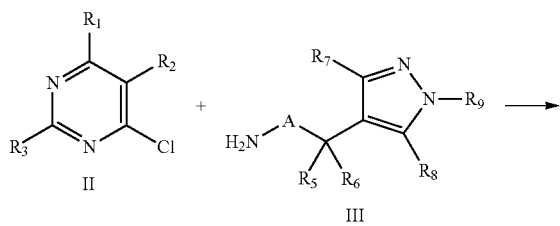

The reaction was carried out in proper solvent and the proper solvent mentioned may be selected from tetrahydrofuran, 1,4-dioxane, acetonitrile, toluene, xylene, benzene, DMF, N-methyl pyrrolidone, DMSO, acetone or butanone and so on.

The proper temperature mentioned is from room temperature to boiling point of the solvent, normal temperature is from 20° C. to 100° C.

The reaction time is in the range of 30 minutes to 20 hours, generally being 1-10 hours.

Intermediates II are commercially available, or are prepared according to the methods described in JP2000007662, U.S. Pat. Nos. 4,977,264, 6,090,815, US20040092402, JP09124613, U.S. Pat. Nos. 5,468,751, 4,985,426, 4,845,097, *Recueil des Travaux Chimiques des Pays-Bas* (1978), 97 (11), Pages 288-92, Journal of the American Chemical Society, 79, 1455(1957) or Journal of Chemical Society, p. 3478-3481 (1955).

The intermediate represented by general formula III is the key intermediate which is used to prepare the compounds represented by general formula I-1. According to the definition of A, the two preparation methods are as follows:

(1) When A is —$CH_2$—, the preparation method is as follows:

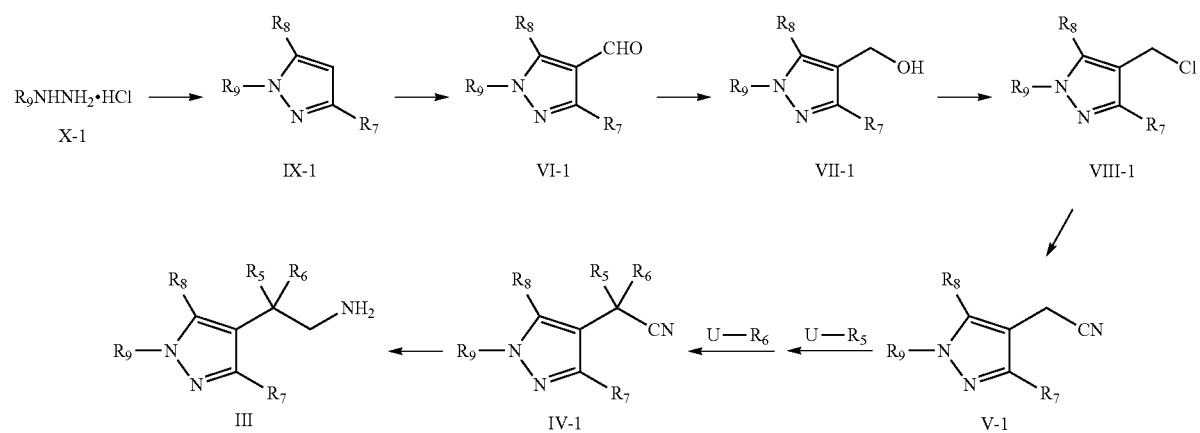

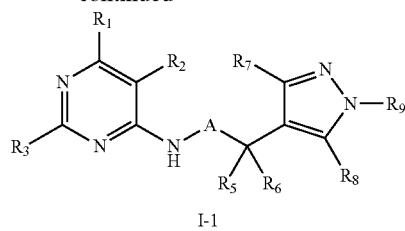

The compounds represented by general formula I-1 can be prepared by reaction of intermediates II and III in the presence of proper base and solvent.

The proper base mentioned may be selected from potassium hydroxide, sodium hydroxide, sodium carbonate, potassium carbonate, sodium bicarbonate, triethylamine, pyridine, sodium methoxide, sodium ethoxide, sodium hydride, potassium tert-butoxide or sodium tert-butoxide and so on.

Wherein, the leaving group U is halogen or hydroxy and so on.

The intermediates represented by general formula IX-1 can be prepared by reaction of intermediates represented by general formula X-1 with 1,1,3,3-tetramethoxypropane in proper solvent and temperature in the presence of proper base. The reaction time is in the range of 30 minutes to 20 hours, generally being 1-10 hours, the detailed operation procedures refer to the methods described in Bioorg. Med. Chem. 11 (2003) 4807-4813 and Bioorg. Med. Chem. 17 (2009) 295-302. The intermediates represented by general formula VI-1 can be prepared from intermediates represented by general formula IX-1 by Vilsmerier reaction, the detailed operation refers to the methods described in Bioorg. Med. Chem. 11 (2003) 4807-4813 and Bioorg. Med. Chem. 17 (2009) 295-302. The intermediates represented by general formula VII-1 can be prepared by reaction of intermediates represented by general formula VI-1 and sodium borohydride according to known methods. The intermediates represented by general formula VIII-1 can be prepared by reaction of intermediates represented by general formula VII-1 and sulfoxide chloride according to known methods. The intermediates represented by general formula V-1 can be prepared by reaction of intermediates represented by general formula VIII-1 and sodium cyanide according to the methods described in WO2007045989 and WO2009115257. According to the methods described in Journal of Organic Chemistry, 71(21), 8023-8027; 2006, Synthesis, (24), 4242-4250, 2010, Heterocycles, 56 (1-2), 443-455, 2002 or ARKIVOC (Gainesville, Fla., United States) [online computer file], (10), 40-51, 2002, the intermediates represented by general formula IV-1 can be prepared via intermediate V-1. Finally, the intermediates represented by general formula III-1 can be prepared by reaction of intermediates represented by general formula IV-1 and ammonia water in the presence of proper catalyst by using hydrogenation reduction. The detailed operation refers to the methods described in J. Am. Chem. Soc, 70, 3788(1948); 82, 681 (1960); 82, 2386(1960); Can. J. Chem, 49, 2990(1971); J. Org. Chem, 37, 335(1972); Organic Syntheses, Coll. Vol. 3, p. 229, p. 720 (1955), Vol. 23, p. 71 (1943) or Vol. 27, p. 18 (1947). The proper catalysts mentioned may be selected from Raney-nickel, palladium carbon or platinum oxide, etc.

The sources of intermediates are as follows: the intermediate represented by general formula X-1 are commercially available, or can be prepared according to the conventional method.

The proper base mentioned may be selected from potassium hydroxide, sodium hydroxide, sodium carbonate, potassium carbonate, sodium bicarbonate, triethylamine, pyridine, sodium methoxide, sodium ethoxide, sodium hydride, potassium tert-butoxide or sodium tert-butoxide and so on.

The reaction was carried out in proper solvent and the proper solvent mentioned may be selected from tetrahydrofuran, 1,4-dioxane, acetonitrile, toluene, xylene, benzene, DMF, N-methyl pyrrolidone, DMSO, acetone or butanone and so on.

The proper temperature mentioned is from room temperature to boiling point of the solvent, normal temperature is from 20° C. to 100° C.

The reaction time is in the range of 30 minutes to 20 hours, generally being 1-10 hours.

(2) When A is —$CH_2CH_2$—, the preparation method is as follows:

The intermediate IV-2 can be prepared by reaction with IV-1 according to the methods described in Synthesis, (9), 727-9; 1983 or Tetrahedron Letters, 39(51), 9455-9456; 1998; The preparation method of intermediate III-1 from IV-2 is the same as the corresponding steps when A is —$CH_2$—.

The second method to prepare the compounds represented by general formula I-2 is as follows when $R_4$ is other substituent except H.

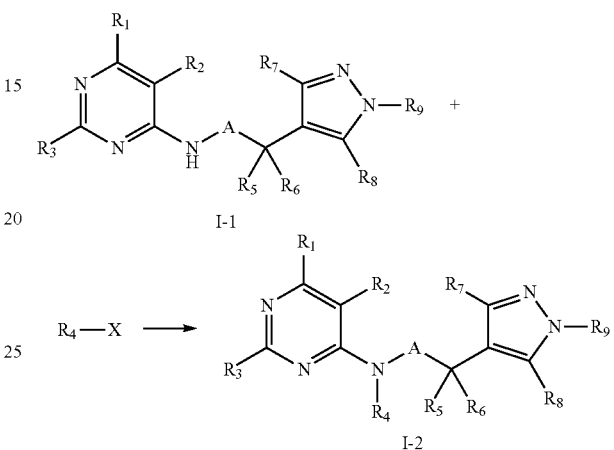

The detailed operation refers to the methods described in JP08269021, JP3543411, JP1995-72621, JP1995-96669, JP3511729, JP08291149, EP530149 and WO9208704.

The preparation method of the salts of the compounds represented by general formula I is as follows:

In the compounds represented by general formula I, the preparation of the salts of the pyrimidinamine moiety is as follows:

The corresponding salts represented by general formula I-P can be prepared by reaction of the compounds represented by general formula I with corresponding organic acids or inorganic acids, the reaction equation is as shown in the following.

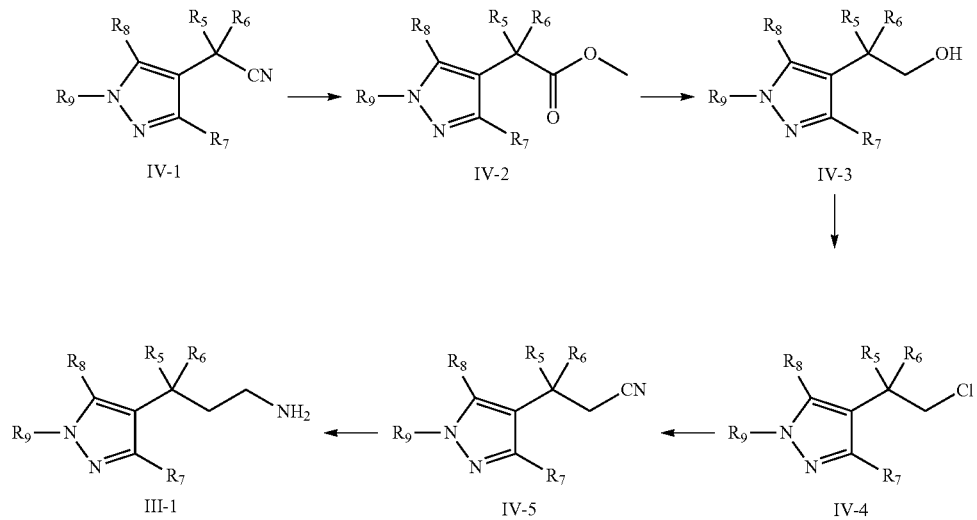

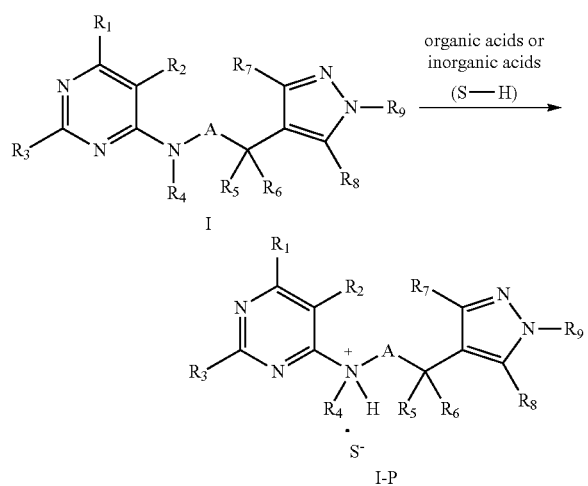

In addition, the salts I-P can also be formed based on nitrogen atom of pyrimidine ring or other nitro-containing heterocyclic ring in general formula I, the preparation methods refer to DE19647317, JP2001504473, U.S. Pat. No. 5,925,644, WO9822446 and ZA9710187, etc.

The forming salts reaction of compounds represented by general formula I with organic acids or inorganic acids can be carried out at room temperature to boiling point of the solvent, normal temperature is from 20° C. to 100° C. The reaction time is in the range of 30 minutes to 20 hours, generally being 1-10 hours. The proper solvent mentioned may be selected from water, methanol, ethanol, isopropanol, benzene, toluene, xylene, acetone, ethyl methyl ketone, methyl isobutyl ketone, chloroform, dichloromethane, methyl acetate, ethyl acetate, tetrahydrofuran, 1,4-dioxane, DMF, N-methyl pyrrolidone or DMSO and so on.

The acids which can be used to form salts with compounds represented by general formula I include hydrochloric acid, sulphuric acid, phosphorous acid, formic acid, acetic acid, trifluoroacetic acid, oxalic acid, methanesulfonic acid, p-toluenesulfonic acid, benzoic acid, phthalic acid, maleic acid, sorbic acid, malic acid or citric acid and so on. The further preferred acids are hydrochloric acid, sulphuric acid, phosphorous acid, trifluoroacetic acid, methanesulfonic acid or p-toluenesulfonic acid.

Although the compounds represented by general formula I and some compounds reported in prior art both belong to pyrazolyl pyrimidinamine compounds, there are still some obvious differences in structure between them. It is due to these differences in structure that lead to compounds of present invention with better fungicidal and/or insecticidal/acaricidal activities.

The compounds represented by general formula I show excellent activity against both many plant pathogens/diseases in agricultural and other fields and insects/mites. Therefore the technical scheme of the present invention also includes the uses of the compounds represented by general formula I to prepare fungicides, insecticides/acaricides in agricultural or other fields.

The present invention is explained by the following examples of plant diseases, but without being restricted thereby.

The compounds represented by general formula I can be used to control these plant diseases: Oomycete diseases, such as downy mildew (cucumber downy mildew, rape downy mildew, soybean downy mildew, downy mildew of beet, downy mildew of sugarcane, tobacco downy mildew, pea downy mildew, vegetable sponge downy mildew, chinese wax gourd downy mildew, muskmelon downy mildew, chinese cabbage downy mildew, spinach downy mildew, radish downy mildew, grape downy mildew, onion downy mildew), white rust (rape white rust, chinese cabbage white rust), damping-off disease (rape damping-off, tobacco damping-off, tomato damping-off, pepper damping-off, eggplant damping-off, cucumber damping-off, cotton damping-off), *pythium* rot (pepper soft stale disease, vegetable sponge cottony leak, chinese wax gourd cottony leak), blight (broad bean *phytophthora* blight, cucumber *phytophthora* blight, pumpkin *phytophthora* rot, chinese wax gourd *phytophthora* blight, watermelon *phytophthora* blight, muskmelon *phytophthora* blight, pepper *phytophthora* blight, chinese chives *phytophthora* blight, carlic *phytophthora* blight, cotton *phytophthora* blight), late blight (potato late blight, tomato late blight) and so on; diseases caused by Deuteromycotina, such as wilt disease (sweet potato *fusarium* wilt, cotton *fusarium* wilt disease, sesame wilt disease, *fusarium* wilt disease of costarbean, tomato *fusarium* wilt, bean *fusarium* wilt, cucumber *fusarium* wilt, vegetable sponge *fusarium* wilt, pumpkin *fusarium* wilt, chinese wax gourd *fusarium* wilt, watermelon *fusarium* wilt, muskmelon *fusarium* wilt, pepper *fusarium* wilt, broad bean *fusarium* wilt, *fusarium* wilt disease of rape, *fusarium* wilt disease of soybean), root rot (pepper root rot, eggplant root rot, bean *fusarium* root-rot, cucumber *fusarium* root rot, balsam pear *fusarium* root rot, cotton black root rot, broad bean thielaviopsis root rot), drooping disease (cotton soreshin, sesame soreshin, pepper *rhizoctonia* rot, cucumber *rhizoctonia* rot, chinese cabbage *rhizoctonia* rot), anthracnose (sorghum anthracnose, cotton anthracnose, kenaf anthracnose, jute anthracnose, flax anthracnose, tobacco anthracnose, mulberry anthracnose, pepper anthracnose, eggplant anthracnose, bean anthracnose, cucumber anthracnose, balsam pear anthracnose, summer squash anthracnose, chinese wax gourd anthracnose, watermelon anthracnose, muskmelon anthracnose, litchi anthracnose), *verticillium* wilt (cotton *verticillium* wilt, *verticillium* wilt of sunflower, tomato *verticillium* wilt, pepper *verticillium* wilt, eggplant *verticillium* wilt), scab (summer squash scab, chinese wax gourd scab, muskmelon scab), gray mold (cotton boll gray mold, kenaf gray mold, tomato gray mold, pepper gray mold, bean gray mold, celery gray mold, spinach gray mold, kiwi fruit gray mold rot), brown spot (cotton brown spot, jute brown spot, beet sercospora leaf spot, peanut brown spot, pepper brown leaf spot, chinese wax gourd *corynespora* leaf spot, soybean brown spot, sunflower brown spot, pea ascochyta blight, broad bean brown spot), black spot (flax black spot, rape *alternaria* leaf spot, sesame black spot, sunflower *alternaria* leaf spot, costarbean *alternaria* leaf spot, tomato nail head spot, pepper black fruit spot, eggplant black spot, bean leaf spot, cucumber *alternaria* blight, celery *alternaria* black leaf spot, carrot *alternaria* black rot, carrot leaf blight, apple *alternaria* rot, peanut brown spot), spot blight (tomato *septoria* leaf spot, pepper *septoria* leaf spot, celery late blight), early blight (tomato early blight, pepper early blight, eggplant early blight, potato early blight, celery early blight), ring spot (soybean zonate spot, sesame ring spot, bean zonate spot), leaf blight (sesame leaf blight, sunflower leaf blight, watermelon *alternaria* blight, muskmelon *alternaria* spot), basal stein rot (tomato basal stem rot, bean *rhizoctonia* rot), and others (corn northern leaf spot, kenaf damping-off, rice blast, millet black sheath, sugarcane eye spot, cotton *aspergillus* boll rot, peanut crown rot, soybean stein blight, soybean black spot, muskmelon *alternaria* leaf blight, peanut web blotch, tea red leaf spot, pepper *phyllosticta* blight, chinese wax gourd *phyllosticta* leaf spot, celery black rot, spinach heart rot, kenaf leaf mold, kenaf brown leaf spot, Jute stem blight, soybean *cercospora* spot, sesame leaf spot, costarbean gray leaf spot, tea brown leaf spot, eggplant *cercospora* leaf spot, bean *cercospora* leaf spot, balsam pear *cercospora* leaf spot, watermelon *cercospora* leaf spot, jute dry rot, sunflower root and stein rot, bean charcoal rot, soybean target spot, eggplant *corynespora* leaf spot, cucumber *corynespora* target leaf spot, tomato leaf mold, eggplant *fulvia* leaf mold, broad bean chocolate spot) and so on; diseases caused by Basidiomycete, such as rust (wheat stripe rust, wheat stem rust, wheat leaf rust, peanut rust, sunflower rust, sugarcane rust, chinese chives rust, onion rust, millet rust, soybean rust), smut (corn head smut, corn smut, sorghum silk smut, sorghum loose kernel smut, sorghum hard smut, sorghum smut, millet kernel smut, sugarcane smut, bean rust), and others (for example, wheat sheath blight and rice sheath blight) and so on; diseases caused by Ascomycete, such as powdery mildew (wheat powdery mildew, rape powdery mildew, powdery mildew of sesame, powdery mildew of sunflower, beet powdery mildew, eggplant powdery mildew, pea powdery mildew, vegetable sponge powdery mildew, pumpkin powdery mildew, summer squash powdery mildew, chinese wax gourd, muskmelon powdery mildew, grape powdery mildew, broad bean powdery mildew), *sclerotinia* rot (flax sclertiniose, rape sclertiniose, soybean sclertiniose, peanut sclertiniose, tobacco *sclerotinia* rot, pepper *sclerotinia* rot, eggplant *sclerotinia* rot, bean *sclerotinia* rot, pea *sclerotinia* rot, cucumber *sclerotinia* rot, balsam pear *sclerotinia* rot, chinese wax gourd *sclerotinia* rot, watermelon *sclerotinia* disease, celery stein rot), scab (apple scab, pear scab) and so on.

Especially, the compounds of the present invention exhibit very good control against corn southern rust, rice blast, cucumber gray mold and cucumber downy mildew at very low doses.

The compounds represented by general formula I can be used to control these insects: Coleoptera, such as *Acanthoscelides* spp., *Acanthoscelides obtectus, Agrilus planipennis, Agriotes* spp., *Anoplophora glabripennis, Anthonomus* spp., *Anthonomus grandis, Aphidius* spp., *Apion* spp., *Apogonia* spp., *Atacnius sprctulus, Atomaria linearis,* pygmy mangold beetle, *Aulacophore* spp., *Bothynoderes punctiventris, Bruchus* spp., *Bruchus pisorum, Cacoesia, Cacoesia* spp., *Callosobruchus maculatus, Carpophilus hemipteras, Cassida vittata, Ccrostcrna* spp., *Ccrotoma, Ccrotoma* spp., *Cerotoma trifur cata, Ceutorhynchus* spp., *Ceutorhynchus assimilis,* cabbage seedpod weevil, *Ceutorhynchus napi,* cabbage curculio, *Chaetocnema* spp., *Colaspis* spp., *Conoderus scalaris, Conoderus stigmosus, Conotrachelus nenuphar, Cotinus nitidis,* Green June beetle, *Crioceris asparagi, Cryptolestes ferrugincus,* rusty grainbeetle, *Cryptolestes pusillus, Cryptolestes turcicus* Turkish grain beetle, *Ctenicera* spp., *Curculio* spp., *Cyclocephala* spp., *Cylindrocpturus adspersus,* sunflower stem weevil, *Deporaus marginatus,* mango leaf-cutting weevil, *Dermestes lardarius, Dermestes maculates, Diabrotica* spp., *Epilachna varivcstis, raustinus cubae, Hylobius pales,* pales weevil, *Hypera* spp., *Hypera postica, Hyperdoes* spp., *Hyperodes* weevil, *Hypothenemus hampei, Ips* spp., engravers, *Lasioderma serricorne, Leptinotarsa decemlineata, Liogenys fuscus, Liogenys suturalis, Lissorhoptrus oryzophilus, Lyctus* spp., powder post beetles, *Maecolaspis joliveti, Megascelis* spp., *Melanotus communis, Meligethes* spp., *Meligethes aeneus,* blossom beetle, *Melolontha melolontha, Oberea brevis, Oberea linearis, Oryctes rhinoceros,* date palm beetle, *Oryzaephilus merca-* *tor,* merchant grain beetle, *Oryzaephilus surinamensis,* sawtoothed grain beetle, *Otiorhynchus* spp., *Oulema melanopus,* cereal leafbeetle, *Oulema oryzae, Pantomorus* spp., *Phyllophaga* spp., *Phyllophaga cuyabana, Phyllotreta* spp., *Phynchites* spp., *Popillia japonica, Prostephanus truncates,* larger grain borer, *Rhizopertha dominica,* lesser grain borer, *Rhizotrogus* spp., Eurpoean chafer, *Rhynchophorus* spp., *Scolytus* spp., *Shenophorus* spp. *Sitona lincatus,* pea leaf weevil, *Sitophilus* spp., *Sitophilus granaries,* granary weevil, *Sitophilus oryzae,* rice weevil, *Stegobium paniceum,* drugstore beetle, *Tribolium* spp., *Tribolium castaneum,* red flour beetle, *Tribolium confusum,* confused flour beetle, *Trogoderma variabile,* warehouse beetle and *Zabrus tenebioides.*

Dermaptera.

Dictyoptera, such as *Blattella germanica,* German cockroach, *Blatta orientalis, Parcoblatta pennylvanica, Periplaneta americana,* American cockroach, *Periplaneta australoasiae,* Australian cockroach, *Pcriplancta brunnca,* brown cockroach, *Periplaneta fuliginosa,* smokybrown cockroach, *Pyncoselus suninamensis,* Surinam cockroach and *Supella longipalpa,* brownbanded cockroach.

Diptera, such as *Aedes* spp., *Agromyza frontella,* alfalfa blotch leafminer, *Agromyza* spp., *Anastrepha* spp., *Anastrepha suspensa,* Caribbean fruit fly, *Anopheles* spp., *Batrocera* spp., *Bactrocera cucurbitae, Bactrocera dorsalis, Ceratitis* spp., *Ceratitis capitata, Chrysops* spp., *Cochliomyia* spp., *Contarinia* spp., *Culex* spp., *Dasineura* spp., *Dasineura brassicae, Delia* spp., *Delia platura,* seedcorn maggot, *Drosophila* spp., *Fannia* spp., *Fannia canicularis,* little house fly, *Fannia scalaris, Gasterophilus intestinalis, Gracillia perseae, Haematobia irritans, Hylemyia* spp., root maggot, *Hypoderma lineatum,* common cattle grub, *Liriomyza* spp., *Liriomyza brassica,* serpentine leafminer, *Melophagus ovinus, Musca* spp., muscid fly, *Musca autumnalis,* face fly, *Vusca domestica,* house fly, *Oestrus ovis,* sheep bot fly, *Oscinella frit, Pegomyia betae,* beet leafminer, *Phorbia* spp., *Psila rosae,* carrotrust fly, *Rhagoletis cerasi,* cherry fruit fly, *Rhagoletis pomonella,* apple maggot, *Sitodiplosis mosellana,* orange wheat blossom midge, *stomoxys* calcitruns, stable fly, *Tahanus* spp. and *Tipula* spp.

Hemiptera, such as *Acrosternum hilare,* green stink bug, *Blissus leucopterus,* chinch bug, *Calocoris norvegicus,* potato mirid, *Cimex hemipterus,* tropical bed bug, *Cimex lectularius,* bed hug, *Daghertus fasciatus, Dichelops furcatus, Dysdercus suturellus,* cotton stainer, *Edessa meditabunda, Eurygaster maura,* cereal bug, *Euschistus heros, Euschistus servus,* brown stink bug, *Helopeltis antonii, Helopeltis theivora,* tea blight plantbug, *Lagynotomus* spp., *Leptocorisa oratorius, Leptocorisa varicorni, Lygus* spp., plant bug, *Lygus hesperus,* western tarnished plant bug, *Maconellicoccus hirsutus, Neurocolpus longirostris, Nezara viridula,* southern green stink bug, *PhyLocoris* spp., *Phytocoris californicus, Phytocoris relativus, Piezodorus guildingi, Poecilocapsus lineatus,* fourlined plant bug, *Psallus vaccinicola, Pseudacysta perseae, Scaptocoris castanea* and *Triatoma* spp., bloodsuckingconenose bug, kissing bug.

Homoptera, such as *Acrythosiphonpisum,* pea aphid, *Adelges* spp., adelgids, *Aleurodes proletella, Aleurodicus disperses, Aleurothrixus flccosus,* woolly whitefly, *Aluacaspis* spp., *Amrasca bigutella bigutella, Aphrophora* spp., leafhopper, *Aonidiella aurantii,* California red scale, *Aphis* spp., *Aphis gossypii,* cotton aphid, *Aphis pomi,* apple aphid, *Aulacorthitm solan,* foxglove aphid, *Bemisia* spp., *Bemisia argentifolii, Bemisia tabaci,* sweetpotato whitefly, *Brachycolus noxius,* Russian aphid, *Brachycorynclia asparagi,* asparagus aphid, *Brevennia rehi, Brevicoryne brassicae,*

*Ceroplastes* spp., *Ceroplastes rubens*, red wax scale, *Chionaspis* spp., *Chrysomphalus* spp., *Coccus* spp., *Dysaphis plantaginea*, rosy apple aphid, *Empoasca* spp., *Eriosoma lanigerum*, woolly apple aphid, *Icerya purchasi*, cottony cushion scale, *Idioscopus nitidulus*, mango leafhopper, *Laodelphax striatellus*, smaller brown planthopper, *Lepidosaphes* spp., *Macrosiphum* spp., *Macrosiphum euphorbiae*, potato aphid, *Macrosiphum granarium*, English grain aphid, *Macrosiphum rosae*, rose aphid, *Macrosteles quadrilineatus*, aster leafhopper, *Mahanarva frimbiolata*, *Metopolophium dirhodum*, rose grain aphid, *Midis longicornis*, *Myzus persicae*, green peach aphid, *Nephotettix* spp., *Nephotettix cinctipes*, green leafhopper, *Nilaparvata lugens*, brown planthopper, *Parlatoria pergandii*, chaff scale, *Parlatoria ziziphi*, ebony scale, *Peregrinus maidis*, corn delphacid, *Philaenus* spp., *Phylloxera vitifoliae*, grape phylloxera, *Physokermes piceae*, spruce bud scale, *Planococcus* spp., *Pseudococcus* spp., *Pscudococcus brevipes*, pine apple mealybug, *Quadraspidiotus perniciosus*, San Jose scale, *Rhapalosiphum* spp., *Rhapalosiphum maida*, corn leaf aphid, *Rhapalosiphum padi*, oatbird-cherry aphid, *Saissetia* spp., *Saissetia oleae*, *Schizaphis graminum*, greenbug, *Sitobion avenge*, *Sogatella furcifera*, white-backed planthopper, *Therioaphis* spp., *Toumeyella* spp., *Toxoptera* spp., *Trialeurodes* spp., *Trialeurodes vaporariorum*, greenhouse whitefly, *Trialeurodes abutiloneus*, bandedwing whitefly, *Unaspis* spp., *Unaspis yanonensis*, arrowhead scale and *Zulia entreriana*.

Hymenoptera, such as *Acromyrrmex* spp., *Athalia rosae*, *Atta* spp., leafcutting ants, *Camponotus* spp., carpenter ant, *Diprion* spp., sawfly, *Formica* spp., *Iridomyrmex humilis*, Argentine ant, *Monomorium* ssp., *Monomorium minumum*, little black ant, *Monomorium pharaonis*, pharaoh ant, *Neodiprion* spp., *Pogonomyrmex* spp., *Polistes* spp., paper wasp, *Solenopsis* spp., *Tapoinoma sessile*, odorous house ant, *Tetranomorium* spp., pavement ant, *Vespula* spp., yellow jacket and *Xylocopa* spp., carpenter bee.

Isoptera, such as *Coptotcrmcs* spp., *Coptotermes curvignathus*, *Coptotermes frenchii*, *Coptotermes formosanus*, Formosan subterranean termite, *Cornitermes* spp., nasute termite, *Cryptotermes* spp., *Heterotermes* spp., desert subterranean termite, *Ileterotermes aureus*, *Kalotermes* spp., *Incistitermes* spp., *Macrotermes* spp., fungus growing termite, *Marginitermes* spp., *Microcerotermes* spp., harvester termite, *Microtermes obesi*, *Procornitermes* spp., *Reticulitermes* spp., *Reticulitermes banyulensis*, *Reticulitermes grassei*, *Reticulitermes flavipes*, *Reticulitermes hageni*, *Reticulitermes hesperus*, *Reticulitermes santonensis*, *Reticulitermes speratus*, *Reticulitermes tibialis*, *Reticulitermes virginicus*, *Schedorhinotermes* spp. and *Zootermopsis* spp.

Lepidoptera, such as *Achoea janata*, *Adoxophyes* spp., *Adoxophyes orana*, *Agrotis* spp., *Agrotis ipsilon*, *Alabama argillacea*, cotton leafworm, *Amorbia cuneana*, *Amyelosis transitella*, navel orangeworm, *Anacamptodes defectaria*, *Anarsia lineatella*, peach twig borer, *Anomis sabulijera*, jute looper, *Anticarsia gemmatalis*, velvetbean caterpillar, *Archips argyrospila*) (fruit tree leafroller, *Archips rosana*, rose leaf roller, *Argyrotaenia* spp., tortricid moths, *Argyrotaenia citrana*, orange tortrix, *Autographa gamma*, *Bonagota cranaodcs*, *Borbo cinnara*, rice leaf folder, *Bucculatrix thurberiella*, cotton leafperforator, *Caloptilia* spp., *Capua reticulana*, *Carposina niponensis*, peach fruit moth, *Chilo* spp., *Chlumetia transversa*, mango shoot borer, *Choristoneura rosaceana*, oblique banded leaf roller, *Chrysodeixis* spp., *Cnaphalocerus medinalis*, grass leafroller, *Colias* spp., *Conpomorpha cramerella*, *Cossus cossus*, *Crambus* spp., Sod webworms, *Cydia funebrana*, plum fruit moth, *Cydia molesta*, oriental fruit moth, *Cydia nignicana*, pea moth, *Cydia pomonella*, codling moth, *Darna diducta*, *Diaphania* spp., stem borer, *Diatraea* spp., stalk borer, *Diatraea saccharalis*, sugarcane borer, *Diatraea graniosella*, southwester corn borer, *Earias* spp., *Earias insulata*, Egyptian bollworm, *Earias vitella*, rough northern bollworm, *Ecdytopopha aurantianum*, *Elasmopalpus lignosellus*, lesser cornstalk borer, *Epiphysias postruttana*, light brown, apple moth, *Ephestia* spp., *Ephestia cautella*, almond moth, *Ephestia elutella*, tobbaco moth, *Ephestia kuehniella*, Mediterranean flour moth, *Epimeces* spp, *Epinotia aporema*, *Erionota thrax*, banana skipper, *Eupoecilia ambiguella*, grape berry moth, *Euxoa auxiliaris*, army cutworm, *Feltia* spp., *Gortyna* spp., *Grapholita molesta*, oriental fruit moth, *Hedylepta indicata*, bean leaf webber, *Helicoverpa* spp., *Helicoverpa armigera*, cotton bollworm, *Helicoverpa zea*, *Heliothis* spp., *Heliothis virescens*, tobacco budworm, *Hellula undalis*, cabbage webworm, *Indarbela* spp. *Keiferia lycopersicella*, tomato pinworm, *Leucinodes orbonalis*, eggplant fruit borer, *Leucoptera malifoliella*, *Lithocollectis* spp., *Lobesia botrana*, grape fruit moth, *Loxagrotis* spp., *Loxagrotis albicosta*, western bean cutworm, *Lymantria dispar*, gypsy moth, *Lyonetia clerkella*, apple leafiminer, *Mahasena corbetti*, oil palm bagworm, *Malacosoma* spp., tent caterpillars, *Mamestra brassicae*, cabbage armywormn, *Maruca testulalis*, *Metisa plana*, *Mythimna unipuncta*, true armyworm, *Neoleucinodes elegantalis*, small tomato borer, *Nymphula depunctalis*, rice caseworm, *Operophthera brumata*, winter moth, *Ostrinia nubilalis*, European corn borer, *Oxydia vesulia*, *Pandemis cerasana*, common currant tortrix, *Pandemis heparana*, brown apple tortrix, *Papilio demodocus*, *Pectinophora gossypiella*, pink bollworm, *Peridroma* spp., *Peridroma saucia*, variegated cutworm, *Perileucoptera coffeella*, white coffee leafininer, *Phthorimaea operculella*, potato tuber moth, *Phyllocnisitis citrella*, *Phyllonorycter* spp., *Pieris rapae*, imported cabbageworm, *Plathypena scabra*, *Plodia interpunctella*, Indian meal moth, *Plutella xylostella*, diamondback moth, *Polychrosis viteana*, grape berry moth, *Prays endocarps*, *Prays oleae*, olive moth, *Pseudaletia* spp., *Pseudaletia unipunctata*, *Pseudoplusia includens*, soybean looper, *Rachiplusia nu*, *Scirpophaga incertulas*, *Sesamia* spp., *Sesamia inferens*, pink rice stemborer, *Sesamia nonagrioides*, *Setora nitens*, *Sitotroga cerealella*, Angoumois grain moth, *Sparganothis pilleriana*, *Spodoptera* spp., *Spodoptera exigua*, beet armyworm, *Spodoptera fugipcrda*, fall armyworm, *Spodoptera oridania*, southern armyworm, *Synanthedon* spp., *Thecla basilides*, *Thermisia gemmatalis*, *Tineola bisselliella*, webbing clothes moth, *Trichoplusia ni*, cabbage looper, *Tuts absoluta*, *Yponomeuta* spp., *Zeuzera coffeae*, red branch borer and *Zeuzera pyrina*, eopard moth.

Mallophaga, chewing lice, such as *Bovicola ovis*, sheep biting louse, *Menacanthus stramineus*, chicken body louse and *Menopon gallinea*, common hen house, Orthoptera, such as *Anabrus simplex*, Mormon cricket, Gryllotalpidae, mole cricket, *Locusta migratoria*, *Melanoplus* spp., *Microcentrum retinerve*, angular winged katydid, *Pterophylla* spp., histocerca gregaria, *Scudderia furcata*, fork tailed bush katydid and *Valanga nigricorni*, sucking louse, such as *Haematopinus* spp., *Linognathus ovillus*, sheep louse, *Pediculus humanus capitis*, *Pediculus humanus humanus* and *Pthirus pubis*, crab louse.

Siphonaptera, such as *Ctenocephal ides canis*, dog flea, *Ctenocephalides felis*, cat flea and *Pulex irritans* human flea.

Thysanoptera, such as *Frankliniella fuisca*, tobacco thrip, *Frankliniella occidentalis*, western flower thrips, *Frankliniella shultzei*, *Frankliniella williamsi*, corn thrip, *Ileliothrips* haemorrhaidalis, greenhouse thrip, *Riphiphorothrips cruentatus, Scirtothrips* spp, *Scirtothrips cirri*, citrus thrip, *Scirtothrips dorsalis*, yellow tea thrips, *Taeniothrips rhopalantennalis* and *Thrips* spp.

Thysanura, bristletail, such as *Lepisma* spp, silverfish and *Thermobia* spp.

Acarina, mite and tick, such as *Acarapsis woodi*, tracheal mite of honeybee, *Acarus* spp., *Acarus siro*, grain mite, *Aceria mangiferae*, mango bud mite, *Aculops* spp., *Aculops lycopersici*, tomato russet mite, *Aculops pelekasi, Aculus pelekassi, Aculus schlechtendali*, apple rust mite, *Amblyomma amecricanum*, lone star tick, *Boophilus* spp., *Brevipalpus obovatus*, privet mite, *Brevipalpus phoenicis*, red and black flat mite, *Demodex* spp., mange mites, *Dermacentor* spp., *Dermacentor variabilis*, american dog tick, *Dermatophagoides pteronyssinus*, house dust mite, *Eotetranycus* spp., *Eotetranychus carpini*, yellow spider mite, *Epitimerus* spp., *Eriophyes* spp., *Iodes* spp., *Metatetranycus* spp., *Notoedres cati, Oligonychus* spp., *Oligonychus* coffee, *Oligonychus ilicus*, southernred mite, *anonychus* spp., *Panonychus* cirri, citrus red mite, *Panonychus ulmi*, European red mite, *Phyllocoptruta oleivora*, citrus rust mite, *Polyphagotarsonemun latus*, broad mite, *Rhipicephalus sanguineus*, brown dog tick, *Rhizoglyphus* spp., bulb mite, *Sarcoptes scabiei*, itch mite, *Tegolophus perseaflorae, Tetranychus* spp., *Tetranychus urticae*, twospotted spider mite and *Varroa destructor.*

Nematoda, such as *Aphelenchoides* spp., bud and leaf & pine wood nematode, *Belonolaimus* spp., sting nematodes, *Criconemella* spp., ring nematodes, *Dirofilaria immitis*, dog heartworm, *Ditylenchus* spp., *Heterodera* spp., cyst nematode, *Heterodera zeae*, corn cyst nematode, *Hirschmanniella* spp., root nematodes, *Hoplolaimus* spp., lance nematodes, *Meloidogyne* spp., *Meloidogyne incognita, Onchocerca volvulus*, hook-tail worm, *PraLylenchus* spp., lesion nematode, *Radopholus* spp., burrowing nematode and *Rotylenchus reniformis*, kidney-shaped nematode.

Symphyla, such as *Scutigerella immaculata.*

Especially, the compounds represented by the present invention provide excellent control effects against cucumber downy mildew, wheat powdery mildew and cucumber anthracnose at a lower dosage.

Thanks to their positive characteristics, the compounds mentioned above can be advantageously used in protecting crops of farming and gardening, domestic and breeding animals, as well as environments frequented by human beings from pathogens, insects and pest mites.

In order to obtain desired effect, the dosage of the compounds to be applied can vary with various factors, for example, the used compound, the protected crop, the type of harmful organism, the degree of infestation, the climatic conditions, the application method and the adopted formulation.

The dosage of compounds in the range of 10 g to 5 kg per hectare can provide a sufficient control.

A further object of the present invention also includes fungicidal, insecticidal/acaricidal compositions containing the compounds having general formula I as active ingredient, and the weight percentage of the active ingredient in the composition is 0.5-99%. The fungicidal, insecticidal/acaricidal compositions also include the carrier being acceptable in agriculture, forestry and public health.

The compositions of the present invention can be used in the form of various formulations. Usually, the compounds having general formula I as active ingredient can be dissolved in or dispersed in carriers or made to a formulation so that they can be easily dispersed as an fungicide or insecticide. For example: these chemical formulations can be made into wettable powder, oil miscible flowable, aqueous suspension, aqueous emulsion, aqueous solution or emulsifiable concentrates and so on. Therefore, in these compositions, at least a liquid or solid carrier is added, and usually suitable surfactant(s) can be added when needed.

Still also provided by the present invention are the application methods for controlling phytopathogenic fungi, insects, pest mites which is to apply the compositions of the present invention to the phytopathogenic fungi or their growing loci. The suitable effective dosage of the compounds of the present invention is usually within a range of 10 g/ha to 1000 g/ha, preferably from 20 g/ha to 500 g/ha.

For some applications, one or more other fungicides, insecticides/acaricides, herbicides, plant growth regulators or fertilizer can be added into the fungicidal, insecticidal/acaricidal compositions of the present invention to make additional merits and effects.

It should be noted that variations and changes are permitted within the claimed scopes in the present invention.

DETAILED DESCRIPTION OF THE INVENTION

The present invention is illustrated by the following examples, but without being restricted thereby. (All raw materials are commercially available unless otherwise specified.)

PREPARATION EXAMPLES

Example 1

The Preparation of Intermediate 4,5-dichloro-6-methylpyrimidine

1) The Preparation of 4-hydroxyl-5-chloro-6-methylpyrimidine

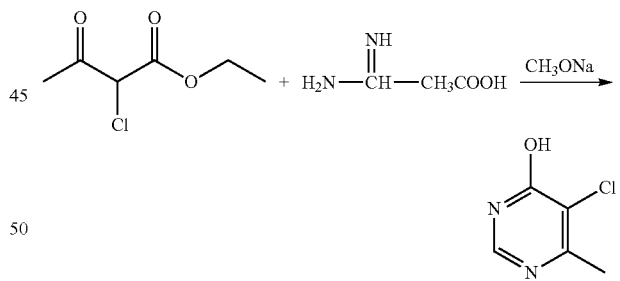

A solution of 8.80 g (0.16 mol) of CH$_3$ONa in methanol was added slowly to a solution of 11.30 g (0.11 mol) of formimidamide acetate in 50 mL of methanol at room temperature under stirring, the mixture was stirred for another 2 h after addition at room temperature. Followed by addition of 11.17 g (0.068 mol) of ethyl 2-chloro-3-oxobutanoate, the mixture was continued stirring for another 5-7 h at room temperature. After the reaction was over by Thin-Layer Chromatography monitoring, the reaction mixture was concentrated under reduced pressure and pH was adjusted to 5-6 with HCl, and then filtered to afford orange-yellow solid, the water phase was extracted with ethyl acetate (3×50 mL), dried over anhydrous magnesium sulfate, filtered and then concentrated under reduced pressure.

The residue was dissolved to 50 ml of ethyl acetate, stand overnight to obtain 6.48 g as orange-yellow solid with yield of 66%. m.p. 181~184° C.

2) The Preparation of Intermediate 4,5-dichloro-6-methylpyrimidine

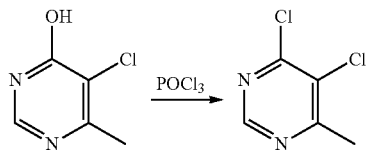

50 ml of POCl₃ was added dropwise to a solution of 14.5 g (0.1 mol) of 4-hydroxyl-5-chloro-6-methylpyrimidine in 50 mL of toluene, the mixture was refluxed for 5-7 h after addition. After the reaction was over by Thin-Layer Chromatography monitoring, the reaction mixture was concentrated under reduced pressure to remove toluene and extra POCl₃, and then poured into ice water. The water phase was extracted with ethyl acetate (3×50 mL), the organic phases were emerged, dried over anhydrous magnesium sulfate, filtered and then concentrated under reduced pressure. The residue was purified through silica column (ethyl acetate/petroleum ether=1:5, as an eluent) to give 14.43 g as yellow liquid with yield of 88.5%.

Example 2

The Preparation of Intermediate 2-(1-(4-chlorophenyl)-1H-pyrazol-4-yl)ethanamine 1) The Preparation of Intermediate 1-(4-chlorophenyl)-1H-pyrazole

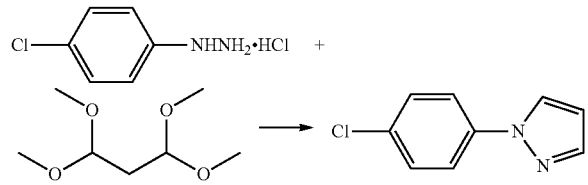

1,1,3,3-tetramethoxypropane (16.4 g, 0.1 mol) was added to a suspension of 4-chlorophenyl hydrazine hydrochloride (17.9 g, 0.1 mol) in 95% ethanol aqueous solution (100 mL) and the resulting mixture was heated to reflux for 3-5 h. After the reaction was over by Thin-Layer Chromatography monitoring, the reaction mixture was concentrated under reduced pressure to remove most of the ethanol, and then poured into sodium carbonate solution. The water phase was extracted with ethyl acetate (3×100 mL), the organic phases were emerged, dried over anhydrous magnesium sulfate, filtered and then concentrated under reduced pressure. The residue was purified through silica column (ethyl acetate/petroleum ether=1:10, as an eluent) to get 15.19 g 1-(4-chlorophenyl)-1H-pyrazole as yellow solid with yield of 85.1%.

2) The Preparation of Intermediate 1-(4-chlorophenyl)-1H-pyrazole-4-carbaldehyde

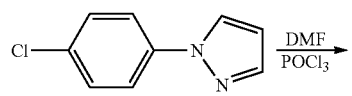

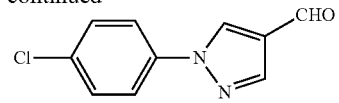

Phosphorus oxychloride (225 mL, 2.4 mol) was added slowly to anhydrous DMF (185 mL, 2.4 mol) at −5° C.-0° C. with mechanical stirring. After stirring the mixture for 30 minutes, 1-(4-chlorophenyl)-1H-pyrazole (107.1 g, 0.6 mol) was added to reaction mixture slowly and then reaction was heated at 90° C. for 15 h. After the reaction was over by Thin-Layer Chromatography monitoring, the reaction mixture was cooled to room temperature, then poured into the ice water and neutralized with sodium carbonate. The water phase was extracted with ethyl acetate (3×150 mL), the organic phases were emerged, dried over anhydrous magnesium sulfate, filtered and then concentrated under reduced pressure. The residue was purified through silica column (ethyl acetate/petroleum ether=1:5, as an eluent) to get 80.54 g 1-(4-chlorophenyl)-1H-pyrazole-4-carbaldehyde as white solid.

3) The Preparation of Intermediate (1-(4-chlorophenyl)-1H-pyrazol-4-yl)methanol

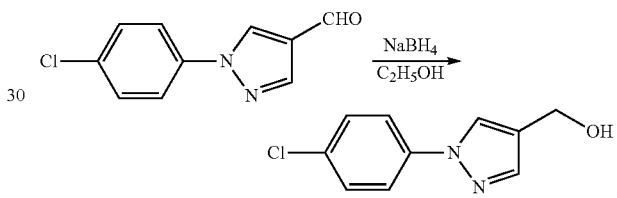

1-(4-chlorophenyl)-1H-pyrazole-4-carbaldehyde (20.6 g, 0.1 mol) was dissolved in 150 mL methanol and stirred in ice-bath. After stirring the mixture for 5 minutes, sodium borohydride (9.5 g, 0.25 mol) was added by portion and reacted at room temperature for 4-6 h. After the reaction was over by Thin-Layer Chromatography monitoring, most of the anhydrous ethanol was removed under reduced pressure, and then the mixture was poured into water, The water phase was extracted with ethyl acetate (3×50 mL), the organic phases were emerged, dried over anhydrous magnesium sulfate, filtered and then concentrated under reduced pressure. The residue was purified through silica column (ethyl acetate/petroleum ether=1:2, as an eluent) to get 20.12 g (1-(4-chlorophenyl)-1H-pyrazol-4-yl)methanol as white solid with yield of 96.5%.

4) The Preparation of Intermediate 4-(chloromethyl)-1-(4-chlorophenyl)-1H-pyrazole

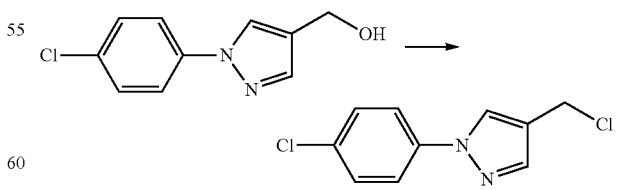

(1-(4-chlorophenyl)-1H-pyrazol-4-yl)methanol (20.85 g, 0.1 mol) was dissolved in 120 mL toluene, thionylchloride (14.28 g, 0.12 mol) wad added dropwise at room temperature, and then heated to reflux for 3-4 h. After the reaction was over by Thin-Layer Chromatography monitoring, the mixture was evaporated under reduced pressure to get 22.06 g crude 4-(chloromethyl)-1-(4-chlorophenyl)-1H-pyrazole (22.06 g) as pale red brown oil with yield of 97.2%.

5) The Preparation of Intermediate 2-(1-(4-chlorophenyl)-1H-pyrazol-4-yl)acetonitrile

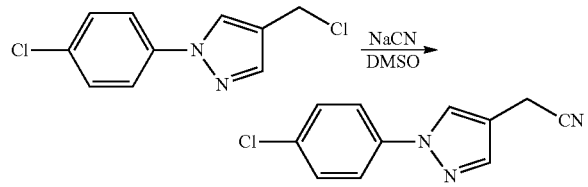

To a solution of sodium cyanide (5.88 g, 0.12 mol) dissolved in 100 mL dimethyl sulfoxide at 80° C. was added 22.7 g (0.1 mol) 4-(chloromethyl)-1-(4-chlorophenyl)-1H-pyrazole after 30 min and then reacted for 1-3 h. After the reaction was over by Thin-Layer Chromatography monitoring, the mixture was poured into water, The water phase was extracted with ethyl acetate (3×80 mL), the organic phases were emerged, dried over anhydrous magnesium sulfate, filtered and then concentrated under reduced pressure. The residue was purified through silica column (ethyl acetate/petroleum ether=1:4, as an eluent) to get 20.38 g 2-(1-(4-chlorophenyl)-1H-pyrazol-4-yl)acetonitrile as white solid with yield of 93.7%.

6) The Preparation of Intermediate 2-(1-(4-chlorophenyl)-1H-pyrazol-4-yl)ethanamine

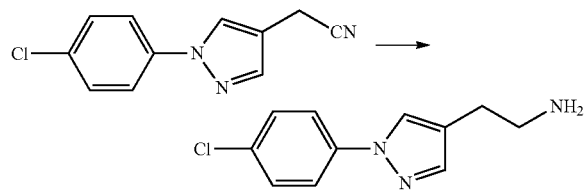

To a solution of 2-(1-(4-chlorophenyl)-1H-pyrazol-4-yl)acetonitrile 4.35 g (0.02 mol), Raney nickel (1.0 g) and 100 mL of 10% ammonia in methanol was filled with hydrogen at 40 Pa, then the reaction mixture was continued stirring at room temperature for 3 h and monitored by TLC until the reaction was over, Raney nickel was filtered, the solution was concentrated under reduced pressure to obtain 4.34 g target intermediate as sticky oil with yield of 98.0%.

Example 3

The Preparation of Intermediate 2-(1-(2,4-dichlorophenyl)-1H-pyrazol-4-yl)ethanamine 1) The Preparation of Intermediate 1-(2,4-dichlorophenyl)-1H-pyrazole

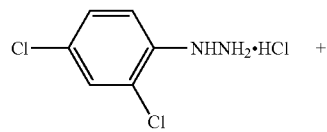

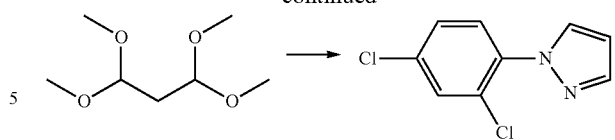

1,1,3,3-tetramethoxypropane (16.4 g, 0.1 mol) was added to a suspension of 2,4-dichlorophenyl hydrazine hydrochloride (21.35 g, 0.1 mol) in 95% ethanol aqueous solution (100 mL) and the resulting mixture was heated to reflux for 3-5 h. After the reaction was over by Thin-Layer Chromatography monitoring, the reaction mixture was concentrated under reduced pressure to remove most of the ethanol, and then poured into sodium carbonate solution. The water phase was extracted with ethyl acetate (3×100 mL), the organic phases were emerged, dried over anhydrous magnesium sulfate, filtered and then concentrated under reduced pressure. The residue was purified through silica column (ethyl acetate/petroleum ether=1:10, as an eluent) to get 18.06 g 1-(2,4-dichlorophenyl)-1H-pyrazole as yellow solid with yield of 84.8%.

2) The Preparation of Intermediate 1-(2,4-dichlorophenyl)-1H-pyrazole-4-carbaldehyde

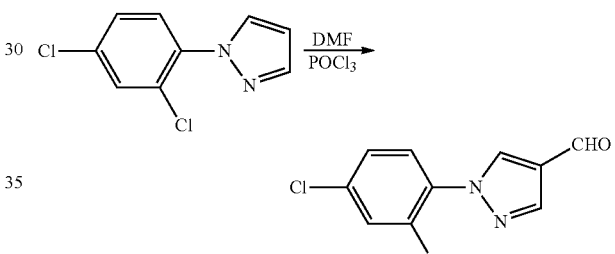

Phosphorus oxychloride (225 mL, 2.4 mol) was added slowly to anhydrous DMF (185 mL, 2.4 mol) at −5° C.-0° C. with mechanical stirring. After stirring the mixture for 10 minutes, 1-(2,4-dichlorophenyl)-1H-pyrazole (127.8 g, 0.6 mol) was added to reaction mixture slowly and then reaction was heated at 90° C. for 15 h. After the reaction was over by Thin-Layer Chromatography monitoring, the reaction mixture was cooled to room temperature, then poured into the ice water and neutralized with sodium carbonate. The water phase was extracted with ethyl acetate (3×150 mL), the organic phases were emerged, dried over anhydrous magnesium sulfate, filtered and then concentrated under reduced pressure. The residue was purified through silica column (ethyl acetate/petroleum ether=1:5, as an eluent) to get 98.33 g 1-(2,4-dichlorophenyl)-1H-pyrazole-4-carbaldehyde as white solid.

3) The Preparation of Intermediate (1-(2,4-dichlorophenyl)-1H-pyrazol-4-yl)methanol

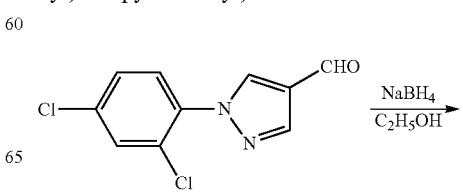

-continued

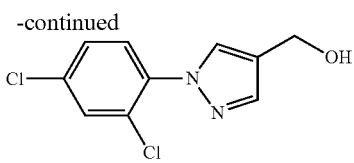

1-(2,4-dichlorophenyl)-1H-pyrazole-4-carbaldehyde (24.3 g, 0.1 mol) was dissolved in 1501 mL methanol and stirred in ice-bath. After stirring the mixture for 5 minutes, sodium borohydride (9.5 g, 0.25 mol) was added by portion and reacted at room temperature for 4-6 h. After the reaction was over by Thin-Layer Chromatography monitoring, most of the anhydrous ethanol was removed under reduced pressure, and then the mixture was poured into water, The water phase was extracted with ethyl acetate (3×50 mL), the organic phases were emerged, dried over anhydrous magnesium sulfate, filtered and then concentrated under reduced pressure. The residue was purified through silica column (ethyl acetate/petroleum ether=1:2, as an eluent) to get 23.38 g crude (1-(2,4-dichlorophenyl)-1H-pyrazol-4-yl)methanol as white solid with yield of 96.2%.

4) The Preparation of Intermediate 4-(chloromethyl)-1-(2,4-dichlorophenyl)-1H-pyrazole

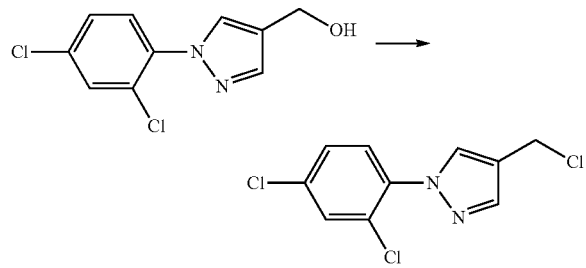

(1-(2,4-dichlorophenyl)-1H-pyrazol-4-yl)methanol (24.3 g, 0.1 mol) was dissolved in 120 mL toluene, thionylchloride (14.28 g, 0.12 mol) was added dropwise at room temperature, and then heated to reflux for 3-4 h. After the reaction was over by Thin-Layer Chromatography monitoring, the mixture was evaporated under reduced pressure to get 4-(chloromethyl)-1-(2,4-dichlorophenyl)-1H-pyrazole (25.7 g) as pale red brown oil with yield of 98.3%.

5) The Preparation of Intermediate 2-(1-(2,4-dichlorophenyl)-1H-pyrazol-4-yl)acetonitrile

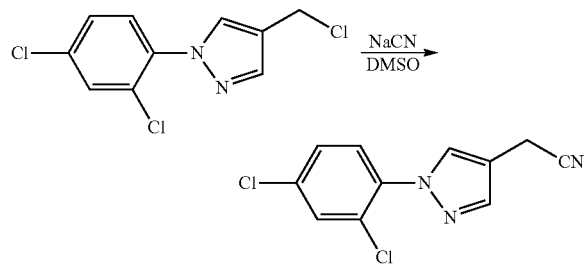

To a solution of sodium cyanide (5.88 g, 0.12 mol) dissolved in 100 mL dimethyl sulfoxide at 80° C. was added 22.7 g (0.1 mol) 4-(chloromethyl)-1-(2,4-dichlorophenyl)-1H-pyrazole after 30 min and then reacted for 1-3 h. After the reaction was over by Thin-Layer Chromatography monitoring, the mixture was poured into water, the water phase was extracted with ethyl acetate (3×80 mL), the organic phases were emerged, dried over anhydrous magnesium sulfate, filtered and then concentrated under reduced pressure. The residue was purified through silica column (ethyl acetate/petroleum ether=1:5, as an eluent) to get 23.91 g 2-(1-(2,4-dichlorophenyl)-1H-pyrazol-4-yl)acetonitrile as white solid with yield of 94.9%.

6) The Preparation of Intermediate 2-(1-(2,4-dichlorophenyl)-1H-pyrazol-4-yl)ethanamine

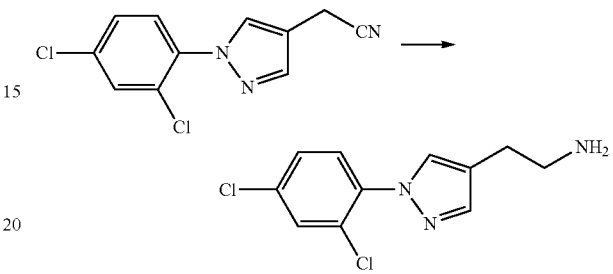

To a solution of 2-(1-(2,4-dichlorophenyl)-1H-pyrazol-4-yl)acetonitrile 2.52 g (0.01 mol), Raney nickel (1.0 g) and 100 mL of 10% ammonia in methanol were filled with hydrogen at 40 Pa, then the reaction mixture was continued stirring at room temperature for 3 h and monitored by TLC until the reaction was over, Raney nickel was filtered, the filtrate was concentrated under reduced pressure to obtain 2.52 g target intermediate as pale red brown sticky oil with yield of 98.6%.

Example 4

The Preparation of the Compound 23

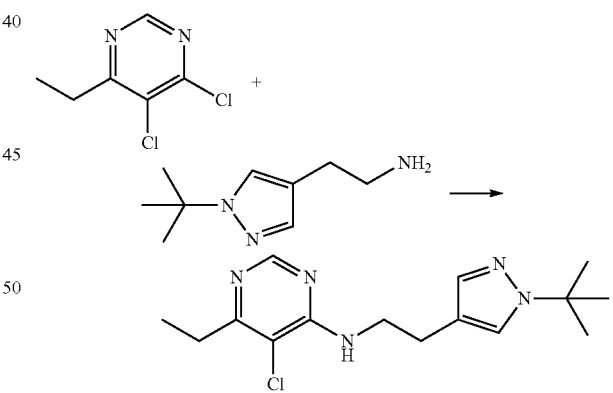

To a solution of 1.77 g (0.01 mol) 4,5-dichloro-2,6-dimethylpyrimidine (the preparation refers to Example 1, the difference is replacing ethyl 2-chloro-3-oxobutanoate to ethyl 2-chloro-3-oxopentanoate) and 1.67 g (0.01 mol) 2-(1-tert-butyl-1H-pyrazol-4-yl)ethanamine in 50 mL toluene was added 2.23 g (0.011 mol)triethylamine at room temperature. The reaction mixture was continued stirring and heating to reflux for 4-10 hours, and monitored by TLC (Thin-Layer Chromatography) until the reaction was over, the excessive solvent was evaporated under reduced pressure. then the mixture was poured into (3×50 mL) ethyl acetate to separate the organic layer, the organic phase was washed with 50 mL of brine, dried and evaporated under reduced pressure, the residual was purified via silica column (ethyl acetate/petroleum ether=1:2, as an eluent) to obtain 2.34 g compound 23 as slight yellow solid with yield of 76.2%, the m.p. is 77.5° C.

$^1$H-NMR (300 MHz, internal standard: TMS, solvent: CDCl$_3$) δ(ppm): 1.26 (3H, t), 1.58 (9H, s), 2.81 (2H, t), 3.65-3.73 (2H, q), 5.56 (1H, s), 7.38 (1H, s), 7.42 (1H, s), 8.43 (1H, s).

Example 5

The Preparation of the Compound 537

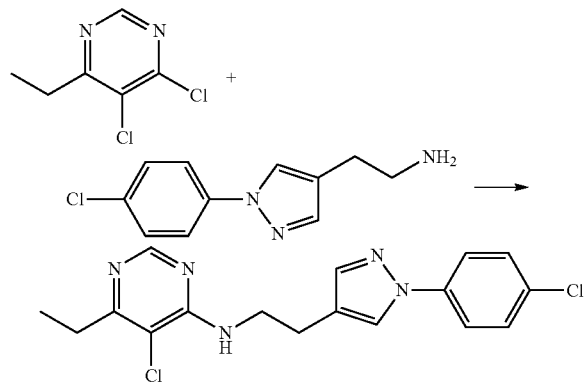

To a solution of 1.77 g (0.01 mol) 4,5-dichloro-6-ethyl-pyrimidine and 2.22 g (0.01 mol) 2-(1-(4-chlorophenyl)-1H-pyrazol-4-yl)ethanamine in 50 mL toluene was added 2.23 g (0.011 mol)triethylamine at room temperature. The reaction mixture was continued stirring and heating to reflux for 4-10 hours, and monitored by TLC (Thin-Layer Chromatography) until the reaction was over, the excessive solvent was evaporated under reduced pressure. then the mixture was poured into (3×50 mL) ethyl acetate to separate the organic layer, the organic phase was washed with 50 mL of brine, dried and evaporated under reduced pressure, the residual was purified via silica column (ethyl acetate/petroleum ether=1:2, as an eluent) to obtain 2.92 g compound 537 as white solid with yield of 80.6%, the m.p. is 160.5° C.

$^1$H-NMR (300 MHz, internal standard: TMS, solvent: CDCl$_3$) δ(ppm): 1.27 (3H, t), 2.72-2.84 (2H, q), 2.88 (2H, t), 3.71-3.80 (2H, q), 5.52 (1H, s), 7.41 (2H, dd), 7.56-7.64 (3H, m), 7.76 (1H, s), 8.45 (1H, s).

Example 6

The Preparation of the Compound 1373

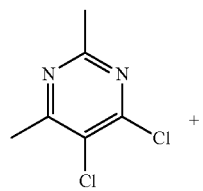

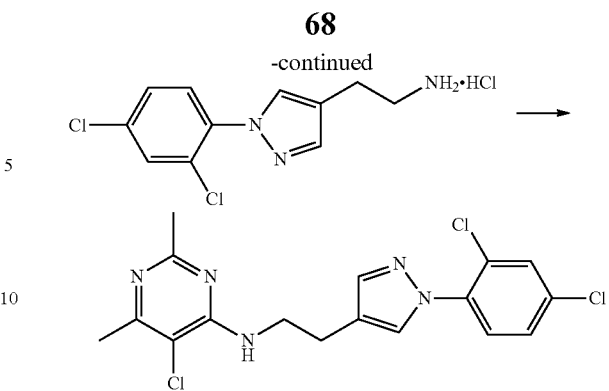

To a solution of 1.77 g (0.01 mol) 4,5-dichloro-2,6-dimethylpyrimidine (the preparation refers to Example 1, the difference is replacing formamidine acetate to ethanimidamide hydrochloride) and 2.22 g (0.01 mol) 2-(1-(2,4-dichlorophenyl)-1H-pyrazol-4-yl)ethanamine hydrochloride in 50 mL toluene was added 4.45 g (0.022 mol)triethylamine at room temperature. The reaction mixture was continued stirring and heating to reflux for 4-10 hours, and monitored by TLC (Thin-Layer Chromatography) until the reaction was over, the excessive solvent was evaporated under reduced pressure, then the mixture was poured into (3×50 mL) ethyl acetate to separate the organic layer, the organic phase was washed with 50 mL of brine, dried and evaporated under reduced pressure, the residual was purified via silica column (ethyl acetate/petroleum ether=1:2, as an eluent) to obtain 3.11 g compound 1373 as red brown oil with yield of 78.5%.

$^1$H-NMR (300 MHz, internal standard: TMS, solvent: CDCl$_3$) δ(ppm): 2.41 (3H, s), 2.49 (3H, s), 2.87 (2H, t), 3.72-3.85 (2H, q), 5.41 (1H, s), 7.32-7.38 (1H, q), 7.46-7.58 (2H, q), 7.63 (1H, s) 7.72 (1H, s).

Example 7

The Preparation of the Compound 5657

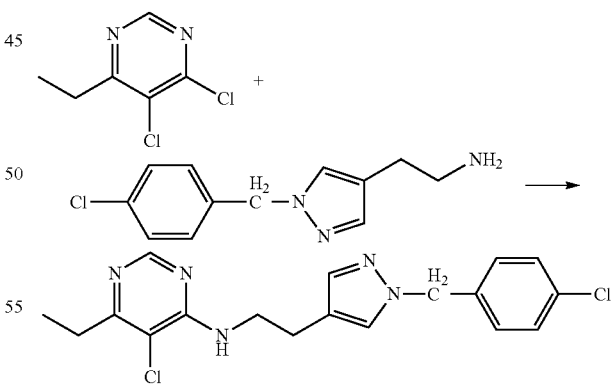

To a solution of 1.77 g (0.01 mol) 4,5-dichloro-6-ethyl-pyrimidine and 1.67 g (0.01 mol) 2-(1-(4-chlorobenzyl)-1H-pyrazol-4-yl)ethanamine in 50 mL toluene was added 2.23 g (0.011 mol)triethylamine at room temperature. The reaction mixture was continued stirring and heating to reflux for 4-10 hours, and monitored by TLC (Thin-Layer Chromatography) until the reaction was over, the excessive solvent was evaporated under reduced pressure. then the mixture was poured into (3×50 mL) ethyl acetate to separate the organic layer, the organic phase was washed with 50 mL of brine, dried and evaporated under reduced pressure, the residual was purified via silica column (ethyl acetate/petroleum ether=1:2, as an eluent) to obtain 2.77 g compound 5657 as white solid with yield of 73.8%, the m.p. is 109.9° C.

$^1$H-NMR (300 MHz, internal standard: TMS, solvent: CDCl$_3$) δ(ppm): 1.26 (3H, t), 2.70-2.87 (4H, m), 3.64-3.70 (2H, q), 5.24 (2H, s), 5.43 (1H, s), 7.13 (2H, d), 7.24 (1H, s), 7.31 (2H, d), 7.44 (1H, s), 8.42 (1H, s).

Other compounds of the present invention were prepared according to the above examples.

Physical properties and $^1$HNMR spectrum ($^1$HNMR, 300 MHz, internal standard: TMS, ppm) of some compounds of this invention are as follows:

Compound 8: m.p. 102.4° C. δ(CDCl$_3$): 1.57 (9H, s), 2.46 (3H, s), 2.79 (2H, t), 3.62-3.74 (2H, q), 5.55 (1H, s), 7.38 (1H, s), 7.42 (1H, s), 8.39 (1H, s).

Compound 38: m.p. 112.4° C. δ(CDCl$_3$): 1.58 (9H, s), 2.82 (2H, t), 3.68-3.79 (2H, q), 5.76 (1H, s), 6.72 (1H, s), 7.38 (1H, s), 7.42 (1H, s), 8.56 (1H, s).

Compound 241: m.p. 101-103° C. δ(CDCl$_3$): 2.46 (3H, s), 2.88 (2H, t), 3.75 (2H, dd), 5.53 (1H, s), 7.18-7.32 (1H, m), 7.45 (2H, t), 7.33-7.51 (3H, m), 7.79 (1H, s), 8.40 (1H, s).

Compound 244: m.p. 125.9° C. δ(CDCl$_3$): 2.47 (3H, s), 2.88 (2H, t), 3.71-3.82 (2H, q), 5.56 (1H, s), 7.13 (2H, d), 7.56-7.63 (3H, m), 7.73 (1H, s), 8.40 (1H, s).

Compound 246: m.p. 123.0° C. δ(CDCl$_3$): 2.53 (3H, s), 2.88 (2H, t), 3.71-3.80 (2H, q), 5.50 (1H, s), 6.93-7.02 (2H, m), 7.61 (1H, s), 7.77-7.88 (2H, m), 8.39 (1H, s).

Compound 257: δ(CDCl$_3$): 2.51 (3H, s), 2.84 (2H, t), 3.79-3.84 (2H, q), 5.51 (1H, s), 7.25 (1H, s), 7.42 (2H, t), 7.75 (2H, t), 7.80 (1H, s), 8.45 (1H, s).

Compound 258: m.p. 118.5° C. δ(CDCl$_3$): 2.51 (3H, s), 2.84 (2H, t), 3.74-3.82 (2H, q), 5.51 (1H, s), 7.35-7.45 (3H, m), 7.68 (1H, s), 7.80 (1H, s), 7.85 (1H, s), 8.45 (1H, s).

Compound 261: m.p. 87.2° C. δ(CDCl$_3$): 2.46 (3H, s), 2.89 (2H, t), 3.70-3.88 (2H, q), 5.53 (1H, s), 7.26-7.45 (2H, m), 7.47-7.62 (2H, m), 7.63 (1H, s), 7.73 (1H, s), 8.41 (1H, s).

Compound 263: δ(CDCl$_3$): 2.51 (3H, s), 2.84 (2H, t), 3.70-3.77 (2H, q), 5.51 (1H, s), 7.15 (21-1, d), 7.60 (1H, s), 7.68 (11-1, d), 7.82 (1H, s), 8.42 (1H, s).

Compound 264: m.p. 157.7° C. δ(CDCl$_3$): 2.51 (3H, s), 2.84 (2H, t), 3.79-3.85 (2H, q), 5.51 (1H, s), 7.45 (2H, d), 7.54 (1H, s), 7.77 (1H, s), 7.85 (1H, s), 8.45 (1H, s).

Compound 265: m.p. 128.8° C. δ(CDCl$_3$): 2.51 (3H, s), 2.84 (2H, t), 3.80-3.85 (2H, q), 5.51 (1H, s), 7.20 (2H, t), 7.58-7.64 (2H, q), 7.75 (1H, s), 8.41 (1H, s).

Compound 297: m.p. 123.0° C. δ(CDCl$_3$): 2.38 (3H, s), 2.46 (3H, s), 2.87 (2H, t), 3.70-3.80 (21H, q), 5.55 (1H, s), 7.22 (2H, d), 7.53 (2H, d), 7.58 (1H, s), 7.75 (1H, s), 8.40 (1H, s).

Compound 309: m.p. 125.4° C. δ(CDCl$_3$): 2.47 (3H, s), 2.90 (2H, t), 3.70-3.82 (2H, q), 5.52 (1H, s), 7.65 (1H, s), 7.71 (2H, d), 7.79 (2H, d), 7.85 (1H, s), 8.41 (1H, s).

Compound 310: δ(CDCl$_3$): 2.51 (3H, s), 2.84 (2H, t), 3.79-3.84 (2H, q), 3.90 (3H, s), 5.60 (1H, s), 7.05 (2H, t), 7.24 (1H, t), 7.60 (1H, s), 7.72 (1H, d), 7.90 (1H, s), 8.45 (1H, s).

Compound 312: m.p. 95-96° C. δ(CDCl$_3$): 2.46 (3H, s), 2.87 (2H, t), 3.69-3.82 (2H, m), 3.84 (3H, s), 5.53 (1H, s), 6.90-7.01 (2H, q), 7.50-7.60 (4-1, m), 7.69 (1H, s), 8.40 (1H, s).

Compound 318: m.p. 111.6° C. δ(CDCl$_3$): 2.47 (3H, s), 2.89 (2H, t), 3.74-3.85 (2H, q), 5.57 (1-1, s), 7.30 (2H, d), 7.62 (1H, s), 7.69 (2H, d), 7.77 (1H, s), 8.41 (1H, s).

Compound 398: m.p. 95.4° C. δ(CDCl$_3$): 2.41 (3H, s), 2.86 (2H, t), 3.81-3.89 (2H, q), 5.45 (1H, s), 7.21 (2H, m), 7.61 (1H, t), 7.79-7.87 (2H, m), 8.41 (1H, s).

Compound 406: δ(CDCl$_3$): 2.46 (3H, s), 2.93 (2H, t), 3.73-3.92 (2H, q), 5.50 (1H, s), 7.42 (1H, s), 7.65-7.79 (3H, m), 8.39 (1H, s).

Compound 519: m.p. 105.3° C. δ(CDCl$_3$): 1.27 (3H, t), 2.77-2.84 (2H, q), 2.89 (2H, t), 3.70-3.85 (2H, q), 5.54 (1H, s), 7.30 (1H, d), 7.45 (2H, t), 7.60-7.75 (3H, m), 7.81 (1H, s), 8.46 (1H, s).

Compound 522: m.p. 119.2° C. δ(CDCl$_3$): 1.27 (3H, t), 2.73-2.85 (2H, q), 2.88 (2H, t), 3.70-3.82 (2H, q), 5.52 (1H, s), 7.13 (2H, d), 7.55-7.68 (3H, m), 7.73 (1H, s), 8.45 (1H, s).

Compound 524: m.p. 109.5° C. δ(CDCl$_3$): 1.26 (3H, t), 2.74-2.84 (2H, q), 2.89 (2H, t), 3.71-3.80 (2H, q), 5.51 (1H, s), 6.93-7.02 (2H, m), 7.62 (1H, s), 7.76-7.89 (2H, m), 8.44 (1H, s).

Compound 535: m.p. 105.5° C. δ(CDCl$_3$): 1.25 (3H, t), 2.82-2.88 (2H, q), 2.95 (2H, t), 3.82-3.87 (2H, q), 5.51 (1H, s), 7.25 (1H, s), 7.42 (2H, t), 7.75 (2H, t), 7.80 (1H, s), 8.45 (1H, s).

Compound 536: δ(CDCl$_3$): 1.25 (3H, t), 2.81-2.89 (2H, q), 2.95 (2H, t), 3.80-3.85 (2H, q), 5.51 (1H, s), 7.45 (2H, d), 7.54 (1H, s), 7.77 (1H, s), 7.85 (1H, s), 8.45 (1H, s).

Compound 539: m.p. 105.6° C. δ(CDCl$_3$): 1.26 (3H, t), 2.73-2.81 (2H, q), 2.89 (2H, t), 3.75 (2H, t), 5.55 (1H, s), 7.34 (1H, d), 7.45-7.68 (2H, m), 7.63 (1H, s), 7.73 (1H, s), 8.44 (1H, s).

Compound 541: δ(CDCl$_3$): 1.25 (3H, t), 2.82-2.87 (2H, q), 2.95 (2H, t), 3.79-3.85 (2H, q), 5.57 (1H, s), 7.15 (2H, d), 7.60 (1H, s), 7.68 (1H, d), 7.82 (1H, s), 8.42 (1H, s).

Compound 542: m.p. 124.8° C. δ(CDCl$_3$): 1.25 (3H, t), 2.83-2.87 (2H, q), 2.95 (2H, t), 3.80-3.84 (2H, q), 5.51 (1H, s), 7.45 (2H, d), 7.54 (1H, s), 7.77 (1H, s), 7.85 (1H, s), 8.45 (1H, s).

Compound 543: m.p. 111.7° C. δ(CDCl$_3$): 1.25 (3H, t), 2.83-2.87 (2H, q), 2.95 (2H, t), 3.79-3.85 (2H, q), 5.51 (1H, s), 7.45 (2H, d), 7.54 (1H, s), 7.77 (1H, s), 7.85 (1H, s), 8.45 (1H, s).

Compound 575: m.p. 122.8° C. δ(CDCl$_3$): 1.28 (3H, t), 2.38 (3H, s), 2.73-2.84 (2H, q), 2.88 (2H, t), 3.71-3.80 (2H, q), 5.57 (1H, s), 7.24 (2H, d), 7.53 (2H, d), 7.59 (1H, s), 7.75 (1H, s), 8.45 (1H, s).

Compound 587: m.p. 128.2° C. δ(CDCl$_3$): 1.27 (3H, t), 2.72-2.85 (2H, q), 2.90 (2H, t), 3.71-3.85 (2H, q), 5.55 (1H, s), 7.65 (1H, s), 7.71 (2H, d), 7.79 (2H, d), 7.86 (1H, s), 8.46 (1H, s).

Compound 588: m.p. 86.5° C. δ(CDCl$_3$): 1.25 (3H, t), 2.83-2.87 (2H, q), 2.95 (2H, t), 3.80-3.85 (2H, q), 3.90 (3H, s), 5.60 (1H, s), 7.05 (2H, t), 7.24 (1H, t), 7.60 (1H, s), 7.72 (1H, d), 7.90 (1H, s), 8.45 (1H, s).

Compound 590: m.p. 97.3° C. δ(CDCl$_3$): 1.26 (3H, t), 2.70-2.95 (4H, m), 3.64-3.80 (2H, q), 3.83 (3H, s), 5.57 (1H, s), 6.90-7.01 (2H, q), 7.50-7.61 (4H, m), 7.70 (1H, s), 8.45 (1H, s).

Compound 596: m.p. 107.0° C. δ(CDCl$_3$): 1.27 (3H, t), 2.73-2.85 (2H, q), 2.89 (2H, t), 3.71-3.82 (2H, q), 5.52 (1H, s), 7.30 (2H, d), 7.62 (1H, s), 7.68 (2H, d), 7.78 (1H, s), 8.45 (1H, s).

Compound 676: m.p. 110.5° C. δ(CDCl$_3$): 1.25 (3H, t), 2.83-2.88 (2H, q), 2.95 (2H, t), 3.72-3.79 (2H, q), 5.57 (1H, s), 7.21 (2H, m), 7.61 (1H, t), 7.84 (2H, m), 8.41 (1H, s).

Compound 797: m.p. 108-110° C. δ(CDCl$_3$): 2.92 (2H, t), 3.81 (2H, dd), 5.80 (1H, s), 6.72 (1H, t), 7.21-7.35 (1H, m), 7.44 (2H, t), 7.58-7.71 (3H, m), 7.80 (1H, s), 8.58 (1H, s).

Compound 800: m.p. 143.5° C. δ(CDCl$_3$): 2.91 (2H, t), 3.75-3.88 (2H, q), 5.78 (1H, s), 6.72 (1H, t), 7.14 (2H, t), 7.53-7.67 (3H, m), 7.73 (1H, s), 8.58 (1H, s).

Compound 802: m.p. 133.0° C. δ(CDCl$_3$): 2.91 (2H, t), 3.77-3.86 (2H, q), 5.79 (1H, s), 6.72 (11-1, t), 6.94-7.04 (2H, m), 7.62 (1H, s), 7.78-7.85 (2H, m), 8.57 (1H, s).

Compound 813: m.p. 109.5° C. δ(CDCl$_3$): 2.74 (2H, t), 3.80-3.86 (2H, q), 5.81 (1H, s), 6.81 (1H, s), 7.25 (11H, s), 7.42 (2H, t), 7.75 (2H, t), 7.80 (1H, s), 8.45 (1-1, s).

Compound 814: m.p. 97.4° C. δ(CDCl$_3$): 2.74 (2H, t), 3.80-3.84 (2H, q), 5.81 (1H, s), 6.81 (1H, s), 7.45 (2H, d), 7.54 (1H, s), 7.77 (1H, s), 7.85 (1H, s), 8.45 (1H, s).

Compound 815: m.p. 151.8° C. δ(CDCl$_3$): 2.90 (2H, t), 3.75-3.97 (2H, q), 5.80 (1H, s), 6.72 (1H, t), 7.30-7.46 (2H, q), 7.48-7.65 (3H, m), 7.70 (1H, s), 8.58 (11-1H, s).

Compound 817: m.p. 120.0° C. δ(CDCl$_3$): 2.81-3.02 (2H, q), 3.75-3.93 (2H, q), 5.82 (1H, s), 6.72 (1H, t), 7.32-7.48 (2H, m), 7.52 (1H, t), 7.60 (1H, d), 7.64 (1H, s), 8.57 (1H, s).

Compound 819: m.p. 108.8° C. δ(CDCl$_3$): 2.76 (2H, t), 3.81-3.87 (2H, q), 5.81 (1H, s), 6.85 (1H, s), 7.15 (2H, d), 7.60 (1H, s), 7.68 (1H, d), 7.82 (1H, s), 8.42 (1H, s).

Compound 820: m.p. 164.7° C. δ(CDCl$_3$): 2.74 (2H, t), 3.80-3.84 (2H, q), 5.81 (1H, s), 6.81 (1H, s), 7.45 (2H, s), 7.64 (1H, s), 7.77 (2H, d), 8.55 (1H, s).

Compound 821: δ(CDCl$_3$): 2.74 (2H, t), 3.78-3.85 (2H, q), 5.81 (1H, s), 6.81 (1H, s), 7.45 (2H, d), 7.54 (1H, s), 7.77 (1H, s), 7.85 (1H, s), 8.45 (1H, s).

Compound 853: m.p. 131.5° C. δ(CDCl$_3$): 2.38 (3H, s), 2.90 (2H, t), 3.73-3.87 (2H, q), 5.80 (1H, s), 6.72 (1H, t), 7.24 (2H, d), 7.53 (2H, d), 7.59 (1H, s), 7.75 (1H, s), 8.57 (1H, s).

Compound 865: m.p. 132.4° C. δ(CDCl$_3$): 2.93 (2H, t), 3.75-3.90 (2H, q), 5.80 (1H, s), 6.72 (1H, t), 7.60-7.81 (5H, m), 7.86 (1H, s), 8.59 (1H, s).

Compound 866: m.p. 104.5° C. δ(CDCl$_3$): 2.84 (2H, t), 3.80-3.85 (2H, q), 3.90 (3H, s), 5.81 (1H, s), 6.81 (1H, s), 7.05 (2H, t), 7.24 (1H, t), 7.60 (1H, s), 7.72 (1H, d), 7.90 (1H, s), 8.55 (1H, s).

Compound 868: m.p. 132.5° C. δ(CDCl$_3$): 2.89 (2H, t), 3.80-4.15 (5H, m), 5.81 (1H, s), 6.72 (1H, t), 6.97 (2H, d), 7.48-7.65 (3H, m), 7.70 (1H, s), 8.58 (1H, s).

Compound 874: m.p. 138.0° C. δ(CDCl$_3$): 2.91 (2H, t), 3.75-3.88 (2H, q), 5.78 (1H, s), 6.72 (1H, t), 7.31 (2H, d), 7.63 (1H, s), 7.65-7.72 (2H, m), 7.78 (1H, s), 8.58 (1H, s).

Compound 954:6 (CDCl$_3$): 2.86 (2H, t), 3.82-3.89 (2H, q), 5.81 (1H, s), 6.75 (1H, s), 7.21 (2H, m), 7.61 (1H, t), 7.84 (2H, m), 8.41 (1H, s).

Compound 1095: m.p. 103.9° C. δ(CDCl$_3$): 2.92 (2H, t), 3.70-3.95 (2H, q), 5.94 (1H, s), 7.33-7.40 (1H, q), 7.42-7.74 (3H, m), 7.71 (1H, s), 8.57 (1H, s).

Compound 1143: m.p. 118.7° C. δ(CDCl$_3$): 2.93 (2H, t), 3.70-3.98 (2H, q), 5.96 (1H, s), 7.55-7.81 (5H, m), 7.86 (1H, s), 8.59 (1H, s).

Compound 1146: m.p. 111.4° C. δ(CDCl$_3$): 2.91 (2H, t), 3.71-3.83 (2H, q), 3.85 (3H, s), 5.95 (1H, s), 6.97 (2H, d), 7.50-7.61 (3H, m), 7.70 (1H, s), 8.58 (1H, s).

Compound 1424: m.p. 96.9° C. δ(CDCl$_3$): 2.42 (3H, s), 2.49 (3H, s), 2.86 (2H, t), 3.70-3.79 (2H, q), 3.84 (3H, s), 5.45 (1H, s), 6.90-7.05 (2H, q), 7.51-7.64 (3H, q), 7.69 (1H, s).

Compound 4694: m.p. 135.6° C. δ(CDCl$_3$): 2.46 (3H, s), 2.88 (2H, t), 3.72-3.85 (2H, q), 5.51 (1H, s), 7.61 (1H, s), 7.73-7.79 (1H, m), 7.86-7.93 (1H, q), 8.34 (1H, d), 8.40 (1H, s), 8.42 (1H, s).

Compound 4733: m.p. 94.9° C. δ(CDCl$_3$): 1.26 (3H, t), 2.73-2.85 (2H, q), 2.90 (2H, t), 3.70-3.85 (2H, q), 5.53 (1H, s), 7.19 (1H, t), 7.63 (1H, s), 7.75-7.86 (1H, q), 7.95 (1H, d), 8.40 (1H, d), 8.45 (1H, s).

Compound 4736: m.p. 154.9° C. δ(CDCl$_3$): 1.26 (3H, t), 2.74-2.84 (2H, q), 2.89 (2H, t), 3.72-3.81 (2H, q), 5.51 (1H, s), 7.62 (1H, s), 7.73-7.79 (1H, m), 7.91 (1H, d), 8.34 (1H, t), 8.38 (1H, s), 8.45 (1H, s).

Compound 4778: m.p. 155.4° C. 8 (CDCl$_3$): 2.91 (2H, t), 3.77-3.87 (2H, q), 5.78 (1H, s), 6.72 (1H, t), 7.62 (1H, s), 7.74-7.80 (1H, q), 7.91 (1H, d), 8.34 (1H, d), 8.39 (11H, s), 8.45 (11H, s).

Compound 5379: m.p. 82.4° C. δ(CDCl$_3$): 2.46 (3H, t), 2.79 (2H, t), 3.62-3.72 (2H, q), 5.24 (2H, s), 5.42 (1H, s), 7.13 (2H, d), 7.24 (11H, s), 7.31 (2H, d), 7.43 (1H, s), 8.37 (1H, s).

Compound 5935: m.p. 122.2° C. δ(CDCl$_3$): 2.81 (2H, t), 3.67-3.78 (2H, q), 5.25 (2H, s), 5.69 (1H, s), 6.71 (1H, t), 7.14 (2H, d), 7.24 (1H, s), 7.32 (2H, d), 7.44 (1H, s), 8.55 (1H, s).

Compound 10932: δ(DMSO): 1.29 (3H, t), 2.80-3.08 (4H, m), 3.72-3.91 (2H, q), 7.47 (21H, d), 7.62 (11H, d), 7.81 (2H, d), 8.42 (1H, d), 8.76 (1H, d), 9.39 (1H, s).

Test of Biological Activity

The compounds of the present invention showed good activity against many pathogens, insects and pest mites in agricultural field.

Example 8

Fungicidal Testing

The compound samples of the present invention were tested in fungicidal activity in vitro or protectant activity in vivo. The results of the fungicidal testing are as follows.

(1) Determination of Fungicidal Activity In Vitro

The method is as follows: High Through Put is used in the test. The compound is dissolved in a proper solvent to become a testing solution whose concentration is designed. The solvent is selected from acetone, methanol, DMF and so on according to their dissolving capability to the sample. In a no animalcule condition, the testing solution and pathogens suspension are added into the cells of 96 cells culture board, which then should be placed in the constant temperature box. 24 hours later, pathogen germination or growth can be investigated by eyeballing, and the activity in vitro of the compound is evaluated based on germination or growth of control treatment.

The activities in vitro (inhibition rate) of some compounds are as follows:

The inhibition rate against rice blast:

At the dosage of 25 ppm, the compounds 241, 261, 309, 318, 519, 522, 539, 590, 797, 815, 817, 868, 1095, 1143, 1146, 1373, 1424, 5657, 10932 and so on showed more than 80% control against rice blast. Among them, the inhibition rate of compounds 241, 318, 797 and 5657 was 100%.

At the dosage of 8.3 ppm, the compounds 241, 797 and so on showed more than 80% control against rice blast. Among them, the inhibition rate of compound 241 was 100%.

At the dosage of 2.8 ppm, the compounds 241, 797 and so on showed more than 80% control against rice blast. Among them, the inhibition rate of compound 241 was 100%.

At the dosage of 0.9 ppm, the compound 241 showed 100% control against rice blast.

At the dosage of 0.3 ppm, the compound 241 showed 80% control against rice blast.

At the dosage of 0.1 ppm, the compound 241 showed 80% control against rice blast.

The inhibition rate against cucumber gray mold:

At the dosage of 25 ppm, the compounds 241, 537, 539, 797, 800, 853, 5657 and so on showed more than 80% control against cucumber gray mold. Among them, the inhibition rate of compound 5657 was 100%.

(2) The Determination of Protectant Activity In Vivo

The method is as follows: The whole plant is used in this test. The compound is dissolved in a proper solvent to get mother solution. The proper solvent is selected from acetone, methanol, DMF and so on according to their dissolving capability to the sample. The volume rate of solvent and testing solution (v/v) is equal to or less than 5%. The mother solution is diluted with water containing 0.1% tween-80 to get the testing solution whose concentration is designed. The testing solution is sprayed to the host plant by a special plant sprayer. The plant is inoculated with fungus after 24 hours. According to the infecting characteristic of fungus, the plant is stored in a humidity chamber and then transferred into greenhouse after infection is finished. And the other plants are placed in greenhouse directly. The activity of compound is obtained by eyeballing after 7 days in common.

The protectant activities in vivo of some compounds are as follows:

The protectant activity against cucumber downy mildew in vivo:

At the dosage of 400 ppm, the compounds 8, 38, 241, 261, 312, 318, 406, 519, 537, 539, 575, 587, 590, 596, 800, 853, 865, 868, 874, 1143, 1146, 1373, 1424, 4733, 5657, 5935, 10932 and so on showed more than 80% control against cucumber downy mildew. Among them, the protectant activity of compounds 38, 241, 261, 312, 318, 406, 519, 537, 539, 587, 590, 596, 800, 853, 865, 868, 874, 1373, 1424, 5657, 5935 and 10932 was 100%.

At the dosage of 100 ppm, the compounds 38, 241, 261, 312, 318, 406, 519, 537, 539, 587, 590, 596, 800, 853, 868, 874, 1373, 1424, 4733, 5657, 5935, 10932 and so on showed more than 80% control against cucumber downy mildew. Among them, the protectant activity of compounds 241, 261, 312, 318, 406, 519, 537, 539, 590, 596, 800, 853, 868, 874, 1373, 1424, 4733, 5657 and 5935 was 100%.

At the dosage of 50 ppm, the compounds 241, 261, 312, 318, 406, 519, 537, 539, 587, 590, 596, 800, 853, 868, 1373, 1424, 5657, 5935 and so on showed more than 80% control against cucumber downy mildew. Among them, the protectant activity of compounds 241, 261, 312, 406, 537, 539, 590, 800, 853, 868, 1424 and 5935 was 100%.

At the dosage of 25 ppm, the compounds 241, 261, 312, 318, 537, 539, 590, 800, 853, 868, 1373, 1424, 5935 and so on showed more than 80% control against cucumber downy mildew. Among them, the protectant activity of compounds 241, 261, 312, 537, 539, 590 and 868 was 100%.

At the dosage of 12.5 ppm, the compounds 261, 537, 868, 1373 and so on showed more than 80% control against cucumber downy mildew. Among them, the protectant activity of compounds 261, 537 and 1373 was 100%.

At the dosage of 6.25 ppm, the compound 537 showed 98% control against cucumber downy mildew. The compound 1373 showed 95% control against cucumber downy mildew.

At the dosage of 3.125 ppm, the compound 1373 showed 85% control against cucumber downy mildew.

The protectant activity against wheat powdery mildew in vivo:

At the dosage of 400 ppm, the compounds 8, 23, 38, 244, 261, 297, 309, 312, 318, 406, 522, 537, 539, 587, 596, 797, 800, 815, 817, 853, 865, 868, 874, 1095, 1143, 1373, 1424, 4733, 5935 and so on showed more than 80% control against wheat powdery mildew. Among them, the protectant activity of compounds 8, 23, 38, 244, 261, 297, 309, 312, 318, 406, 522, 537, 539, 587, 596, 797, 800, 815, 817, 865, 868, 874, 1095, 1373, 1424, 4733 and 5935 was 100%.

At the dosage of 100 ppm, the compounds 8, 23, 38, 244, 261, 297, 309, 312, 318, 406, 596, 797, 800, 815, 817, 865, 868, 874 and so on showed more than 80% control against wheat powdery mildew. Among them, the protectant activity of compounds 8, 38, 244, 312, 318, 406, 596, 797, 800, 815, 817, 868 and 874 was 100%.

At the dosage of 25 ppm, the compounds 38, 244, 309, 312, 318, 406, 596, 797, 800, 815, 817, 865, 868, 874 and so on showed more than 80% control against wheat powdery mildew. Among them, the protectant activity of compounds 38, 312, 318, 596, 797, 800, 815, 817, 868 and 874 was 100%.

At the dosage of 6.25 ppm, the compounds 309, 312, 318, 406, 596, 800, 815, 817, 868, 874 and so on showed more than 80% control against wheat powdery mildew. Among them, the protectant activity of compounds 817, 868 and 874 was 100%.

At the dosage of 1.6 ppm, the compound 868 showed 80% control against wheat powdery mildew.

The protectant activity against corn rust in vivo:

At the dosage of 400 ppm, the compounds 8, 23, 38, 241, 261, 297, 312, 318, 406, 522, 537, 539, 575, 590, 596, 797, 800, 815, 817, 853, 865, 868, 874, 1095, 1143, 1373, 1424, 4733, 5935, 10932 and so on showed more than 80% control against corn rust. Among them, the protectant activity of compounds 23, 38, 241, 261, 297, 312, 318, 406, 522, 537, 590, 596, 797, 800, 815, 817, 865, 868, 874, 1095, 1143, 1373, 1424, 4733, 5935 and 10932 was 100%.

At the dosage of 100 ppm, the compounds 241, 261, 297, 312, 318, 406, 522, 575, 590, 596, 797, 800, 815, 817, 868, 874, 1095, 1373, 1424, 4733 and so on showed more than 80% control against corn rust. Among them, the protectant activity of compounds 261, 297, 312, 318, 522, 590, 596, 797, 800, 815, 817, 868 and 874 was 100%.

At the dosage of 25 ppm, the compounds 297, 522, 590, 797, 800, 815, 817, 868, 874 and so on showed more than 80% control against corn rust. Among them, the protectant activity of compounds 797, 817, 868 and 874 was 100%.

At the dosage of 6.25 ppm, the compounds 815, 817, 868, 874 and so on showed more than 80% control against corn rust. Among them, the protectant activity of compound 874 was 100%.

At the dosage of 1.6 ppm, the compound 817 showed 70% control against corn rust.

The protectant activity against cucumber anthracnose in vivo:

At the dosage of 400 ppm, the compounds 8, 38, 318, 406, 596, 874, 4733, 5379, 5657, 5935 and so on showed more than 80% control against cucumber anthracnose. Among them, the protectant activity of compounds 8, 38, 318, 406, 596, 874 and 5657 was 100%.

At the dosage of 100 ppm, the compounds 8, 38, 318, 596, 874 and so on showed more than 80% control against cucumber anthracnose. Among them, the protectant activity of compounds 318, 596 and 874 was 100%.

At the dosage of 25 ppm, the compounds 8, 38, 318, 596, 874 and so on showed more than 80% control against cucumber anthracnose. Among them, the protectant activity of compounds 318 and 874 was 100%.

At the dosage of 6.25 ppm, the compounds 38, 318, 874 and so on showed more than 80% control against cucumber anthracnose. Among them, the protectant activity of compound 318 was 100%.

At the dosage of 3.13 ppm, the compound 318 showed 100% control against cucumber anthracnose.

At the dosage of 1.56 ppm, the compound 318 showed 98% control against cucumber anthracnose.

At the dosage of 0.78 ppm, the compound 318 showed 98% control against cucumber anthracnose.

(3) The Contrastive Test Results of Some Compounds and Contrasts

Contrastive tests were carried out between some compounds and contrasts. The test results are listed in table 112-table 114 ("///" in the following tables means no test).

TABLE 112

The comparative test of protectant activity against cucumber downy mildew

| Compound No. | control effect against cucumber downy mildew(%) | | | | |
|---|---|---|---|---|---|
| | 400 mg/L | 100 mg/L | 50 mg/L | 25 mg/L | 12.5 mg/L |
| 241 | 100 | 100 | 100 | 100 | 65 |
| 261 | 100 | 100 | 100 | 100 | 100 |
| 312 | 100 | 100 | 100 | 100 | /// |
| 318 | 100 | 100 | 98 | 90 | /// |
| 537 | 100 | 100 | 100 | 100 | 100 |
| 539 | 100 | 100 | 100 | 100 | /// |
| 590 | 100 | 100 | 100 | 100 | /// |
| 800 | 100 | 100 | 100 | 98 | /// |
| 853 | 100 | 100 | 100 | 80 | /// |
| 868 | 100 | 100 | 100 | 100 | 85 |
| 1373 | 100 | 100 | 100 | 100 | 100 |
| 1424 | 100 | 100 | 100 | 98 | /// |
| 5935 | 100 | 100 | 100 | 95 | 50 |
| CK1 | 100 | 100 | 95 | 20 | /// |
| CK2 | 100 | 100 | 75 | 20 | /// |
| CK3 | 100 | 40 | 30 | 0 | /// |
| CK4 | 100 | 50 | 40 | 0 | /// |
| CK5 | 85 | /// | /// | /// | /// |

TABLE 113

The comparative test of protectant activity against wheat powdery

| Compound No. | control effect against wheat powdery mildew (%) | | | |
|---|---|---|---|---|
| | 400 mg/L | 100 mg/L | 25 mg/L | 6.25 mg/L |
| 8 | 100 | 100 | /// | /// |
| 23 | 100 | 98 | /// | /// |
| 38 | 100 | 100 | 100 | 40 |
| 244 | 100 | 100 | 80 | 50 |
| 261 | 100 | 80 | 60 | 50 |
| 309 | 100 | 90 | 85 | 80 |
| 312 | 100 | 100 | 100 | 95 |
| 318 | 100 | 100 | 100 | 90 |
| 406 | 100 | 100 | 98 | 90 |
| 596 | 100 | 100 | 100 | 95 |
| 797 | 100 | 100 | 100 | 60 |
| 800 | 100 | 100 | 100 | 95 |
| 815 | 100 | 100 | 100 | 80 |
| 817 | 100 | 100 | 100 | 100 |
| 865 | 100 | 85 | 80 | 40 |
| 868 | 100 | 100 | 100 | 100 |
| 874 | 100 | 100 | 100 | 100 |
| CK1 | 100 | 60 | 40 | 0 |
| CK2 | 100 | 50 | 20 | 0 |
| CK3 | 0 | /// | /// | /// |
| CK4 | 0 | /// | /// | /// |
| CK5 | 0 | /// | /// | /// |

TABLE 114

The comparative test of protectant activity against cucumber anthracnose

| Compound No. | control effect against cucumber anthracnose (%) | | | | | | |
|---|---|---|---|---|---|---|---|
| | 400 mg/L | 100 mg/L | 25 mg/L | 6.25 mg/L | 3.13 mg/L | 1.56 mg/L | 0.78 mg/L |
| 8 | 100 | 90 | 80 | 60 | /// | /// | /// |
| 38 | 100 | 95 | 90 | 85 | /// | /// | /// |
| 318 | 100 | 100 | 100 | 100 | 100 | 98 | 98 |
| 596 | 100 | 100 | 98 | 75 | /// | /// | /// |
| 874 | 100 | 100 | 100 | 98 | 60 | 20 | 0 |
| CK3 | 0 | /// | /// | /// | /// | /// | /// |
| CK4 | 0 | /// | /// | /// | /// | /// | /// |
| CK5 | 0 | /// | /// | /// | /// | /// | /// |

Example 9

Bioactivity Test Against Insects and Mites

Determination of insecticidal activity of compounds of the present invention against a few insects were carried out by the following procedures:

Compounds were dissolved in mixed solvent (acetone:methanol=1:1), and diluted to required concentration with water containing 0.1% of tween 80.

Diamond back moth, armyworm, peach aphid and carmine spider mite were used as targets and the method of spraying by airbrush was used for determination of insecticidal bioassays.

(1) Bioactivity Test Against Diamond Back Moth

The method of spraying by airbrush: The cabbage leaves were made into plates of 2 cm diameter by use of punch. A test solution (0.5 ml) was sprayed by airbrush at the pressure of 0.7 kg/cm$^2$ to both sides of every plate. 10 Second instar larvae were put into the petri-dishes after the leaf disc air-dried and 3 replicates were set for each treatment. Then the insects were maintained in observation room (25° C., 60~70% R.H.). Scores were conducted and mortalities were calculated after 72 h.

Part of Test Results Against Diamond Back Moth:

At the dosage of 600 ppm, the compounds 241, 797, 817, 865 and 10932 showed 100% control against diamond back moth.

At the dosage of 100 ppm, the compound 797 showed 85% control against diamond back moth.

(2) Bioactivity Test Against Armyworm

The method of spraying by airbrush: The corn leaves were made into plates of 2 cm diameter by use of punch. A test solution (0.5 ml) was sprayed by airbrush at the pressure of 0.7 kg/cm$^2$ to both sides of every plate. 10 Second instar larvae were put into the petri-dishes after the leaf disc air-dried and 3 replicates were set for each treatment. Then the insects were maintained in observation room (25° C., 60~70% R.H.). Scores were conducted and mortalities were calculated after 72 h.

Part of Test Results Against Armywormn:

At the dosage of 600 ppm, the compounds 797, 865, 10932 and so on showed more than 80% control against armyworm. Among them, the compounds 797 and 865 showed 100% control.

(3) Bioactivity Test Against Green Peach Aphid

Method: Filter papers were put in culture dishes (Diameter=6 cm), and water was dripped on filter papers for preserving moisture. Green peach aphids (*Myzus Persicae* Sulzer) were maintained on cabbage. Leaves (Diameter=3 cm) of approximately 15-30 aphids were put in the culture dishes. Bioactivity tests were used the method of Airbrush Foliar Spray, pressure=10 psi (0.7 kg/cm2), spray volume=0.5 mL. The studies were conducted at three constant temperatures 25±1 C in incubator cabinets with 60±5% RH. Survey the survival aphids after 48 h and calculate the death rates.

At the dosage of 600 ppm, the compounds 8, 23, 38, 241, 244, 309, 406, 522, 575, 587, 596, 797, 800, 815, 817, 853, 865, 1146, 1373, 1424, 4733, 5935, 10932 and so on showed more than 80% control against Green Peach Aphid. Among them, the compounds 23, 38, 406, 522, 587, 596, 797, 800, 815, 817, 853, 1146, 1373, 1424, 4733, 5935 and 10932 showed 100% control.

At the dosage of 100 ppm, the compounds 23, 38, 406, 522, 575, 587, 797, 800, 815, 817, 1373, 4733 and so on showed more than 80% control against Green Peach Aphid. Among them, the compounds 38, 800, 817, 1373 and 4733 showed 100% control.

At the dosage of 10 ppm, the compound 4733 showed more than 80% control against Green Peach Aphid.

(4) Bioactivity Test Against Carmine Spider Mite

The method: shoots with two true leaves in pot were taken, the healthy adults of carmine spider mite were inoculated to the leaves. The adults were counted and then sprayed with airbrush at the pressure of 0.7 kg/cm$^2$ and at dose of 0.5 ml. 3 replicates were set for each treatment. And then they were maintained in standard observation room. Scores were conducted and mortalities were calculated after 72 hrs.

Bioactivity Test Against Carmine Spider Mite

At the dosage of 600 ppm, the compounds 8, 23, 38, 241, 244, 297, 312, 318, 406, 522, 575, 596, 797, 815, 817, 1373, 1424, 4733, 10932 and so on showed more than 80% control against carmine spider mite. Among them, the compounds 8, 23, 38, 241, 318, 406, 522, 575, 596, 797, 817, 1373, 1424 and 4733 showed 100% control.

At the dosage of 100 ppm, the compounds 23, 318, 406, 522, 575, 596, 817, 4733 and so on showed more than 80% control against carmine spider mite. Among them, the compounds 406, 522, 596 and 817 showed 100% control.

At the dosage of 10 ppm, the compound 817 showed 72% control against carmine spider mite.

(5) The Contrastive Test Results of Some Compounds and Contrasts

Contrastive tests were carried out between some compounds and contrasts. The test results are listed in table 115 to table 116 ("///" in the following tables means no test).

TABLE 115 contrastive tests against diamond back moth

| | Insecticidal activity against diamond back moth (%) | | |
|---|---|---|---|
| Compound No. | 600 mg/L | 100 mg/L | 10 mg/L |
| 241 | 100 | 71 | 29 |
| 797 | 100 | 85 | 65 |
| 817 | 100 | 70 | 21 |
| 865 | 100 | 50 | 42 |
| 10932 | 100 | 50 | 25 |
| CK1 | 43 | /// | /// |
| CK2 | 20 | /// | /// |
| CK3 | 0 | /// | /// |
| CK4 | 0 | /// | /// |
| CK5 | 0 | /// | /// |

TABLE 116 contrastive tests against peach aphid

| | Insecticidal activity against peach aphid (%) | | |
|---|---|---|---|
| Compound No. | 600 mg/L | 100 mg/L | 10 mg/L |
| 23 | 100 | 94 | /// |
| 38 | 100 | 100 | /// |
| 244 | 91 | 71 | 65 |
| 406 | 100 | 95 | 28 |
| 522 | 100 | 96 | 33 |
| 575 | 92 | 88 | 73 |
| 587 | 100 | 93 | /// |
| 800 | 100 | 100 | 71 |
| 815 | 100 | 94 | 41 |
| 817 | 100 | 100 | /// |
| 4733 | 100 | 100 | 88 |
| 5935 | 100 | 56 | 61 |
| CK1 | 91 | 0 | 0 |

TABLE 116-continued contrastive tests against peach aphid

| | Insecticidal activity against peach aphid (%) | | |
|---|---|---|---|
| Compound No. | 600 mg/L | 100 mg/L | 10 mg/L |
| CK2 | 100 | 55 | 0 |
| CK3 | 77 | 19 | 0 |
| CK4 | 0 | /// | /// |
| CK5 | 100 | 22 | 0 |

We claim:

1. A kind of pyrazolyl pyrimidinamine compounds represented by general formula I:

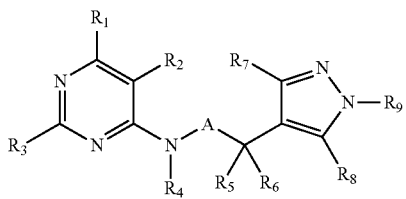

I wherein:
$R_1$ is selected from halogen, $C_1$-$C_{12}$alkyl, $C_3$-$C_{12}$cycloalkyl, haloC$_1$-$C_{12}$alkyl, $C_2$-$C_{12}$alkenyl, haloC$_2$-$C_{12}$alkenyl, $C_2$-$C_{12}$alkynyl, haloC$_2$-$C_{12}$alkynyl, $C_1$-$C_{12}$alkoxyC$_1$-$C_{12}$alkyl or haloC$_1$-$C_{12}$alkoxyC$_1$-$C_{12}$alkyl;

$R_2$ is selected from halogen, cyano, nitro, $C_1$-$C_{12}$alkyl, $C_1$-$C_{12}$alkoxy or haloC$_1$-$C_{12}$alkoxy;

$R_3$ is selected from H, halogen, $C_1$-$C_{12}$alkyl, haloC$_1$-$C_{12}$alkyl, $C_3$-$C_8$cycloalkyl, $C_1$-$C_{12}$alkoxy, $C_1$-$C_{12}$alkylthio or $C_1$-$C_{12}$alkylsulfonyl;

$R_4$ is selected from H, OH, H(C)=O, $C_1$-$C_{12}$alkyl, haloC$_1$-$C_{12}$alkyl, $C_1$-$C_{12}$alkoxy, haloC$_1$-$C_{12}$alkoxy, $C_3$-$C_{12}$cycloalkyl, $C_1$-$C_{12}$alkylthio, $C_2$-$C_{12}$alkenylthio, $C_2$-$C_{12}$alkenyl, $C_2$-$C_{12}$alkynyl, haloC$_2$-$C_{12}$alkenyl, haloC$_2$-$C_{12}$alkynyl, $C_1$-$C_{12}$alkoxyC$_1$-$C_{12}$alkyl, haloC$_1$-$C_{12}$alkoxyC$_1$-$C_{12}$alkyl, $C_1$-$C_{12}$alkylthioC$_1$C$_{12}$alkyl, haloC$_1$-$C_{12}$alkylthioC$_1$-$C_{12}$alkyl, haloC$_1$-$C_{12}$alkylsulfinyl, $C_1$-$C_{12}$alkylsulfonyl, haloC$_1$-$C_{12}$alkysulfonyl, $C_1$-$C_{12}$alkylaminosulfonyl, di($C_1$-$C_{12}$alkyl)aminosulfonyl, $C_1$-$C_{12}$alkylsulfonylaminocarbonyl, $C_1$-$C_{12}$alkylcarbonylaminosulfonyl, $C_3$-$C_{12}$cycloalkyloxycarbony, $C_1$-$C_{12}$alkylcarbonyl, haloC$_1$-$C_{12}$alkylcarbonyl, $C_1$-$C_{12}$alkoxycarbonyl, haloC$_1$-$C_{12}$alkoxycarbonyl, $C_1$-$C_{12}$alkylcarbonylC$_1$-$C_{12}$alkyl, $C_1$-$C_{12}$alkoxycarbonylC$_1$-$C_{12}$alkyl, $C_1$-$C_{12}$alkylaminocarbonyl, di($C_1$-$C_{12}$alkyl)aminocarbonyl, $C_2$-$C_{12}$alkenoxycarbonyl, $C_2$-$C_{12}$alkynoxycarbonyl, $C_1$-$C_{12}$alkoxyC$_1$-$C_{12}$alkoxycarbonyl, $C_1$-$C_{12}$alkylaminothio, di($C_1$-$C_{12}$alkyl)aminothio, unsubstituted or further substituted (hetero)arylcarbonylC$_1$-$C_6$alkyl, (hetero)arylcarbonyl, (hetero)aryloxycarbonyl, (hetero)arylC$_1$-$C_6$alkyloxycarbonyl or (hetero)arylC$_1$-$C_6$alkyl by 1 to 5 following groups: halogen, nitro, cyano, $C_1$-$C_6$alkyl, haloC$_1$-$C_6$alkyl, $C_1$-$C_6$alkoxy or haloC$_1$-$C_6$alkoxy;

$R_5$, $R_6$ may be the same or different, selected respectively from H, halogen, $C_1$-$C_{12}$alkyl or $C_1$-$C_{12}$alkoxy; or $R_5$, $R_6$ and their conjoint carbon can also form a $C_3$-$C_8$ cycle;

$R_7$ is selected from H, $C_1$-$C_{12}$alkyl or haloC$_1$-$C_{12}$alkyl;
$R_8$ is selected from H, $C_1$-$C_{12}$alkyl or haloC$_1$-$C_{12}$alkyl;
$R_9$ is selected from substituted or further substituted (hetero)aryl, (hetero)arylmethyl, (hetero)arylcarbonyl, (hetero)arylmethylcarbonyl or (hetero) aryloxycarbonyl by 1 to 5 $R_{10}$;
$R_{10}$ is selected from halogen, OH, amino, cyano, nitro, $C_1$-$C_{12}$alkyl, haloC$_1$-$C_{12}$alkyl, $C_1$-$C_{12}$alkoxy, haloC$_1$-$C_{12}$alkoxy, $C_3$-$C_{12}$cycloalkyl, $C_1$-$C_{12}$alkylamino, haloC$_1$-$C_{12}$alkylamino, di($C_1$-$C_{12}$alkyl)amino, halodi($C_1$-$C_{12}$alkyl)amino, C(=O)NR$_{11}$R$_{12}$, $C_1$-$C_{12}$alkylthio, haloC$_1$-$C_{12}$alkylthio, $C_2$-$C_{12}$alkenyl, $C_2$-$C_{12}$alkynyl, $C_2$-$C_{12}$alkenoxy, haloC$_2$-$C_{12}$alkenoxy, $C_2$-$C_{12}$alkynoxy, haloC$_2$-$C_{12}$alkynoxy, $C_1$-$C_{12}$alkylsulfonyl, haloC$_1$-$C_{12}$alkylsulfonyl, $C_1$-$C_{12}$alkylcarbonyl, haloC$_1$-$C_{12}$alkylcarbonyl, $C_1$-$C_{12}$alkoxycarbonyl, haloC$_1$-$C_{12}$alkoxycarbonyl, $C_1$-$C_{12}$alkoxyC$_1$-$C_{12}$alkyl, haloC$_1$-$C_{12}$alkoxyC$_1$-$C_{12}$alkyl, $C_1$-$C_{12}$alkylthioC$_1$-$C_{12}$alkyl, haloC$_1$-$C_{12}$alkylthioC$_1$-$C_{12}$alkyl, $C_1$-$C_{12}$alkoxycarbonylC$_1$-$C_{12}$alkyl, haloC$_1$-$C_{12}$alkoxycarbonylC$_1$-$C_{12}$alkyl, $C_1$-$C_{12}$alkylthiocarbonylC$_1$-$C_{12}$alkyl, haloC$_1$-$C_{12}$alkylthiocarbonylC$_1$-$C_{12}$alkyl, $C_1$-$C_{12}$alkylcarbonyloxy, haloC$_1$-$C_{12}$alkylcarbonyloxy, $C_1$-$C_{12}$alkoxycarbonyloxy, haloC$_1$-$C_{12}$alkoxycarbonyloxy, $C_1$-$C_{12}$alkylsulfonyloxy, haloC$_1$-$C_{12}$alkylsulfonyloxy, $C_1$-$C_{12}$alkoxyC$_1$-$C_{12}$alkoxy or haloC$_1$-$C_{12}$alkoxyC$_1$-$C_{12}$alkoxy;

$R_{11}$, $R_{12}$ may be the same or different, selected respectively from H, $C_1$-$C_{12}$alkyl or haloC$_1$-$C_{12}$alkyl;
A is selected from (CHR$_{13}$)$_m$; m is selected from 1 or 2;
$R_{13}$ is selected from H, $C_1$-$C_{12}$alkyl or haloC$_1$-$C_{12}$alkyl;
or the salts formed from the compounds represented by general formula I.

2. The pyrazolyl pyrimidinamine compounds according to the claim 1, characterized in that wherein general formula I:
$R_1$ is selected from halogen, $C_1$-$C_6$alkyl, $C_3$-$C_6$cycloalkyl, haloC$_1$-$C_6$alkyl, $C_2$-$C_6$alkenyl, haloC$_2$-$C_6$alkenyl, $C_2$-$C_6$alkynyl, haloC$_2$-$C_6$alkynyl, $C_1$-$C_6$alkoxyC$_1$-$C_6$alkyl or haloC$_1$-$C_6$alkoxyC$_1$-$C_6$alkyl;

$R_2$ is selected from halogen, cyano, nitro, $C_1$-$C_6$alkyl, $C_1$-$C_6$alkoxy or haloC$_1$-$C_6$alkoxy;

$R_3$ is selected from H, halogen, $C_1$-$C_6$alkyl, haloC$_1$-$C_6$alkyl, $C_3$-$C_6$cycloalkyl, $C_1$-$C_6$alkoxy, $C_1$-$C_6$alkylthio or $C_1$-$C_6$alkylsulfonyl;

$R_4$ is selected from H, OH, H(C)=O, $C_1$-$C_6$alkyl, $C_1$-$C_6$alkylcarbonyl or $C_1$-$C_6$alkylsulfonyl;

$R_5$, $R_6$ may be the same or different, selected respectively from H, halogen, $C_1$-$C_6$alkyl or $C_1$-$C_6$alkoxy; or $R_5$, $R_5$ and their conjoint carbon can also form a $C_3$-$C_6$ cycle;

$R_7$ is selected from H, $C_1$-$C_6$alkyl or haloC$_1$-$C_6$alkyl;
$R_8$ is selected from H, $C_1$-$C_6$alkyl or haloC$_1$-$C_6$alkyl;
$R_9$ is selected from unsubstituted or further substituted (hetero)aryl, (hetero)arylmethyl, (hetero)arylcarbonyl, (hetero)arylmethylcarbonyl or (hetero)aryloxycarbonyl by 1 to 5 $R_{10}$;
$R_{10}$ is selected from halogen, OH, amino, cyano, nitro, $C_1$-$C_6$alkyl, haloC$_1$-$C_6$alkyl, $C_1$-$C_6$alkoxy, haloC$_1$-$C_6$alkoxy, $C_3$-$C_6$cycloalkyl, $C_1$-$C_6$alkylamino, haloC$_1$C$_6$alkylamino, di($C_1$-$C_6$alkyl)amino, halodi($C_1$-$C_6$alkyl)amino, C(=O)NR$_{11}$R$_{12}$, $C_1$-$C_6$alkylthio, haloC$_1$-$C_6$alkylthio, $C_2$-$C_6$alkenyl, $C_2$-$C_6$alkynyl, $C_2$-$C_6$alkenoxy, haloC$_2$-$C_6$alkenoxy, $C_2$-$C_6$alkynoxy, haloC$_2$-$C_6$alkynoxy, $C_1$-$C_6$alkylsulfonyl, haloC$_1$-$C_6$alkylsulfonyl, $C_1$-$C_6$alkylcarbonyl, haloC$_1$-$C_6$alkylcarbonyl, $C_1$-$C_6$alkoxycarbonyl, haloC$_1$-

C$_6$alkoxycarbonyl, C$_1$-C$_6$alkoxyC$_1$-C$_{12}$alkyl, haloC$_1$-C$_6$alkoxyC$_1$-C$_6$alkyl, C$_1$-C$_6$alkylthioC$_1$-C$_6$alkyl, haloC$_1$-C$_6$alkylthioC$_1$-C$_6$alkyl, C$_1$-C$_6$alkoxycarbonylC$_1$-C$_6$alkyl, haloC$_1$-C$_6$alkoxycarbonylC$_1$-C$_6$alkyl, C$_1$-C$_6$alkyhhiocarbonylC$_1$-C$_6$alkyl, haloC$_1$-C$_6$alkylthiocarbonylC$_1$-C$_6$alkyl, C$_1$-C$_6$alkylcarbonyloxy, haloC$_1$-C$_6$alkylcarbonyloxy, C$_1$-C$_6$alkoxycarbonyloxy, haloC$_1$-C$_6$alkoxycarbonyloxy, C$_1$-C$_6$alkylsulfonyloxy, haloC$_1$-C$_6$alkylsulfonyloxy, C$_1$-C$_6$alkoxyC$_1$-C$_6$alkoxy or haloC$_1$-C$_6$alkoxyC$_1$-C$_6$alkoxy;

R$_{11}$, R$_{12}$ may be the same or different, selected respectively from H, C$_1$-C$_6$alkyl or haloC$_1$-C$_6$alkyl;

A is selected from (CHR$_{13}$)$_m$; m is selected from 1 or 2;

R$_{13}$ is selected from H, C$_1$-C$_6$alkyl or haloC$_1$-C$_6$alkyl;

or the salts formed from the compounds represented by general formula I.

3. The pyrazolyl pvrimidinamine compounds according to the claim 2, characterized in that wherein general formula IB, IC, ID, IE or IF:

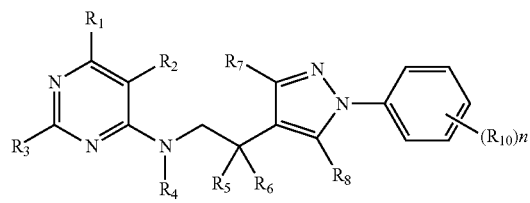

IB

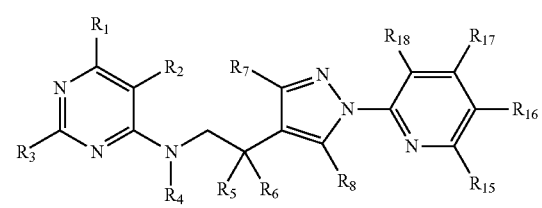

IC

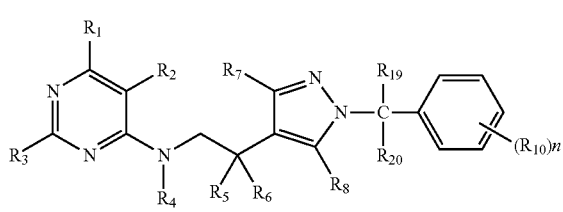

ID

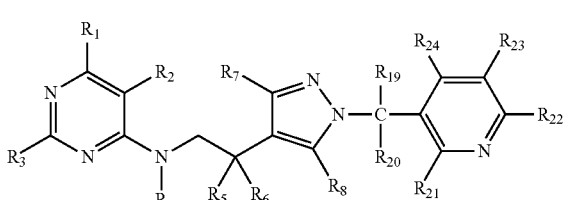

IE

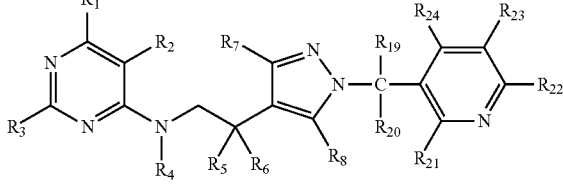

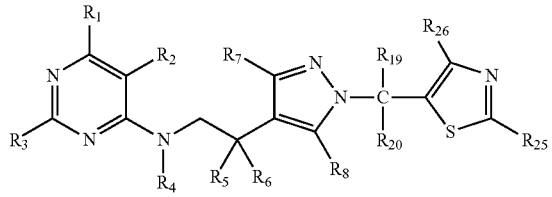

IF wherein:
R$_1$ is selected from halogen, C$_1$-C$_4$alkyl, C$_3$-C$_4$cycloalkyl, haloC$_1$-C$_4$alkyl, C$_2$-C$_4$alkenyl, haloC$_2$-C$_4$alkenyl, C$_2$-C$_4$alkynyl, haloC$_2$-C$_4$alkynyl, C$_1$-C$_4$alkoxyC$_1$-C$_4$alkyl or haloC$_1$-C$_4$alkoxyC$_1$-C$_4$alkyl;

R$_2$ is selected from halogen, cyano, nitro, C$_1$-C$_4$alkyl, C$_1$-C$_4$alkoxy or haloC$_1$-C$_4$alkoxy;

R$_3$ is selected from H, halogen, C$_1$-C$_4$alkyl, haloC$_1$-C$_4$alkyl, C$_3$-C$_4$cycloalkyl, C$_1$-C$_4$alkoxy, C$_1$-C$_4$alkylthio or C$_1$-C$_4$alkylsulfonyl;

R$_4$ is selected from H, OH, H(C)=O, C$_1$-C$_4$alkyl, C$_1$-C$_4$alkylcarbonyl or C$_1$-C$_4$alkylsulfonyl;

R$_5$, R$_6$ may be the same or different, selected respectively from H, halogen, C$_1$-C$_4$alkyl or C$_1$-C$_4$alkoxy; or R$_5$, R$_6$ and their conjoint carbon can also form a C$_3$-C$_4$ cycle;

R$_7$ is selected from H, C$_1$-C$_4$alkyl or haloC$_1$-C$_4$alkyl;

R$_8$ is selected from H, C$_1$-C$_4$alkyl or haloC$_1$-C$_4$alkyl;

R$_{10}$ is selected from halogen, OH, amino, cyano, nitro, C$_1$-C$_4$alkyl, haloC$_1$-C$_4$alkyl, C$_1$-C$_4$alkoxy, haloC$_1$-C$_4$alkoxy, C$_3$-C$_4$cycloalkyl, C$_1$-C$_4$alkylamino, haloC$_1$-C$_4$alkylamino, di(C$_1$-C$_4$alkyl)amino, halodi(C$_1$-C$_4$alkyl)amino, C(=O)NR$_{11}$R$_{12}$, C$_1$-C$_4$alkylthio, haloC$_1$-C$_4$alkylthio, C$_2$-C$_4$alkenyl, C$_2$-C$_4$alkynyl, C$_2$-C$_4$alkenoxy, haloC$_2$-C$_4$alkenoxy, C$_2$-C$_4$alkynoxy, haloC$_2$-C$_4$alkynoxy, C$_1$-C$_4$alkylsulfonyl, haloC$_1$-C$_4$alkysulfonyl, C$_1$-C$_4$alkylcarbonyl, haloC$_1$-C$_4$alkylcarbonyl, C$_1$-C$_4$alkoxycarbonyl, haloC$_1$-C$_4$alkoxycarbonyl, C$_1$-C$_4$alkoxyC$_1$-C$_{12}$alkyl, haloC$_1$-C$_4$alkoxyC$_1$-C$_4$alkyl, C$_1$-C$_4$alkylthioC$_1$-C$_4$alkyl, haloC$_1$-C$_4$alkylthioC$_1$-C$_4$alkyl, C$_1$-C$_4$alkoxycarbonylC$_1$-C$_4$alkyl, haloC$_1$-C$_4$alkoxycarbonylC$_1$-C$_4$alkyl, C$_1$-C$_4$alkylthiocarbonylC$_1$-C$_4$alkyl, haloC$_1$-C$_4$alkylthiocarbonylC$_1$-C$_4$alkyl, C$_1$-C$_4$alkylcarbonyloxy, haloC$_1$-C$_4$alkylcarbonyloxy, C$_1$-C$_4$alkoxycarbonyloxy, haloC$_1$-C$_4$alkoxycarbonyloxy, C$_1$-C$_4$alkylsulfonyloxy, haloC$_1$-C$_4$alkylsulfonyloxy, C$_1$-C$_4$alkoxyC$_1$-C$_4$alkoxy or haloC$_1$-C$_4$alkoxyC$_1$-C$_4$alkoxy;

the integer n is selected from 0 to 5, when n is 0, the benzene ring is unsubstituted phenyl; when n is more than 1, R$_{10}$ may be the same or different;

R$_{11}$, R$_{12}$ may be the same or different, selected respectively from H, C$_1$-C$_4$alkyl or haloC$_1$-C$_4$alkyl;

R$_{15}$, R$_{16}$, R$_{17}$, R$_{18}$ may be the same or different, selected respectively from H, halogen, cyano, nitro, C$_1$-C$_4$alkyl, haloC$_1$-C$_4$alkyl, C$_1$-C$_4$alkoxy, or haloC$_1$-C$_4$alkoxy;

R$_{19}$, R$_{20}$ may be the same or different, selected respectively from H, halogen, OH, cyano, nitro, C$_1$-C$_4$alkyl, haloC$_1$-C$_4$alkyl, C$_1$-C$_4$alkoxy, haloC$_1$-C$_4$alkoxy, C$_1$-C$_4$alkylthio, haloC$_1$-C$_4$alkoxy, C$_3$-C$_4$cycloalkyl, unsubstituted or further substituted (hetero)aryl, (hetero)arylmethyl, (hetero)arylcarbonyl, (hetero)arylmethylcarbonyl or (hetero)aryloxycarbonyl by 1 to 5 R$_{10}$;

$R_{21}$, $R_{22}$, $R_{23}$, $R_{24}$ may be the same or different, selected respectively from H, halogen, $C_1$-$C_4$alkyl, halo$C_1$-$C_4$alkyl, $C_1$-$C_4$alkoxy or halo$C_1$-$C_4$alkoxy;

$R_{25}$, $R_{26}$ may be the same or different, selected respectively from H, halogen, $C_1$-$C_4$alkyl, halo$C_1$-$C_4$alkyl, $C_1$-$C_4$alkoxy, halo$C_1$-$C_4$alkoxy, $C_1$-$C_4$alkylthio, halo$C_1$-$C_4$alkylthio, $C_3$-$C_4$cycloalkyl, unsubstituted or further substituted (hetero)aryl, (hetero)arylmethyl, (hetero)arylcarbonyl, (hetero)arylmethylcarbonyl or (hetero)aryloxycarbonyl by 1 to 5 $R_{10}$;

or the salts formed from the compounds represented by general formula IB, IC, ID, IE or IF with hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, sorbic acid, malic acid or citric acid.

4. The pyrazolyl pyrimidinamine compounds according to the claim 3, characterized in that wherein general formula IB, IC, ID, IE or IF:

$R_1$ is selected from F, Cl, Br, $CH_3$, $C_2H_5$, n-$C_3H_7$, i-$C_3H_7$, n-$C_4H_9$, s-$C_4H_9$, i-$C_4H_9$, t-$C_4H_9$, cyclopropyl, cyclobutyl, $CH_2F$, $CH_2Cl$, $CHF_2$, $CF_3$, $CH_2CF_3$, $CH_2OCH_3$, $CH_2OCH_2CH_3$ or $CH_2OCH_2CF_3$;

$R_2$ is selected from F, Cl, Br, cyano, nitro, $CH_3$, $C_2H_5$, $OCH_3$, $OC_2H_5$ or $OCH_2CF_3$;

$R_3$ is selected from H, Cl, Br, $CH_3$, $C_2H_5$, n-$C_3H_7$, i-$C_3H_7$, n-$C_4H_9$, s-$C_4H_9$, i-$C_4H_9$, t-$C_4H_9$, $CH_2F$, $CH_2Cl$, $CHF_2$, $CF_3$, $CH_2CF_3$, $OCH_3$, $OCH_2CH_3$, $SCH_3$, $SCH_2CH_3$, $SO_2CH_3$ or $SO_2CH_2CH_3$;

$R_4$ is selected from H, OH, H(C)=O, $COC_2H_5$, $CH_3$, $C_2H_5$, $SO_2CH_3$ or $SO_2CH_2CH_3$;

$R_5$, $R_6$ may be the same or different, selected respectively from H, F, Cl, Br, I, $CH_3$, $C_2H_5$, n-$C_3H_7$, i-$C_3H_7$, n-$C_4H_9$, s-$C_4H_9$, i-$C_4H_9$, t-$C_4H_9$, $OCH_3$, $OCH_2CH_3$, n-$C_3H_7O$, i-$C_3H_7O$, n-$C_4H_9O$, s-$C_4H_9O$, i-$C_4H_9O$ or t-$C_4H_9O$;

$R_7$ is selected from H, $CH_3$, $C_2H_5$ or $CF_3$;

$R_8$ is selected from H, $CH_3$, $C_2H_5$ or $CF_3$;

$R_{10}$ is selected from F, Cl, Br, I, CN, $NH_2$, $NO_2$, $CH_3$, $C_2H_5$, n-$C_3H_7$, n-$C_4H_9$, s-$C_4H_9$, i-$C_4H_9$, t-$C_4H_9$, $CF_3$, $CCl_3$, $CF_2Cl$, $CFCl_2$, $OCH_3$, $OCH_2CH_3$, n-$C_3H_7O$, i-$C_3H_7O$, n-$C_4H_9O$, s-$C_4H_9O$, i-$C_4H_9O$, t-$C_4H_9O$, $OCF_3$, $OCH_2CF_3$, $COOCH_3$, $COOCH_2CH_3$, $CONHCH_3$, $CONHC_2H_5$ or $CON(CH_3)_2$;

the integer n is selected from 0 to 5, when n is 0, the benzene ring is unsubstituted phenyl; when n is more than 1, $R_{10}$ may be the same or different;

$R_{15}$, $R_{16}$, $R_{17}$, $R_{18}$ may be the same or different, selected respectively from H, Cl, CN, $NO_2$, $CH_3$, $CF_3$, $OCH_3$ or $OCF_3$;

$R_{19}$, $R_{20}$ may be the same or different, selected respectively from H, F, Cl, Br, OH, CN, $NO_2$, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, $CH_2CF_3$, $OCH_3$, $OCH_2CH_3$, n-$C_3H_7O$, i-$C_3H_7O$, n-$C_4H_9O$, s-$C_4H_9O$, i-$C_4H_9O$, t-$C_4H_9O$, $OCF_3$, $OCH_2CF_3$, unsubstituted or further substituted (hetero)aryl, (hetero)arylmethyl, (hetero)arylcarbonyl, (hetero)arylmethylcarbonyl or (hetero)aryloxycarbonyl by 1 to 5 $R_{10}$;

$R_{21}$, $R_{22}$, $R_{23}$, $R_{24}$ may be the same or different, selected respectively from H, F, Cl, Br, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, $CH_2CF_3$, $OCH_3$, $OCH_2CH_3$, n-$C_3H_7O$, i-$C_3H_7O$, n-$C_4H_9O$, s-$C_4H_9O$, i-$C_4H_9O$, t-$C_4H_9O$, $OCF_3$ or $OCH_2CF_3$;

$R_{25}$, $R_{26}$, may be the same or different, selected respectively from H, F, Cl, Br, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, $CH_2CF_3$, $OCH_3$, $OCH_2CH_3$, n-$C_3H_7O$, i-$C_3H_7O$, n-$C_4H_9O$, s-$C_4H_9O$, i-$C_4H_9O$, t-$C_4H_9O$, $OCF_3$, $OCH_2CF_3$, unsubstituted or further substituted (hetero)aryl, (hetero)arylmethyl, (hetero)arylcarbonyl, (hetero)arylmethylcarbonyl or (hetero)aryloxycarbonyl by 1 to 5 $R_{10}$;

or the salts formed from the compounds represented by general formula IB, IC, ID, IE or IF with hydrochloric acid, sulfuric acid, phosphoric acid, formic acid, acetic acid, trifinoroacetic acid, oxalic acidonethylsulfonic acid, p-toluenesulfonic acid, benzoic acid, alizaric acid or maleic acid.

5. The pyrazolyl pyrimidinamine compounds according to the claim 4, characterized in that wherein general formula IB, IC, ID, IE or IF:

$R_1$ is selected from F, Cl, Br, $CH_3$, $C_2H_5$, cyclopropyl, cyclobutyl, $CH_2F$, $CH_2Cl$, $CHF_2$, $CF_3$ or $CH_2CF_3$;

$R_2$ is selected from F, Cl, Br, cyano, nitro, $CH_3$, $C_2H_5$, $OCH_3$ or $OC_2H_5$;

$R_3$ is selected from H, Cl, Br, $CH_3$, $C_2H_5$, i-$C_3H_7$, $CF_3$, $OCH_3$, $OCH_2CH_3$, $SCH_3$, $SCH_2CH_3$, $SO_2CH_3$ or $SO_2CH_2CH_3$;

$R_4$ is selected from H, OH, H(C)=O, $COC_2H_5$, $CH_3$, $C_2H_5$, $SO_2CH_3$ or $SO_2CH_2CH_3$;

$R_5$, $R_6$ may be the same or different, selected respectively from H, F, Cl, Br, I, $CH_3$, $C_2H_5$, $OCH_3$ or $OCH_2CH_3$;

$R_7$ is selected from H, $CH_3$, $C_2H_5$ or $CF_3$;

$R_8$ is selected from H, $CH_3$, $C_2H_5$ or $CF_3$;

$R_{10}$ is selected from F, Cl, Br, I, CN, $NH_2$, $NO_2$, $CH_3$, $C_2H_5$, i-$C_3H_7$, t-$C_4H_9$, $CF_3$, $CCl_3$, $OCH_3$, $OCH_2CH_3$, $OCF_3$ or $OCH_2CF_3$;

the integer n is selected from 0 to 5, when n is 0, the benzene ring is unsubstituted phenyl; when n is more than 1, $R_{10}$ may be the same or different;

$R_{15}$, $R_{16}$, $R_{17}$, $R_{18}$ may be the same or different, selected respectively from H, Cl, CN, $NO_2$, $CH_3$, $CF_3$, $OCH_3$ or $OCF_3$;

$R_{19}$, $R_{20}$ may be the same or different, selected respectively from H, F, Cl, Br, OH, CN, $NO_2$, $CH_3$, $C_2H_5$, i-$C_3H_7$, t-$C_4H_9$, $CF_3$, $CH_2CF_3$, $OCH_3$, $OCH_2CH_3$, $OCF_3$ or $OCH_2CF_3$;

$R_{21}$, $R_{22}$, $R_{23}$, $R_{24}$ may be the same or different, selected respectively from H, F, Cl, Br, $CH_3$, $C_2H_5$, $CF_3$, $CH_2CF_3$, $OCH_3$, $OCH_2CH_3$, $OCF_3$ or $OCH_2CF_3$;

$R_{25}$, $R_{26}$ may be the same or different, selected respectively from H, F, Cl, Br, $CH_3$, $C_2H_5$, i-$C_3H_7$, t-$C_4H_9$, $CF_3$, $CH_2CF_3$, $OCH_3$, $OCH_2CH_3$, $OCF_3$, $OCH_2CF_3$, unsubstituted or further substituted (hetero)aryl, (hetero)arylmethyl, (hetero)arylcarbonyl, (hetero)arylmethylcarbonyl or (hetero)aryloxycarbonyl by 1 to 5 $R_{10}$;

or the salts formed from the compounds represented by general formula IB, IC, ID, IE or IF with hydrochloric acid, sulfuric acid, phosphoric acid, formic acid, acetic acid, trifluoroacetic acid, oxalic acid, methylsulfonic acid, p-toluenesulfonic acid or benzoic acid.

6. The pyrazolyl pyrimidinamine compounds according to the claim 5, characterized in that wherein general formula IB, IC or ID:

$R_1$ is selected from $CH_3$, $C_2H_5$, $CHF_2$, $CF_3$ or $CH_2CF_3$;

$R_2$ is selected from F, Cl, Br, cyano or nitro;

$R_3$ is selected from H, Cl, $CH_3$, $CF_3$, $OCH_3$, $SCH_3$ or $SO_2CH_3$;

$R_4$ is selected from H, H(C)=O, $COC_2H_5$, $CH_3$, $C_2H_5$ or $SO_2CH_3$;

$R_5$, $R_6$ may be the same or different, selected respectively from H or $CH_3$;

$R_7$ is selected from H, $CH_3$, $C_2H_5$ or $CF_3$;
$R_8$ is selected from H, $CH_3$, $C_2H_5$ or $CF_3$;
$R_{10}$ is selected from F, Cl, Br, I, CN, $NO_2$, $CH_3$, $C_2H_5$, $CF_3$, $OCH_3$ or $OCF_3$;
the integer n is selected from 0 to 5, when n is 0, the benzene ring is unsubstituted phenyl; when n is more than 1, $R_{10}$ may be the same or different;
$R_{15}$, $R_{16}$, $R_{17}$, $R_{18}$ may be the same or different, selected respectively from H, Cl, CN, $NO_2$, $CH_3$ or $CF_3$;
$R_{19}$, $R_{20}$ is selected from H;
or the salts formed from the compounds represented by general formula IB, IC or ID with hydrochloric acid or sulfuric acid.

7. The pyrazolyl pyrimidinamine compounds according to the claim 6, characterized in that wherein general formula IB, IC or ID:
$R_1$ is selected from $CH_3$, $C_2H_5$, $CHF_2$ or $CF_3$;
$R_2$ is selected from Cl;
$R_3$ is selected from H or $CH_3$;
$R_4$, $R_5$, $R_6$, $R_7$, $R_8$ is selected from H;
$R_{10}$ is selected from F, Cl, $CH_3$, $CF_3$, $OCH_3$ or $OCF_3$;
the integer n is selected from 0 to 5, when n is 0, the benzene ring is unsubstituted phenyl; when n is more than 1, $R_{10}$ may be the same or different;
$R_{15}$, $R_{16}$, $R_{17}$, $R_{18}$ may be the same or different, selected respectively from H or Cl;
$R_{19}$, $R_{20}$ is selected from H;
or the salts formed from the compounds represented by general formula IB, IC or ID with hydrochloric acid.

8. A method to prepare the compounds represented by the general formula I of the claim 1: when $R_4$ is H, the compounds represented by the general formula I-1 are prepared; when $R_4$ is not H, the compounds represented by the general formula I-2 are prepared, the equation is as follows:

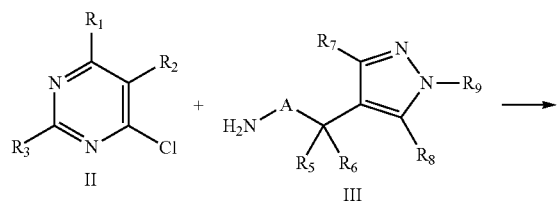

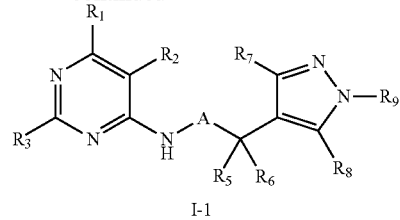

I-1

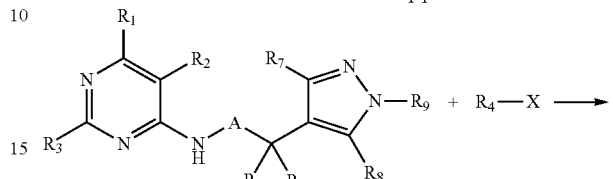

I-1

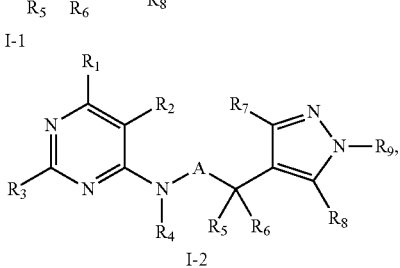

I-2 wherein the definition of each substituent is defined as the claim 1.

9. A method for controlling plant pathogens, diseases, insects, and/or mites, comprising: applying the pyrazolyl pyrimidinamine compounds having general formula I or their salts according to claim 1 to a plant or other agriculture.

10. A composition of fungicides, insecticides/acaricides, comprising the compounds represented by general formula I or their salts according to claim 1 as an active ingredient and acceptable carrier, wherein the weight percentage of the active ingredient in the composition is 0.1-99%.

11. A method for controlling plant pathogens, diseases, insects, and/or mites, comprising: applying the composition according to claim 10 to a plant or other agriculture.

* * * * *